United States Patent
Martin et al.

(10) Patent No.: US 9,566,276 B2
(45) Date of Patent: Feb. 14, 2017

(54) PHTHALAZINONE DERIVATIVES

(71) Applicant: KUDOS PHARMACEUTICALS LIMITED, Cambridge, Cambridgeshire (GB)

(72) Inventors: Niall Morrison Barr Martin, Cambridge (GB); Graeme Cameron Smith, Cambridge (GB); Stephen Philip Jackson, Cambridge (GB); Vincent Junior M Loh, Horsham (GB); Xiao-Ling Fan Cockcroft, Horsham (GB); Ian Timothy Williams Matthews, Horsham (GB); Keith Allan Menear, Horsham (GB); Frank Kerrigan, Cornwall (GB); Alan Ashworth, London (GB)

(73) Assignee: KUDOS PHARMACEUTICALS LIMITED, Cambridge, Cambridgeshire (GB)

( * ) Notice: Subject to any disclaimer, the term of this patent is extended or adjusted under 35 U.S.C. 154(b) by 0 days.

(21) Appl. No.: 14/853,360

(22) Filed: Sep. 14, 2015

(65) Prior Publication Data
US 2016/0000781 A1 Jan. 7, 2016

Related U.S. Application Data

(63) Continuation of application No. 14/483,663, filed on Sep. 11, 2014, now Pat. No. 9,169,235, which is a
(Continued)

(30) Foreign Application Priority Data

Mar. 12, 2003 (GB) .................... 0305681.9

(51) Int. Cl.
*A61K 31/502* (2006.01)
*A61K 31/00* (2006.01)
(Continued)

(52) U.S. Cl.
CPC ............. *A61K 31/502* (2013.01); *A61K 31/00* (2013.01); *A61K 31/506* (2013.01);
(Continued)

(58) Field of Classification Search
CPC ..................................................... A61K 31/50
See application file for complete search history.

(56) References Cited

U.S. PATENT DOCUMENTS 3,813,384 A 5/1974 Vogelsang et al.
4,665,181 A 5/1987 Thomas et al.
(Continued)

FOREIGN PATENT DOCUMENTS

DE 2143745 3/1973
DE 3813531 4/1988
(Continued)

OTHER PUBLICATIONS

"Burger's Medicinal Chemistry and Drug Discovery," 5th Ed., Part 1, Ed. Wolff, pp. 975-977 (1995).
"From DNA Damage and Stress Signalling to cell Death Poly ADP-ribosylation Reactions," Eds. de Murcia and Shall, Oxford University Press (2000).
"Handbook of Pharmaceutical Additives," 2 Ed., Synapse Information Resources, Inc., Endicott, New York, USA (2002).
"Hawley's Condensed Chemical Dictionary," 13th Ed., Van Nostrand Reinhold Eds., pp. 716 and 825 (1997).
Affar et al., "Immunodot Blot Method for Detection of Poly(ADP-ribose) Synthesized in Vitro and in Vivo," Analytical Biochemistry 259:280-283 (1998).
Al-Dabbagh et al., "Species Differences in Oxidative Drug Metabolism: Some Basic Considerations," Archives of Toxicology, Suppl. 7:219-231 (1984).
Ame et al., "PARP-2, A novel Mammalian DNA Damage-dependent Poly(ADP-ribose) Polymerase," Journal of Biological Chemistry, 274(25):17860-17868 (1999).
(Continued)

*Primary Examiner* — Paul V Ward
(74) *Attorney, Agent, or Firm* — Michael Best & Friedrich LLP

(57) ABSTRACT

Compounds of the formula (I):

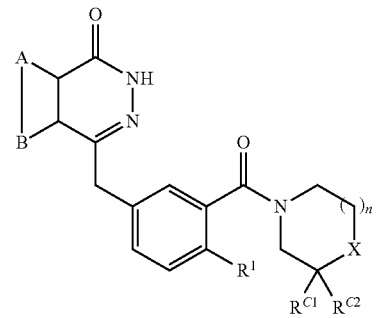

wherein A and B together represent an optionally substituted, fused aromatic ring; X can be $NR^X$ or $CR^XR^Y$; if $X=NR^X$ then n is 1 or 2 and if $X=CR^XR^Y$ then n is 1; $R^X$ is selected from the group consisting of H, optionally substituted $C_{1-20}$ alkyl, $C_{5-20}$ aryl, $C_{3-20}$heterocyclyl, amido, thioamido, ester, acyl, and sulfonyl groups; $R^Y$ is selected from H, hydroxy, amino; or $R^X$ and $R^Y$ may together form a spiro-$C_{3-7}$ cycloalkyl or heterocyclyl group; $R^{C1}$ and $R^{C2}$ are both hydrogen, or when X is $CR^XR^Y$, $R^{C1}$, $R^{C2}$, $R^X$ and $R^Y$, together with the carbon atoms to which they are attached, may form an optionally substituted fused aromatic ring; and $R^1$ is selected from H and halo.

12 Claims, 2 Drawing Sheets

Related U.S. Application Data continuation of application No. 13/179,353, filed on Jul. 8, 2011, now Pat. No. 8,912,187, which is a continuation of application No. 12/109,260, filed on Apr. 24, 2008, now Pat. No. 7,981,889, which is a continuation of application No. 10/876,080, filed on Jun. 24, 2004, now Pat. No. 7,449,464, which is a continuation-in-part of application No. 10/799,154, filed on Mar. 12, 2004, now abandoned, said application No. 10/876,080 is a continuation-in-part of application No. 60/493,399, filed on Aug. 6, 2003.

(60) Provisional application No. 60/526,244, filed on Dec. 1, 2003, provisional application No. 60/454,995, filed on Mar. 14, 2003.

(51) Int. Cl.

| | | |
|---|---|---|
| C07D 237/32 | (2006.01) | |
| C07D 401/10 | (2006.01) | |
| C07D 401/12 | (2006.01) | |
| C07D 401/14 | (2006.01) | |
| C07D 403/10 | (2006.01) | |
| C07D 403/12 | (2006.01) | |
| C07D 405/12 | (2006.01) | |
| C07D 405/14 | (2006.01) | |
| C07D 409/12 | (2006.01) | |
| C07D 409/14 | (2006.01) | |
| C07D 413/12 | (2006.01) | |
| C07D 413/14 | (2006.01) | |
| C07D 417/12 | (2006.01) | |
| C07D 417/14 | (2006.01) | |
| C07D 491/04 | (2006.01) | |
| C07D 495/04 | (2006.01) | |
| A61K 31/5377 | (2006.01) | |
| A61K 31/551 | (2006.01) | |
| A61K 45/06 | (2006.01) | |
| C07D 403/14 | (2006.01) | |
| A61K 31/506 | (2006.01) | |
| A61N 5/10 | (2006.01) | |

(52) U.S. Cl.
CPC ........ *A61K 31/5377* (2013.01); *A61K 31/551* (2013.01); *A61K 45/06* (2013.01); *A61N 5/10* (2013.01); *C07D 237/32* (2013.01); *C07D 401/10* (2013.01); *C07D 401/12* (2013.01); *C07D 401/14* (2013.01); *C07D 403/10* (2013.01); *C07D 403/12* (2013.01); *C07D 403/14* (2013.01); *C07D 405/12* (2013.01); *C07D 405/14* (2013.01); *C07D 409/12* (2013.01); *C07D 409/14* (2013.01); *C07D 413/12* (2013.01); *C07D 413/14* (2013.01); *C07D 417/12* (2013.01); *C07D 417/14* (2013.01); *C07D 491/04* (2013.01); *C07D 495/04* (2013.01)

(56) References Cited

U.S. PATENT DOCUMENTS

| | | | |
|---|---|---|---|
| 4,841,047 | A | 6/1989 | Engel et al. |
| 5,032,617 | A | 7/1991 | Lee et al. |
| 5,041,653 | A | 8/1991 | Lee et al. |
| 5,215,738 | A | 6/1993 | Lee et al. |
| 5,556,856 | A | 9/1996 | Engel et al. |
| 5,587,384 | A | 12/1996 | Zhang et al. |
| 5,648,355 | A | 7/1997 | Theoharides |
| 5,874,444 | A | 2/1999 | West |
| 5,886,178 | A | 3/1999 | Allen et al. |
| 6,197,785 | B1 | 3/2001 | Jackson et al. |
| 6,340,684 | B1 | 1/2002 | Napoletano et al. |
| 6,426,415 | B1 | 7/2002 | Jackson et al. |
| 6,476,048 | B1 | 11/2002 | Szabo et al. |
| 6,498,160 | B2 | 12/2002 | Napoletano et al. |
| 6,514,983 | B1 | 2/2003 | Li |
| 6,514,984 | B1 | 2/2003 | Watanabe |
| 6,635,642 | B1 | 10/2003 | Jackson et al. |
| 6,677,333 | B1 | 1/2004 | Seko et al. |
| 7,449,464 | B2 | 11/2008 | Martin et al. |
| 7,662,818 | B2 | 2/2010 | Martin et al. |
| 7,692,006 | B2 | 4/2010 | Menear et al. |
| 9,169,235 | B2 | 10/2015 | Martin et al. |
| 2002/0183325 | A1 | 12/2002 | Martin et al. |
| 2004/0023968 | A1 | 2/2004 | Martin et al. |
| 2005/0059663 | A1 | 3/2005 | Martin et al. |
| 2005/0080096 | A1 | 4/2005 | Ishida et al. |
| 2005/0227919 | A1 | 10/2005 | Ashworth et al. |
| 2006/0149059 | A1 | 7/2006 | Martin et al. |
| 2012/0010204 | A1 | 1/2012 | Martin et al. |

FOREIGN PATENT DOCUMENTS

| | | |
|---|---|---|
| DE | 287032 | 2/1991 |
| EP | 0030861 | 6/1981 |
| EP | 0269968 | 6/1988 |
| EP | 0389995 | 9/1989 |
| EP | 0355750 | 2/1990 |
| EP | 0502575 | 9/1992 |
| EP | 0590551 | 4/1994 |
| EP | 0634404 | 1/1995 |
| EP | 0699754 | 3/1996 |
| EP | 0705903 | 4/1996 |
| EP | 0792643 | 9/1997 |
| FR | 2262513 | 9/1975 |
| GB | 721286 | 1/1955 |
| GB | 2384776 | 3/2004 |
| IT | MI98A001671 | 4/1999 |
| JP | 54-156526 | 12/1979 |
| JP | 58-164577 | 9/1983 |
| JP | 62-252774 | 11/1987 |
| WO | WO 91/18591 | 12/1991 |
| WO | WO 93/14086 | 7/1993 |
| WO | WO 94/10151 | 5/1994 |
| WO | WO 95/24379 | 9/1995 |
| WO | WO 96/19225 | 6/1996 |
| WO | WO 98/43477 | 10/1998 |
| WO | WO 98/51308 | 11/1998 |
| WO | WO 99/08680 | 2/1999 |
| WO | WO 99/11624 | 3/1999 |
| WO | WO 99/11645 | 3/1999 |
| WO | WO 99/11649 | 3/1999 |
| WO | WO 99/44612 | 9/1999 |
| WO | WO 99/47494 | 9/1999 |
| WO | WO 00/05219 | 2/2000 |
| WO | WO 00/42040 | 7/2000 |
| WO | WO 00/44726 | 8/2000 |
| WO | WO 00/67734 | 11/2000 |
| WO | WO 01/12199 | 2/2001 |
| WO | WO 01/16136 | 3/2001 |
| WO | WO 01/16137 | 3/2001 |
| WO | WO 01/21615 | 3/2001 |
| WO | WO 01/23390 | 4/2001 |
| WO | WO 01/57038 | 8/2001 |
| WO | WO 01/79184 | 10/2001 |
| WO | WO 01/85686 | 11/2001 |
| WO | WO 01/85687 | 11/2001 |
| WO | WO 01/87845 | 11/2001 |
| WO | WO 01/90077 | 11/2001 |
| WO | WO 02/36576 | 5/2002 |
| WO | WO 02/44157 | 6/2002 |
| WO | WO 02/068407 | 9/2002 |
| WO | WO 02/090334 | 11/2002 |
| WO | WO 02/094790 | 11/2002 |
| WO | WO 03/007959 | 1/2003 |
| WO | WO 03/051879 | 6/2003 |
| WO | WO 03/055865 | 7/2003 |
| WO | WO 03/057145 | 7/2003 |
| WO | WO 03/063874 | 8/2003 |
| WO | WO 03/070707 | 8/2003 |

(56) References Cited

FOREIGN PATENT DOCUMENTS

| WO | WO 03/070726 | 8/2003 |
|---|---|---|
| WO | WO 03/080581 | 10/2003 |
| WO | WO 03/093261 | 11/2003 |
| WO | WO 2004/080976 | 9/2004 |
| WO | WO 2005/053662 | 6/2005 |

OTHER PUBLICATIONS

Ame et al., "The PARP Superfamily," Bioessays, 26:882-893 (2004).

Ang et al., "Efficacy of chemotherapy in BRCA1/2 mutation carrier ovarian cancer in the setting of poly(ADP-ribose) polymerase inhibitor resistance: a multi-institutional study," Clin Cancer Res, Aug. 6, 2013 [Epub ahead of print].

Ang et al., "Use of chemotherapy (CT) in BRCA1/2-deficient ovarian cancer (BDOC) patients (pts) with poly-ADP ribose polymerase inhibitor (PARPi) resistance: A multi-institutional study," ASCO, Chicago, IL, USA, Jun. 1-5, 2012, J. Clin. Oncol., 2012;30:15(Suppl):abst 5022.

Angell et al., "Consistent Gene Silencing in Transgenic Plants Expressing a Replicating Potato Virus X RNA," The EMBO Journal, 16(12):3675-3684 (1997).

Arnaudeau et al., "DNA Double-strand Breaks Associated with Replication Forks are Predominantly Repaired by Homologous Recombination Involving an Exchange Mechanism in Mammalian Cells," J. Mol. Biol., 307:1235-1245 (2001).

Audeh et al., "Oral poly(ADP-ribose) Polymerase Inhibitor in Patients with BRCA1 or BRCA2 Mutations and Recurrent Ovarian Cancer: a Proof-of-Concept Trial," www.thelancet.com, 376:245-251 (Jul. 24, 2010).

Audeh et al., "Oral poly(ADP-ribose) polymerase inhibitor olaparib in patients with BRCA1 or BRCA2 mutations and recurrent ovarian cancer: a proof-of-concept trial," Lancet, 376(9737): 245-251 (2010).

Audeh et al., "Phase II trial of the oral PARP inhibitor olaparib (AZD2281) in BRCA-deficient advanced ovarian cancer," ASCO, Orlando, FL, USA, May 2-Jun. 2, 2009, J Clin Oncol, 27(15S): abstract 5500 (2009).

Banasik et al., "Inhibitors and Activators of ADP-ribosylation Reactions," Molecular and Cellular Biochemistry, 138:185-197 (1994).

Banasik et al., "Specific Inhibitors of poly(ADP-ribose) Synthetase and mono(ADP-ribosyl) transferase," Journal of Biological Chemistry, 267(3):1569-1575 (1992).

Banker et al., "Modern Pharmaceutics," 3rd Ed., p. 596 (1996).

Benard et al., "FDG PET early metabolic response to the PARP inhibitor olaparib (AZD2281) in BRCA-deficient or recurrent high-grade ovarian carcinoma and BRCA-deficient or triple-negative breast cancer," Society of Nuclear Medicine, 59th Annual Meeting, Miami Beach, FL, USA, Jun. 9-13, 2012, J Nuclear Med, 53(Suppl 1): abstract 63 (2012).

Ben-Hur et al., "Inhibitors of poly(ADP-ribose) Synthesis Enhance Radiation Response by Differentially Affecting Repair of Potentially Lethal versus Sublethal Damage," British Journal of Cancer, 49(Suppl. VI):39-42 (1984).

Berge et al., "Pharmaceutical Salts," Journal of Pharmaceutical Sciences, 66(1):1-19 (1977).

Berger, "Symposium: Cellular Response to DNA Damage: The Role of poly(ADP-ribose)-Poly(ADP-ribose) in the Cellular Response to DNA Damage," Radiation Research, 101:4-15 (1985).

Bhattacharyya et al., "The Breast Cancer Susceptibility Gene BRCA1is Required for Subnuclear Assembly of Rad51 and Survival Treatment with the DNA Cross-linking Agent Cisplatin," Journal of Biological Chemistry, 275(31)23899-23903 (2000).

Bloch, et al. "Poly—adenosine diphosphate—ribose polymerase inhibition for myocardial protection: Pathophysiologic and physiologic considerations," Journal of Thoracic and Cardiovascular Surgery, Year 2004; 128:323-324.

Bold et al., "New Anilinophthalazines as Potent and Orally Well Absorbed Inhibitors of the VEGF Receptor Tyrosine Kinases Useful as Antagonists of Tumor-Driven Angiogenesis," J. Med. Chem., 43:2310-2323 (2000).

Bold et al., "New Anilinophthalazines as Potent and Orally Well Absorbed Inhibitors of the VEGF Receptor Tyrosine Kinases Useful as Antagonists of Tumor-Driven Angiogenesis," J. Med. Chem., 43:3200 (2000).

Bowman et al., "Differential Effects of the poly(ADP-ribose) Polymerase (PARP) Inhibitor NU1025 on Topoisomerase I and II Inhibitor Cytotoxicity in L1210 Cells in Vitro," British Journal of Cancer 84(1):106-112 (2001).

Brummelkamp et al., "A System for Stable Expression of Short Interfering RNAs in Mammalian Cells," Science, 296:550-553 (2002).

Bundgaard, "Design of Prodrugs," Elsevier Science Publishers (1985).

Bundred et al., "Evaluation of the pharmacodynamics and pharmacokinetics of the PARP inhibitor olaparib: a Phase I multicentre trial in patients scheduled for elective breast cancer surgery," Invest New Drugs, 31: 949-958 (2013).

Burzio et al., "Poly (Adenosine Diphosphoribose) Synthase Activity of Isolated Nuclei of Normal and Leukemic Leukocytes (38930)," Proceedings of the Society for Experimental Biology and Medicine, 149:933-938 (1975).

Calabrese, "Identification of Potent Nontoxic Poly(ADP-ribose) Polymerase-1 Inhibitors: Chemopotentiation and Pharmacological Studies," Clinical Cancer Research 9:2711-2718 (2003).

Caldecott, "DNA Single-strand Break Repair and Spinocerebellar Ataxia," Cell 112:7-10 (2003).

Cantoni et al., "Hydrogen Peroxide Insult in Cultured Mammalian Cells: Relationships Between DNA Single-strand Breakage, poly(ADP-ribose) Metabolism and Cell Killing," Biochimica et Biophysica Acta, 1014:1-7 (1989).

Catteau et al., "Methylation of the BRCA1 Promoter Region in Sporadic Breast and Ovarian Cancer: Correlation with Disease Characteristics," Oncogene 18:1957-1965 (1999).

Chalmers, "Poly(ADP-ribose) Polymerase-1 and Ionizing Radiation: Sensor, Signaller and Therapeutic Target," Clinical Oncology, 16:29-39 (2004).

Chappuis et al., "Risk Assessment and Genetic Testing," Cancer Treatment Research, 107:29-59 (2002).

Chiarugi, "Poly(ADP-ribose) Polymerase: Killer or Conspirator? The 'Suicide Hypothesis Revisited," TRENDS in Pharmaceutical Sciences, 23(3):122-129 (2002).

Cockcroft, et al. "Phthalazinones 2: Optimisation and synthesis of novel potent inhibitors of poly(ADP-ribose) polymerase," Bioorganic & Medicinal Chemistry Letters, Year Feb. 2006; 16(4):1040-1044.

Cosi et al., "Poly(ADP-ribose) Polymerase: Early Involvement in Glutamate-Induced Neurotoxicity in Cultured Cerebellar Granule Cells," Journal of Neuroscience Research, 39:38-46 (1994).

Cosi, "New Inhibitors of poly(ADP-ribose) Polymerase and their Potential Therapeutic Targets," Expert Opinion Ther. Patents, 12(7):1047-1071 (2002).

Couzin, "The Twists and Turns in BRCA's Path," Science 302:591-592 (2003).

Crook, "Therapeutic Applications of Oligonucleotides," Ann. Rev. Pharmacol. Toxicol., 32:239-376 (1992).

Cuzzocrea, "Shock, inflammation and PARP," Pharmacological Research, Year Jul. 2005; 52(1):72-82.

D'Adda di Fagagna et al., "Functions of poly(ADP-ribose) Polymerase in Controlling Telomere Length and Chromosomal Stability," Nature Genetics 23(1):76-80 (1992).

D'Amours et al., "Poly(ADP-ribosyl)ation Reactions in the Regulation of Nuclear Functions," Biochem. J., 342:249-268 (1999).

D'Amours et al., "The MRE11 Complex: At the Crossroads of DNA Repair and Checkpoint Signalling," Nature Reviews, Molecular Biology, 3:317-327 (2002).

D'Andrea et al., "The Fanconi Anaemia/BRCA Pathway," Nature Reviews, Cancer, 3:23-34 (2003).

Dantzer et al., "Base Excision Repair is Impaired in Mammalian Cells Lacking poly(ADP-ribose) Polymemse-1," Biochemistry 39:7559-7569 (2000).

(56) References Cited

OTHER PUBLICATIONS

Dantzer et al., "Involvement of poly(ADP-ribose) Polymerase in Base Excision Repair," Biochimie 81:69-75 (1999).
Davies et al., "Role of BRCA2 in Control of the RAD51 Recombination and DNA Repair Protein," Molecular Cell, 7:273-282 (2001).
Dillon et al., "A FlashPlate Assay for the Identification of PARP-1 Inhibitors," J. Biomolecular Screening, 8(3):347-352 (2003).
Dougherty et al., "Next generation sequencing and oncology translational medicine: a case study in Olaparib-treated serous ovarian cancer patients," AstraZeneca poster, Keystone Symposium: Human Genomics and Personalized Medicine (E3), Stockholm, Sweden, Jun. 17-21, 2013.
Drew et al., "PARP Inhibitors in Cancer Therapy: Two Modes of Attack on the Cancer Cell Widening Clinical Applications," Drug Resistance Updates, 12:153-156 (2009).
Durkacz et al., "(ADP-ribose)participates in DNA Excision Repair," Nature, 283(7):593-596 (1980).
Dusemund, "Einfache Synthese von Isochino [2,3c][2,3]benzoxazepinon und -[2,3]benzodiazepinonen sowie ihrer Vorstufen," Arch. Pharm. (Weinheim), 321:41-44 (1988).
Dusemund, "Isochino[3,2-a]phthalazin-5,8-dione," Arch. Pharm. (Weinheim), 315:925-930 (1982).
Egawa et al., "Decreased Expression of BRCA2 mRNA Predicts Favorable Response to Docetaxel in Breast Cancer," Int. J. Cancer (Pred. Oncol.), 95:255-259 (2001).
Egawa et al., "Quantitative Analysis of Estrogen Receptor-α and -β Messenger RNA Expression in Normal and Malignant Thyroid Tissues by Real-Time Polymerase Chain Reaction," Oncology, 61:293-298 (2001).
Ehrlich et al., "Recent Advances in the Polymerase Chain Reaction," Science, 252:1643-1650 (1991).
Elbashir et al., "Duplexes of 21-Nucleotide RNAs Mediate RNA Interference in Cultured Mammalian Cells," Nature, 411:494-498 (2001).
El-Tamaty et al., "Synthesis and Biological Activity of Some 4-benzyl-1(2H)-phthalazinone Derivatives," Chemical Abstracts, 125(23):300924j (1996).
El-Tamaty et al., "Synthesis and Biological Activity of Some 4-benzyl-1(2H)-phthalazinone Derivatives," Indian Journal of Chemistry, 35B:1067-1072 (1996).
Esteller et al., "Promoter Hypermethylation and BRCA1 Inactivation in Sporadic Breast and Ovarian Tumors," Journal of the National Cancer Institute, 92(7):564-569 (2000).
Ferraris et al., "Design and Synthesis of Poly ADP-ribose Polymerase-1Inhibitors. 2. Biological Evaluation of Aza-5[H]-phenanthridin-6-ones as Potent, Aqueous-Soluble Compounds for Treatment of Ischemic Injuries," J. Med. Chem., 46:3138-3151 (2003).
Fire et al., "Potent and Specific Genetic Interference by Double-stranded RNA in Caenorhabditis elegans," Nature, 391:806-811 (1998).
Fong et al., "Inhibition of Poly(ADP-Ribose) Polymerase in Tumors from BRCA Mutation Carriers," New England Journal of Medicine; Year Jul. 9, 2009; 361(2):123-134.
Foray et al., "A Subset of ATM- and ATR-dependent Phosphorylation Events Requires the BRCA1 Protein," EMBO Journal, 22(11):2860-2871 (2003).
Fujisawa Pharmaceutical Co., "Preparation of 2-carboxyalkyl-4-aralkylphthalazine Derivatives as Aldose Reductase Inhibitors and a Process for Preparing Them," Chemical Abstracts 109:6531.
Fuska et al., "New Cytotoxic and Antitumor Agents," Chemical Abstracts, 104:102050 (1985).
Gaken et al., "Efficient Retroviral Infection of Mammalian Cells is Blocked by Inhibition of Poly(ADP-Ribose) Polymerase Activity," Journal of Virology, 70(6):3992-4000 (1996).
Gelmon et al., "Can we define tumors that will respond to PARP inhibitors? a phase II correlative study of olaparib in advanced serous ovarian cancer and triple negative breast cancer," ASCO, Chicago, IL, USA, Jun. 4-8, 2010, J Clin Oncol, 28(7S): 3002(Abstract) (2010).
Gelmon et al., "Olaparib in patients with recurrent high-grade serous or poorly differentiated ovarian carcinoma or triple-negative breast cancer: a Phase 2, multicentre, open-label, non-randomised study," Lancet Oncol, 12(9): 852-861 (2011).
Gelmon et al., "Sas 4—Can we define tumors that will respond to PARP inhibitors? A phase II correlative study of olaparib in advanced serous ovarian cancer and triple negative breast cancer," The 2011 Annual Meeting on Women's Cancer™, Society of Gynecological Oncologists, Mar. 6-9, 2011, Abstract SAS 4, pp. 23 and 24.
Gien et al., "The Emerging Role of PARP Inhibitors in the Treatment of Epithelial Ovarian Cancer," Journal of Oncology, 2010:1-6 (2010).
Greene, T.W. et al., "Protective Groups in Organic Synthesis," Chapters 2 and 7, John Wiley & Sons Inc. (1999) p. 17-23 and 494-503.
Griffin et al., "Mammalian Recombination-repair Genes XRCC2 and XRCC3 Promote Correct Chromosome Segregation," Nature Cell Biology, 2:757-761 (2000).
Griffin et al., "the Role of Inhibitors of poly(ADP-ribose) Polymerase as Resistance-modifying in Cancer Therapy," Biochimie, 77:408-422 (1995).
Grube et al., "Direct Stimulation of Poly(ADP Ribose) Polymerase in Permeabilized Cells by Double-stranded DNA Oligomers," Analytical Biochemistry, 193:236-239 (1991).
Haber, "DNA Recombination: The Replication Connection," Trends Biochem. Sci., 24:271-275 (1999).
Hall et al., "Cytotoxicity of imides-N-alkyl Semicarbazones, Thiosemicarbazones, Acetylhydrazones and Related Derivatives," Anti-Cancer Drugs, 6:147-153 (1995).
Halldorsson et al., "Poly(ADP-ribose) Polymerase Activity in Nucleotide Permeable Cells," FEBS Letters, 85(2):349-352 (1978).
Hay et al., "Poly(ADP-Ribose) Polymerase-1 Inhibitor Treatment Regresses Autochthonous Brca2/p53-Mutant Mammary Tumors In vivo and Delays Tumor Relapse in Combination with Carboplatin," Cancer Research, Year May 1, 2009; 69(9):3850-3855.
Herceg et al., "Functions of poly(ADP-ribose) Polymerase (PARP) in DNA Repair, Genomic Integrity and Cell Death," Mutation Research, 477:97-110 (2001).
Hirai et al., "Aberration of Poly(Adenosine Dephosphate-Ribose) Metabolism in Human Colon Adenomatous Polyps and Cancers," Cancer Research, 43:3441-3446 (1983).
Hiramoto et al., "Mutations of Novel Human RAD54 Homologue, RAD54B, in Primary Cancer," Oncogene 18:3422-3426 (1999).
Hoeijmakers, "Genome Maintenance Mechanisms for Preventing Cancer," Nature, 411:366-374 (2001).
Hughes-Davies et al., "EMSY Links in BRCA2 Pathway to Sporadic Breast and Ovarian Cancer," Cell, 115:523-535 (2003).
Islam et al., "4,5,6,7-Tetraiodo-3-benzalphthalides and Related Compounds," Chemical Abstracts, 95:187182 (1981).
Islam et al., "Action of Phosphorus Pentasulfide on the Products of Interaction of p-sulfamoylphenylacetic Acids with Phthalic Anhydride," Chemical Abstracts, 95:62106 (1981).
Islam et al., "Thioarylidenephthalides and Related Compounds: Part II. Reactions with Amino Compounds," Chemical Abstracts, 87:67943 (1977).
Jackson, "Sensing and Repairing DNA Double-strand Breaks," Carcinogenesis, 23(5):687-696 (2002).
Janatova et al., "Detection of the Most Frequent Mutations in BRCA1 Gene on Polyacrylamide Gels Containing Spreadex Polymer NAB," Neoplasma, 50(4):246-250 (2003).
Jancarkova et al., "Detection and Incidence of Mutations of BRCA1 Gene in Patients with Cancer of the Breast and Ovary," Ceska Gynekol, 68(1):11-16 (2003).
Jantzen et al., "B. Prodrugs," taken from Modern Pharmaceutics, Third Edition, Banker and Rhodes, editors (1996) p. 596.
Jasin, "Homologous Repair of DNA Damage and Tumorigenesis: The BRCA Connection," Oncogene, 21:8981-8993 (2002).

(56) References Cited

OTHER PUBLICATIONS

Jijon et al., "Inhibition of poly(ADP-ribose) Polymerase Attenuates Inflammation in a Model of Chronic Colitis," Am. J. Physiol. Gastrointest. Liver Physiol., 279:G641-G651 (2000).
Johnson et al., "Mammalian XRCC2 Promotes the Repair of DNA Double-strand Breaks by Homologous Recombination," Nature, 401:397-399 (1999).
Kanaar et al., "Molecular Mechanisms of DNA Double-strand Break Repair," Trends in Cell Biology, 8:483-489 (1998).
Kashani-Sabet et al., "Application of Ribozymes to Cancer Gene Therapy," Cancer Gene Therapy, 2(3):213-223 (1995).
Kaufman et al., "Olaparib monotherapy in patients with advanced cancer and a germline BRCA1/2 mutation: An open-label phase II study," ASCO, Chicago, IL, USA, May 31-Jun. 4, 2013, J Clin Oncol, 31(15 Suppl): abstract 11024 (2013).
Kawamura et al., "Ponalrestat, an Aldose Reductase Inhibitor," Chemical Abstracts, 132:273943 (1999).
Kaye et al., "Phase II, open-label, randomized, multicenter study comparing the efficacy and safety of olaparib, a poly (ADP-ribose) polymerase inhibitor, and pegylated liposomal doxorubicin in patients with BRCA1 or BRCA2 mutations and recurrent ovarian cancer," J Clin Oncol, 30(4):372-379 (2012).
Kerr et al., "New Complexities for BRCA1 and BRCA2," Curr. Biol., 11:R668-R676 (2001).
Kerrigan et al., Poster at 12th SCI-RSC Medicinal Chemistry Symposium, Cambridge, 7-10 (2003).
Khanna et al., "DNA Double-strand Breaks: Signaling, Repair and the Cancer Connection," Nature, 27(3):247-254 (2001).
Kraakman-van der Zwet et al., "Brca2 (XRCC11) Deficiency Results in Radioresistant DNA Synthesis and a Higher Frequency of Spontaneous Deletions," Molecular and Cellular Biology, 22(2):669-679 (2002).
Kuperstein et al., "A Rapid Fluorescent Multiplexed-PCR Analysis (FMPA) for Founder Mutations in the BRCA1 and BRCA2 Genes," Clin. Genet., 57:213-220 (2000).
Kupper et al., "Trans-Dominant Inhibition of Poly(ADP-ribosyl)ation Potentiates Carcinogen-induced Gene Amplification in SV40-transformed Chinese Hamster Cells," Cancer Research, 56:2715-2717 (1996).
Lakhani et al., "The Pathology of Familial Breast Cancer: Predictive Value of Immunohistochemical Markers Estrogen Receptor, Progesterone Receptor, HER-2, and p53 in Patients with Mutations in BRCA1 and BRCA2," Journal of Clinical Oncology, 20(9):2310-2318 (2002).
Le Rhun et al., "Cellular Responses to DNA Damage in the Absence of Poly(ADP-ribose) Polymerase," Biochemical and Biophysical Research Communications, 245:1-10 (1998).
Ledermann et al., "Olaparib maintenance therapy in patients with platinum-sensitive relapsed serous ovarian cancer (SOC) and a BRCA mutation (BRCAm)," ASCO, Chicago, IL, May 31-Jun. 4, 2013, J. Clin. Oncol., 2013;31(15 Suppl):abst 5505.
Ledermann et al., "Olaparib maintenance therapy in platinum-sensitive relapsed ovarian cancer," N Engl J Med, 366:1382-1392 (2012).
Ledermann et al., "Phase 2 randomized placebo-controlled study of olaparib (AZD2281) in patients with platinum-sensitive relapsed serous ovarian cancer (PSR SOC)," Abstract, 43rd SGO Meeting, Austin, TX, Mar. 24-27, 2012.
Ledermann et al., "Phase 2 randomized placebo-controlled study of olaparib (AZD2281) in patients with platinum-sensitive relapsed serous ovarian cancer (PSR SOC)," Society of Gynecologic Oncologists (SGO), 43rd Annual Meeting on Women's Cancer, Austin, TX, USA, Mar. 24-27, 2012.
Ledermann et al., "Phase II randomized placebo-controlled study of olaparib (AZD2281) in patients with platinum-sensitive relapsed serous ovarian cancer (PSR SOC)," ASCO, Chicago, USA, Jun. 3-7, 2011, J. Clin. Oncol., 2011; 29(Suppl):abst 5003.
Ledermann et al., "Phase II randomized placebo-controlled study of olaparib (AZD2281) in patients with platinum-sensitive relapsed serous ovarian cancer (PSR SOC)," ASH, San Diego, CA, USA, Dec. 10, 2011, Blood 2012.
Ledermann et al., "Phase II randomized placebo-controlled study of olaparib (AZD2281) in patients with platinum-sensitive relapsed serous ovarian cancer (PSR SOC)," ESGO, Milan, Italy, Sep. 11-14, 2011, Int. J. Gyn. Cancer, 2011;21(Suppl):abst 1370.
Ledermann et al., "Phase II randomized placebo-controlled study of olaparib (AZD2281) in patients with platinum-sensitive relapsed serous ovarian cancer," Asian Society of Gynecologic Oncology (ASGO) 2nd Biennial Meeting, Seoul, Korea, Nov. 4-5, 2011.
Lemay et al., "Detection of DNA Damage and Identification of UV-Induced Photoproducts Using the CometAssay™ Kit," BioTechniques, 27:846-851 (1999).
Liaudet et al., "Protection Against Hemorrhagic Shock in Mice Genetically Deficient in poly(ADP-ribose)polymerase," Proc. Natl. Acad. Sci. U.S.A., 97(18):10203-10208 (2000).
Lindahl et al., "Post-translational Modification of poly(ADP-ribose) Polymerase Induced by DNA Strand Breaks," Trends Biochem. Sci., 20:405-411 (1995).
Lindahl, et al., "Quality Control by DNA Repair," Science, 286:1897-1905 (1999).
Loh, et al., "Phthalazinones. Part 1: The design and synthesis of a novel series of potent inhibitors of poly(ADP-ribose) polymerase," Bioorganic & Medicinal Chemistry Letters, Year May 2, 2005; 15(9):2235-2238.
Lundin et al., "Different Roles for Nonhomologous End Joining and Homologous Recombination following Replication Arrest in Mammalian Cells," Molecular and Cellular Biology, 22(16):5869-5878 (2002).
Lundin et al., "RAD51 is Involved in Repair of Damage Associated with DNA Replication in Mammalian Cells," J. Mol. Biol., 328:521-535 (2003).
Magnusson et al., "Inhibitor of poly(ADP-ribose)transferase Potentiates the Recombinogenic but not the Mutagenic Action of Alkylating Agents in Somatic Cells in vivo in Drosophila melanogaster," Mutagenesis, 5(5):511-514 (1990).
Martin et al., "Phthalazinone Derivatives as Potent PARP-1 Inhibitors," 13th Symposium on ADP-ribosylation, Abstract 107 (2001).
Martin, "DNA Repair Inhibition and Cancer Therapy," Journal of Photochemistry and Photobiology B: Biology, 63:162-170 (2001).
Matsuda et al., "Mutations in the RAD54 Recombination Gene in Primary Cancers," Oncogene, 18:3427-3430 (1999).
McCabe et al., "Deficiency in the Repair of DNA Damage by Homologous Recombination and Sensitivity to Poly(ADP-Ribose) Polymerase Inhibition," Cancer Res, 66(16): 8109-8115 (2006).
McMahon, "VEGF Receptor Signaling in Tumor Angiogenesis," The Oncologist, 5(Suppl 1):3-10 (2005).
McNealy et al., "Intrinsic Presence of Poly (ADP-ribose) is Significantly Increased in Malignant Prostate Compared to Benign Prostate Cell Lines," Anticancer Research, 23:1473-1478 (2003).
Menear, et al., "4-[3-(4-Cyclopropanecarbonylpiperazine-1-carbonyl)-4-fluorobenzyl]-2H-phthalazin-1-one: A Novel Bioavailable Inhibitor of Poly (ADP-ribose) Polymerase-1," Journal of Medicinal Chemistry, Year Oct. 23, 2008, 51(20):6581-6591 (published on Web Sep. 19, 2008).
Menissier de Murcia et al., "Functional Interaction Between PARP-1 and PARP-2 in Chromosome Stability and Embryonic Development in Mouse," EMBO J., 22(9):2255-2263 (2003).
Menissier de Murcia et al., "Requirement of poly(ADP-ribose) Polymerase in Recovery From DNA Damage in Mice and Cells," Proc. Natl. Acad. Sci. U.S.A., 94:7303-7307 (1997).
Mercola et al., "Antisense Approaches to Cancer Gene Therapy," Cancer Gene Therapy, 2(1):47-59 (1995).
Miller, "Inhibition of TRPM2 function by PARP inhibitors protects cells from oxidative stress-induced death," British Journal of Pharmacology, Year 2004; 143:515-516.
Miwa et al., "Cell Density-dependent Increase in Chromatin-associated Adp-Ribosyltransferase Activity in Simian Virus 40-Transformed Cells," Archives of Biochemistry and Biophysics, 181:313-321 (1977).

(56) References Cited

OTHER PUBLICATIONS

Molife et al., "Safety and efficacy results from two randomized expansions of a Phase I study of a tablet formulation of the PARP inhibitor, olaparib, in ovarian and breast cancer patients with BRCA1/2 mutations," ASCO, Chicago, IL, USA, Jun. 1-5, 2012, J Clin Oncol, 30:15(Suppl): abstract 3048 (2012).

Morrison et al., "Genetic Interaction between PARP and DNA-PK in V(D)J Recombination and Tumorigenesis," Nature Genetics, 17:479-482 (1997).

Moynahan et al., "Brca1 Controls Homology-directed DNA Repair," Molecular Cell., 4:511-518 (1999).

Moynahan et al., "BRCA2 is Required for Homology-directed Repair of Chromosomal Breaks," Molecular Cell., 7:263-272 (2001).

Mullis et al., "Specific Enzymatic Amplification of DNA in Vitro: The Polymerase Chain Reaction," Cold Spring Harbor Symp. Quant. Biol., 51:263-273 (1987).

Nakamura et al., "Quantitation of Intracellular NAD(P)H can Monitor an Imbalance of DNA Single Strand Break Repair in Base Excision Repair Deficient Cells in Real Time," Nucleic Acids Research, 31(17):e104 (2003).

Nathanson et al., "Breast Cancer Genetics: What We Know and What We Need," Nature Medicine, 7(5):552-556 (2001).

Neuhausen et al., "Mutation Testing of Early-Onset Breast Cancer Genes BRCA1 and BRCA2," Genetic Testing, 1(2):75-83 (1997).

Noel et al., "Poly(ADP-ribose) polymerase (PARP-1) is not Involved in DNA Double-strand Break Recovery," BMC Cell Biol., 4:7-17 (2003).

Olaparib (Code C71721), National Cancer Institute, version 13.07e (Release date: Jul. 29, 2013).

Oza et al., "A phase II trial demonstrating activity of single agent olaparib (AZD2281) in women with recurrent serous ovarian carcinoma," IGCS 2010, Prague, Czech Republic, Oct. 23-26, 2010, Abstract #856.

Pacher et al., "The Role of Poly(ADP-ribose) Polymerase Activation in the Development of Myocardial and Endothelial Dysfunction in Diabetes," Diabetes, 51:514-521 (2002).

Perkins et al., "Novel Inhibitors of Poly(ADP-ribose) Polymerase/ PARP1 and PARP2 Identified Using a Cell-based Screen in Yeast," Cancer Research, 61:4175-4183 (2001).

Pierce et al., "XRCC3 Promotes Homology-directed Repair of DNA Damage in Mammalian Cells," Genes & Development, 13:2633-2638 (1999).

Pinedo et al., "Translational Research: The Role of VEGF in Tumor Angiogenesis," The Oncologist, 5:(Suppl 1):1-2 (2000).

Radice, "Mutations of BRCA Genes in Hereditary Breast and Ovarian Cancer," J. Exp. Clin. Cancer Res., 21(Suppl 3):9-12 (2002).

Rattan et al., "Kinetin Delays the Onset of Ageing Characteristics in Human Fibroblasts," Biochemical and Biophysical Research Communications, 201(2):665-672 (1994).

Said et al., "Excitotoxicity in the Lung: N-Methyl-D-aspartate-induced, Nitric Oxide-dependent, Pulmonary Edema is attenuated by Vasoactive Intestinal Peptide and by Inhibitors of poly(ADP-ribose) Polymerase," Proc. Natl. Acad. Sci. U.S.A., 93:4688-4692 (1996).

Samper et al., "Normal Telomere Length and Chromosomal End Capping in poly(ADP-ribose) Polymerase-deficient Mice and Primary Cells Despite Increased Chromosomal Instability," Journal of Cell Biology, 154(1):49-60 (2001).

Sandhu, S. K. et al., "Poly (ADP-ribose) polymerase (PARP) inhibitors for the treatment of advanced germline BRCA2 mutant prostate cancer," Annals of Oncology, 2013, vol. 24, No. 5, 1416-1418.

Satoh et al., "Role of poly(ADP-ribose) Formation in DNA Repair," Nature, 356:356-358 (1992).

Schlicker et al., "4-Amino-1,8-naphthalimide: A Novel Inhibitor of poly(ADP-ribose) Polymerase and Radiation Sensitizer," Int. J. Radiat. Biol., 75(1):91-100 (1999).

Schreiber et al., "A Dominant-negative Mutant of Human poly(ADP-ribose) Polymerase Affects Cell Recovery, Apoptosis, and Sister Chromatid Exchange Following DNA Damage," Proc. Natl. Acad. Sci. U.S.A., 92:4753-4757 (1995).

Schreiber et al., "Poly(ADP-ribose) Polymerase-2 (PARP-2) is Required for Efficient Base Excision DNA Repair in Association with PARP-1 and XRCC1," Journal of Biological Chemistry, 277(25):23028-23036 (2002).

Schultz et al., "Poly(ADP-ribose) Polymerase (PARP-1) has a Controlling Role in Homologous Recombination," Nucleic Acids Research, 31(17):4959-4964 (2003).

Semionov et al., "Inhibition of poly(ADP-ribose)polymerase Stimulates Extrachromosomal Homologous Recombination in Mouse Ltk- Fibroblasts," Nucleic Acids Research, 27(22):4526-4531 (1999).

Shah et al., "Complete Inhibition of poly(ADP-ribose) Polymerase Activity Prevents the Recovery of C3H10T1/2 Cells from Oxidative Stress," Biochimica et Biophysica Acta, 1312:1-7 (1996).

Shall et al., "Poly(ADP-ribose) Polymerase-1: What have We Learned from the Deficient Mouse Model?," Mutation Research, 460:1-15 (2000).

Shapira-Frommer et al., "Olaparib treatment for platinum-resistant recurrent ovarian cancer: BRCA mutation carriers—a single institution experience, Israel Society for Clinical Oncology and Radiation Therapy (ISCORT)," Eilat, Israel, Jan. 10-12, 2012, [abst 1201].

Shapira-Frommer, "Iceberg 42: open-label, multicenter, phase 2 study of olaparib in germline BRCA1/2 mutation carriers (NCT01078662)," Care conference, Israel, Nov. 4, 2011.

Shimizu et al., "Inhibitory Effects of Azelastine and Tranilast on Leukotriene B4 and Leukotriene C4 Generation by Rat Colonic Mucosa," Prostaglandins Leukotrienes and Essential Fatty Acids, 53:355-358 (1995).

Silverman, "The Organic Chemistry of Drug Design and Drug Action," Academic Press, 352-400 (1992).

Simbulan-Rosanthal, et al., "Chromosomal Aberrations in PARP-/- Mice: Genome Stabilization in Immortalized Cells by Reintroduction of poly(ADP-ribose) Polymerase cDNA," Proc. Natl. Acad. Sci. U.S.A., 96(23):13191-13196 (1999).

Skehan et al., "New Colorimetric Cytotoxicity Assay for Anticancer-Drug Screening," Journal of the National Cancer Institute, 82(3):1107-1112 (1990).

Southan et al., "Poly(ADP-ribose) Polymerase Inhibitors," Current Medicinal Chemistry, 12:321-340 (2003).

Suto et al., Dihydroisoquinolinones: The Design and Synthesis of a New Series of Potent Inhibitors of poly(ADP-ribose) Polymerase, Anti-Cancer Drug Design, 6(2):107-117 (1991).

Szabo et al., "Endothelial Dysfunction in a Rat Model of Endotoxic Shock," J. Clin. Invest., 100(3):723-735 (1997).

Szabo, "Role of Poly(ADP-Ribose) Polymerase Activation in the Pathogenesis of Shock and Inflammation," PARP as a Therapeutic Target, Ed. Zhang, CRC Press, 169-204 (2002).

Szabó, et al., "Poly-ADP-ribose polymerase inhibition protects against myocardial and endothelial reperfusion injury after hypothermic cardiac arrest," Journal of Thoracic and Cardiovascular Surgery, Year 2003; 126:651-658.

Taniguchi et al., "Disruption of the Faconi Anemia-BRCA Pathway in Cisplatin-sensitive Ovarian Tumors," Nature Medicine, 9(5):568-574 (2003).

Tarsounas et al., "BRCA2-dependent and Independent Formation of the RAD51 Nuclear Foci," Oncogene, 22:1115-1123 (2003).

Tasatargil, et al., "Poly(ADP-Ribose) Polymemse Inhibition Prevents Homocysteine-Induced Endothelial Dysfunction in the Isolated Rat Aorta," Pharmacology International Journal of Experimental and Clinical Pharmacology, Year 2004; 72:99-105.

Tebbs et al., "Correction of Chromosomal Instability and Sensitivity to Diverse Mutagens by a Cloned cDNA of the XRCC3 DNA Repair Gene," Proc. Natl. Acad. Sci. U.S.A., 92:6354-6358 (1995).

Tentori et al., "Potential Clinical Applications of poly(ADP-ribose) Polymerase (PARP) Inhibitors," Pharmacological Research, 45(2):73-85 (2002).

Thompson et al., "Recombinational DNA Repair and Human Disease," Mutation Research, 509:49-78 (2002).

(56) References Cited

OTHER PUBLICATIONS

Tracey et al., "Aldose Reductase Inhibition alone or Combined with an Adenosine A3 Agonist Reduces Ischemic Myocardial Injury," Chemical Abstracts, 134:65983 (2000).
Tutt et al., "Disruption of Brca2 Increases the Spontaneous Mutation Rate in vivo: Synergism with Ionizing Radiation," EMBO Reports, 31(31):255-260 (2002).
Tutt et al., "Mutation in Brca2 Stimulates Error-prone Homology-directed Repair of DNA Double-strand Breaks Occurring Between Repeated Sequences," EMBO Journal, 20(17):4704-4716 (2001).
Tutt et al., "Oral poly(ADP-ribose) Polymemse Inhibitor Olaparib in Patients with BRCA1 or BRCA2 Mutations and Advanced Breast Cancer: A Proof-of-concept Trial," www.thelancet.com, 376:235-244 (2010).
Tutt et al., "The Relationship Between the Roles of BRCA Genes in DNA Repair and Cancer Predisposition," TRENDS in Molecular Medicine, 18(12):571-576 (2002).
Tutt et al., "Oral poly(ADP-ribose) polymerase inhibitor olaparib in patients with BRCA1 or BRCA2 mutations and advanced breast cancer: a proof-of-concept trial," Lancet., 376(9737):235-244 (2010).
Tutt et al., "Phase II trial of the oral PARP inhibitor olaparib in BRCA-deficient advanced breast cancer," ASCO, Orlando, FL, USA, May 29-Jun. 2009, J Clin Oncol, 27(18S): abstract CRA501 (2009).
Tutt, Phase II trial of the oral PARP inhibitor olaparib in BRCA-deficient advanced breast cancer. NCRI. Birmingham, UK, Oct. 4-7, 2009.
Uhlmann et al., "Antisense Oligonucleotides: A New Therapeutic Principle," Chemical Reviews, 90(4):543-584 (1990).
van Gent et al., "Chromosomal Stability and the DNA Double-stranded Break Connection," Nature Reviews Genetics, 2:196-206 (2001).
Venkitaraman et al., "Cancer Susceptibility and the Functions of BRCA1 and BRCA2," Cell, 108:171-182 (2002).
Vippagunta, S.R. et al., "Crystalline solids," Adv. Drug Delivery Reviews (2001) 48:3-26.
Virag et al., "The Therapeutic Potential of Poly(ADP-ribose) Polymerase Inhibitors," Pharmacological Reviews, 54(3):375-429 (2002).
Voinnet et al., "Systemic Signalling in Gene Silencing," Nature, 389:553 (1997).
Waldman et al., "Stimulation of Intrachromosomal Homologous Recombination in Mammalian Cells by an Inhibitor of poly(ADP-ribosylation)," Nucleic Acids Research, 19(21):5943-5947 (1991).
Wang et al., "Mice Lacking ADPRT and poly(ADP-ribosyl)ation Develop Normally but are Susceptible to Skin Disease," Genes & Development, 9:509-520 (1995).
Wang et al., "PARP is Important for Genomic Stability but Dispensable in Apoptosis," Genes & Development, 11:2347-2358 (1997).
West, "Solid State Chemistry and its Applications," Wiley, New York, pp. 358 and 365 (1988).
Wood et al., "Human DNA Repair Genes," Science, 291:1284-1289 (2001).
Yamaguchi, "Novel Antiasthmatic Agents with Dual Activities of Thromboxane A2 Synthetase Inhibition and Bronchodilation. 1. 2-[2(1-Imidazoly)alkyl]-(2H)-phthalazinones," J. Med. Chem., 36(25):4052-4060 (1993).
Yamaguchi, "Novel Antiasthmatic Agents with Dual Activities of Thromboxane A2 Synthetase Inhibition and Bronchodilation. 2. 4-(3-Pyridyl)-1(2H)-phthalazinones," J. Med. Chem., 36(25):4061-4068 (1993).
Zamore et al., "RNAi: Double-Stranded RNA Directs the ATP-Dependent Cleavage of mRNA at 21 to 23 Nucleotide Intervals," Cell, 101:25-33 (2000).
Zamore, "RNA Interference: Listening to the Sounds of Silence," Nature Structural Biology, 8(9):746-750 (2000).
Zhang et al., "Neuroprotective Effects of Poly(ADP-ribose) Polymerase Inhibition on Focal Cerebral Ischemia," Portland Press Proc., 15:125 (1998).
Zhong et al., "Association of BRCA1 with the hRad50-hMre11-p95 Complex and the DNA Damage Response," Science, 285:747-750 (1999).
Zingarelli et al., "Activator Protein-1 Signalling Pathway and Apoptosis are Modulated by poly(ADP-ribose) Polymerase-1 in Experimental Colitis," Immunology, 113:509-517 (2004).
McMahon et al. (2000).
Chen et al; Cancer Letters, vol. 348, Issues 1-2, Jun. 28-Jul. 1, 2014, pp. 20-28.
Bendell, et al., Ann Oncol (2015), 26(4): 804-811.
Lowery et al, J Clin Oncology, 2014, Asco e15237.
Kaufman, B., et al., JCO, Jan. 20, 2015, vol. 33, No. 3, 244-250.
Kindler, et al., J Clin Oncol 33, 2015 (suppl; abstr TPS4149) (abstract and poster).
Deeks, E., Drugs, Feb. 2015, 75(2), 231-240.
Bhalla and Saif: Journal of the Pancreas—http://www.serena.unina.it/index.php/jop—vol. 15, No. 4, Jul. 2014, 340-343.
Clarke et al. Olaparib combined with abiraterone in patients with metastatic prostate cancer: Safety run-in from a phase II study. J Clin Oncol 33, 2015 (suppl; abstr e16026).
Mateo et al. DNA-Repair Defects and Olaparib in Metastatic Prostate Cancer. N Engl J Med 2015; 373:1697-1708.
Mateo et al. Antitumour activity of the PARP inhibitor olaparib in unselected sporadic castration-resistant prostate cancer (CRPC) in the TOPARP trial; ESMO 2014 (abstract and presentation).
Mateo et al. TPPARP: Phase II trial of the PARP inhibitor olaparib in sporadic and unselected metastatic Castration Resistant Prostate Cancer (mCRPC). AACR 2015 (abstract and presentation).
Notice of Allowance issued Feb. 4, 2008, in U.S. Appl. No. 10/876,080.
Notice of Allowance issued Jun. 11, 2009, in U.S. Appl. No. 11/318,155.
Notice of Allowance issued Mar. 7, 2011, in U.S. Appl. No. 12/109,260.
Office Action issued Feb. 22, 2006, in U.S. Appl. No. 10/876,080.
Office Action issued Jan. 26, 2009, in U.S. Appl. No. 11/318,155.
Office Action issued Jan. 5, 2007, in U.S. Appl. No. 10/876,080.
Office Action issued Jul. 11, 2008, in U.S. Appl. No. 11/318,155.
Office Action issued Jul. 12, 2006, in U.S. Appl. No. 10/876,080.
Office Action issued Jun. 10, 2010, in U.S. Appl. No. 12/109,260.
Office Action issued Jun. 23, 2005, in U.S. Appl. No. 10/876,080.
Office Action issued Mar. 17, 2008, in U.S. Appl. No. 11/318,155.
Office Action issued Nov. 21, 2005, in U.S. Appl. No. 10/876,080.
Office Action issued Oct. 21, 2010, in U.S. Appl. No. 12/109,260.
Office Action issued Oct. 4, 2007, in U.S. Appl. No. 10/876,080.
United States Patent Office Action for U.S. Appl. No. 14/483,663 dated Oct. 17, 2014 (12 pages).
United States Patent Office Notice of Allowance for U.S. Appl. No. 14/483,663 dated Jun. 8, 2015 (7 pages).
Bornstein, E. et al., "Olaparib for the treatment of ovarian cancer," Drugs of Today (2016) 52(1):17-28.
Chand, S.N. et al., Abstract 5476: "A novel PARP inhibitor resistance mechanism mediated by the RNA-binding protein HuR," Proceedings of the 106th Annual Meetnig of the American Association for Cancer Research (2015) Philadelphia, PA; AACR, Cancer Res. (2015) 75(15Supp): Abstract No. 5476.
Dhillon, K.K. et al., "Resistance to PARP inhibitors mediated by secondary BRCA1/2 mutations," Chapter 18 of Divisions of Human Biology and Public Health Sciences, Fred Hutchinson Cancer Research Center, Seattle, WA (2015) 431-452.
Karnak, D. et al., "Combined inhibition of Wee1 and PARP1/2 for radiosensitization in pancreatic cancer," Clin. Cancer Res. (2014) 20(19):5085-5096.
Lee, J-M. et al., "PARP inhibitors for BRCA1/2 mutation-associated and BRCA-like malignancies," Annals of Oncology (2014) 25:32-40.
Martinez-Bosch, N. et al., "Poly(ADP-ribose) polymnerases. New players in the pathogenesis of exocrine pancreatic diseases," Amer. J. Pathology (2016) 186(2):234-241.

(56) References Cited

OTHER PUBLICATIONS

Singh, S.S. et al., "A review on PARP1 inhibitors: pharmacophore modeling, virtual and biological screening studies to identify novel PARP1 inhibitors," Curr. Topics in Med. Chem. (2014) 14:2020-2030.

Sociali, G. et al., "Quinazolinedione SIRT6 inhibitors sensitize cancer cells to chemotherapeutics," Eur. J. Med. Chem. (2015) 102:530-539.

Tangutoori, S. et al., "PARP inhibitors: a new era of targeted therapy," Maturitas (2015) 81:5-9.

Vance, S.M. et al., "Selective radiosensitization of p53 mutant pancreatic cancer cells by combined inhibition of Chk1 and PARP1," Cell Cycle (2011) 10(24):4321-4329.

Yang, X. et al., "JF-305, a pancreatic cancer cell line is highly sensitive to the PARP inhibitor olaparib," Oncology Lett. (2015) 9:757-761.

PHTHALAZINONE DERIVATIVES

CROSS-REFERENCE TO RELATED APPLICATIONS

This is a continuation of U.S. application Ser. No. 14/483,663 filed Sep. 11, 2014, which is a continuation of U.S. application Ser. No. 13/179,353 filed Jul. 8, 2011, now U.S. Pat. No. 8,912,187, which is a continuation of U.S. application Ser. No. 12/109,260 filed Apr. 24, 2008, now U.S. Pat. No. 7,981,889, which is a continuation of U.S. application Ser. No. 10/876,080 filed Jun. 24, 2004, now U.S. Pat. No. 7,449,464, which is a continuation-in-part of U.S. application Ser. No. 10/799,154 filed Mar. 12, 2004, now abandoned, which claims priority to U.S. Provisional Application Nos. 60/526,244 filed Dec. 1, 2003 and 60/454,995 filed Mar. 14, 2003, and further claims foreign priority to United Kingdom Patent Application No. 0305681.9 filed Mar. 12, 2003. U.S. application Ser. No. 10/876,080 also claims priority to U.S. Provisional Application No. 60/493,399 filed Aug. 6, 2003. All of the above are hereby incorporated by reference in their entireties.

The present invention relates to phthalazinone derivatives, and their use as pharmaceuticals. In particular, the present invention relates to the use of these compounds to inhibit the activity of the enzyme poly(ADP-ribose)polymerase, also known as poly(ADP-ribose)synthase and poly ADP-ribosyltransferase, and commonly referred to as PARP.

The mammalian enzyme PARP (a 113-kDa multidomain protein) has been implicated in the signalling of DNA damage through its ability to recognize and rapidly bind to DNA single or double strand breaks (D'Amours, et al., *Biochem. J.*, 342, 249-268 (1999)).

Several observations have led to the conclusion that PARP participates in a variety of DNA-related functions including gene amplification, cell division, differentiation, apoptosis, DNA base excision repair and also effects on telomere length and chromosome stability (d'Adda di Fagagna, et al., *Nature Gen.*, 23(1), 76-80 (1999)).

Studies on the mechanism by which PARP modulates DNA repair and other processes has identified its importance in the formation of poly(ADP-ribose) chains within the cellular nucleus (Althaus, F. R. and Richter, C., ADP-Ribosylation of Proteins: Enzymology and Biological Significance, Springer-Verlag, Berlin (1987)). The DNA-bound, activated PARP utilizes NAD to synthesize poly (ADP-ribose) on a variety of nuclear target proteins, including topoisomerase, histones and PARP itself (Rhun, et al., *Biochem. Biophys. Res. Commun.*, 245, 1-10 (1998))

Poly(ADP-ribosyl)ation has also been associated with malignant transformation. For example, PARP activity is higher in the isolated nuclei of SV40-transformed fibroblasts, while both leukemic cells and colon cancer cells show higher enzyme activity than the equivalent normal leukocytes and colon mucosa (Miwa, et al., *Arch. Biochem. Biophys.*, 181, 313-321 (1977); Burzio, et al., *Proc. Soc. Exp. Bioi. Med.*, 149, 933-938 (1975); and Hirai, et al., *Cancer Res.*, 43, 3441-3446 (1983)).

A number of low-molecular-weight inhibitors of PARP have been used to elucidate the functional role of poly(ADP-ribosyl)ation in DNA repair. In cells treated with alkylating agents, the inhibition of PARP leads to a marked increase in DNA-strand breakage and cell killing (Durkacz, et al., *Nature*, 283, 593-596 (1980); Berger, N. A., *Radiation Research*, 101, 4-14 (1985)).

Subsequently, such inhibitors have been shown to enhance the effects of radiation response by suppressing the repair of potentially lethal damage (Ben-Hur, et al., *British Journal of Cancer*, 49 (Suppl. VI), 34-42 (1984); Schlicker, et al., *Int. J. Radiat. Bioi.*, 75, 91-100 (1999)). PARP inhibitors have been reported to be effective in radio sensitising hypoxic tumour cells (U.S. Pat. No. 5,032,617; U.S. Pat. No. 5,215,738 and U.S. Pat. No. 5,041,653).

Furthermore, PARP knockout (PARP −/−) animals exhibit genomic instability in response to alkylating agents and γ-irradiation (Wang, et al., *Genes Dev.*, 9, 509-520 (1995); Menissier de Murcia, et al., *Proc. Natl. Acad. Sci. USA*, 94, 7303-7307 (1997)).

A role for PARP has also been demonstrated in certain vascular diseases, septic shock, ischaemic injury and neurotoxicity (Cantoni, et al., *Biochim. Biophys. Acta*, 1014, 1-7 (1989); Szabo, et al., *J. Chin. Invest.*, 100, 723-735 (1997)). Oxygen radical DNA damage that leads to strand breaks in DNA, which are subsequently recognised by PARP, is a major contributing factor to such disease states as shown by PARP inhibitor studies (Cosi, et al., *J. Neurosci. Res.*, 39, 38-46 (1994); Said, et al., *Proc. Natl. Acad. Sci. U.S.A.*, 93, 4688-4692 (1996)). More recently, PARP has been demonstrated to play a role in the pathogenesis of haemorrhagic shock (Liaudet, et al., *Proc. Natl. Acad. Sci. U.S.A.*, 97(3), 10203-10208 (2000)).

It has also been demonstrated that efficient retroviral infection of mammalian cells is blocked by the inhibition of PARP activity. Such inhibition of recombinant retroviral vector infections was shown to occur in various different cell types (Gaken, et al., *J. Virology*, 70(6), 3992-4000 (1996)). Inhibitors of PARP have thus been developed for the use in anti-viral therapies and in cancer treatment (WO 91/18591).

Moreover, PARP inhibition has been speculated to delay the onset of aging characteristics in human fibroblasts (Rattan and Clark, *Biochem. Biophys. Res. Comm.*, 201(2), 665-672 (1994)). This may be related to the role that PARP plays in controlling telomere function (d'Adda di Fagagna, et al., *Nature Gen.*, 23(1), 76-80 (1999)).

Some of the present inventors have previously described (WO 02/36576) a class of 1(2H)-phthalazinone compounds which act as PARP inhibitors. The compounds have the general formula:

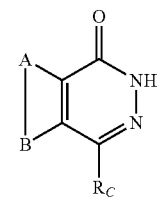

where A and B together represent an optionally substituted, fused aromatic ring and where $R_c$ is represented by -L-$R_L$. A large number of examples are of the formula:

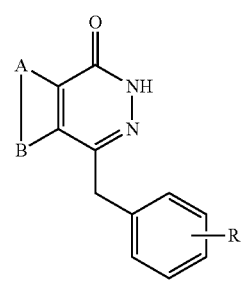

where R represent one or more optional substituents.

The present inventors have now discovered that compounds where R is of a certain nature exhibit surprising levels of inhibition of the activity of PARP, and/or of potentiation of tumour cells to radiotherapy and various chemotherapies.

Accordingly, the first aspect of the present invention provides a compound of the formula (I):

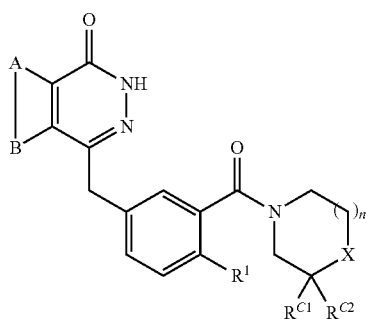

and isomers, salts, solvates, chemically protected forms, and prodrugs thereof
wherein:

A and B together represent an optionally substituted, fused aromatic ring;

X can be $NR^X$ or $CR^XR^Y$;

if $X=NR^X$ then n is 1 or 2 and if $X=CR^XR^Y$ then n is 1;

$R^X$ is selected from the group consisting of H, optionally substituted $C_{1-20}$ alkyl, $C_{5-20}$ aryl, $C_{3-20}$ heterocyclyl, amido, thioamido, ester, acyl, and sulfonyl groups;

$R^Y$ is selected from H, hydroxy, amino;

or $R^X$ and $R^Y$ may together form a spiro-$C_{3-7}$ cycloalkyl or heterocyclyl group;

$R^{C1}$ and $R^{C2}$ are independently selected from the group consisting of hydrogen and $C_{1-4}$ alkyl, or when X is $CR^XR^Y$, $R^{C1}$, $R^{C2}$, $R^X$ and $R^Y$, together with the carbon atoms to which they are attached, may form an optionally substituted fused aromatic ring; and $R^1$ is selected from H and halo.

Therefore, if X is $CR^XR^Y$, then n is 1 and the compound is of formula (Ia):

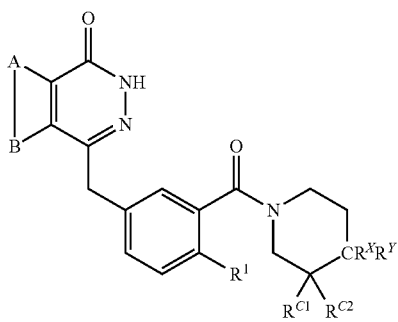

If X is $NR^X$, and n is 1, the compound is of formula (Ib):

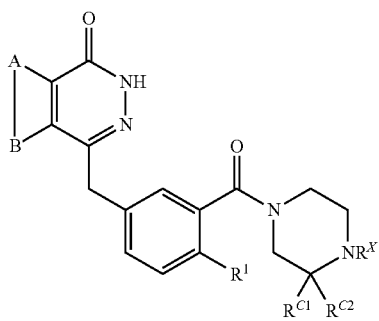

If X is $NR^X$, and n is 2, the compound is of formula (Ic):

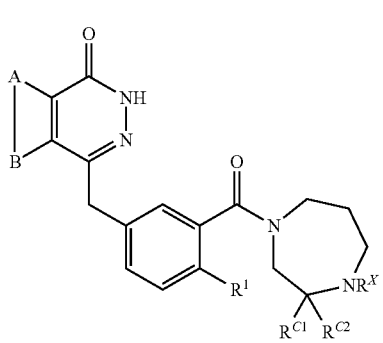

A second aspect of the present invention provides a pharmaceutical composition comprising a compound of the first aspect and a pharmaceutically acceptable carrier or diluent.

A third aspect of the present invention provides the use of a compound of the first aspect in a method of treatment of the human or animal body.

A fourth aspect of the present invention provides the use of a compound as defined in the first aspect of the invention in the preparation of a medicament for:
(a) inhibiting the activity of PARP (PARP-1 and/or PARP-2);
(b) the treatment of: vascular disease; septic shock; ischaemic injury, both cerebral and cardiovascular; reperfusion injury, both cerebral and cardiovascular; neurotoxicity, including acute and chronic treatments for stroke and Parkinsons disease; haemorraghic shock; inflammatory diseases, such as arthritis; multiple sclerosis; secondary effects of diabetes; as well as the acute treatment of cytoxicity following cardiovascular surgery or diseases ameliorated by the inhibition of the activity of PARP;
(c) use as an adjunct in cancer therapy or for potentiating tumour cells for treatment with ionizing radiation or chemotherapeutic agents.

In particular, compounds as defined in the first aspect of the invention can be used in anti-cancer combination therapies (or as adjuncts) along with alkylating agents, such as methyl methanesulfonate (MMS), temozolomide and dacarbazine (DTIC), also with topoisomerase-1 inhibitors like Irinotecan, Rubitecan, Exatecan, Lurtotecan, Gimetecan, Diflomotecan (homocamptothecins); as well as 7-substituted non-silatecans; the 7-silyl camptothecins, BNP 1350; and non-camptothecin topoisomerase-I inhibitors such as indolocarbazoles also dual topoisomerase-I and II inhibitors like the benzophenazines, XR 11576/MLN 576 and benzopyridoindoles. Such combinations could be given, for example, as intravenous preparations or by oral administration as dependent on the preferred method of administration for the particular agent.

Other further aspects of the invention provide for the treatment of disease ameliorated by the inhibition of PARP, comprising administering to a subject in need of treatment a therapeutically-effective amount of a compound as defined in the first aspect, preferably in the form of a pharmaceutical composition and the treatment of cancer, comprising administering to a subject in need of treatment a therapeutically-effective amount of a compound as defined in the first aspect in combination, preferably in the form of a pharmaceutical composition, simultaneously or sequentially with ionizing radiation or chemotherapeutic agents.

In further aspects of the present invention, the compounds may be used in the preparation of a medicament for the treatment of cancer which is deficient in Homologous Recombination (HR) dependent DNA double strand break (DSB) repair activity, or in the treatment of a patient with a cancer which is deficient in HR dependent DNA DSB repair activity, comprising administering to said patient a therapeutically-effective amount of the compound.

The HR dependent DNA DSB repair pathway repairs double-strand breaks (DSBs) in DNA via homologous mechanisms to reform a continuous DNA helix (K. K. Khanna and S. P. Jackson, Nat. Genet. 27(3): 247-254 (2001)). The components of the HR dependent DNA DSB repair pathway include, but are not limited to, ATM (NM_000051), RAD51 (NM_002875), RAD51L1 (NM_002877), RAD51C (NM_002876), RAD51L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS1 (NM_002485). Other proteins involved in the HR dependent DNA DSB repair pathway include regulatory factors such as EMSY (Hughes-Davies, et al., *Cell*, 115, pp 523-535). HR components are also described in Wood, et al., *Science*, 291, 1284-1289 (2001).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterised in the art (see for example, Wood, et al., *Science*, 291, 1284-1289 (2001)) and include the components listed above.

In some preferred embodiments, the cancer cells may have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (Hughes-Davies, et al., *Cell*, 115, 523-535).

BRCA1 and BRCA2 are known tumour suppressors whose wild-type alleles are frequently lost in tumours of heterozygous carriers (Jasin M., *Oncogene*, 21(58), 8981-93 (2002); Tutt, et al., *Trends Mol Med.*, 8(12), 571-6, (2002)). The association of BRCA1 and/or BRCA2 mutations with breast cancer is well-characterised in the art (Radice, P. J., *Exp Clin Cancer Res.*, 21(3 Supply, 9-12 (2002)). Amplification of the EMSY gene, which encodes a BRCA2 binding factor, is also known to be associated with breast and ovarian cancer.

Carriers of mutations in BRCA1 and/or BRCA2 are also at elevated risk of cancer of the ovary, prostate and pancreas.

In some preferred embodiments, the individual is heterozygous for one or more variations, such as mutations and polymorphisms, in BRCA1 and/or BRCA2 or a regulator thereof. The detection of variation in BRCA1 and BRCA2 is well-known in the art and is described, for example in EP 699 754, EP 705 903, Neuhausen, S. L. and Ostrander, E. A., *Genet. Test*, 1, 75-83 (1992); Chappnis, P. O. and Foulkes, W. D., *Cancer Treat Res*, 107, 29-59 (2002); Janatova M., et al., *Neoplasma*, 50(4), 246-50 (2003); Jancarkova, N., *Ceska Gynekol.*, 68(1), 11-6 (2003)). Determination of amplification of the BRCA2 binding factor EMSY is described in Hughes-Davies, et al., *Cell*, 115, 523-535).

Mutations and polymorphisms associated with cancer may be detected at the nucleic acid level by detecting the presence of a variant nucleic acid sequence or at the protein level by detecting the presence of a variant (i.e. a mutant or allelic variant) polypeptide.

DEFINITIONS

The term "aromatic ring" is used herein in the conventional sense to refer to a cyclic aromatic structure, that is, a cyclic structure having delocalised n-electron orbitals.

The aromatic ring fused to the main core, i.e. that formed by -A-B—, may bear further fused aromatic rings (resulting in, e.g. naphthyl or anthracenyl groups). The aromatic ring(s) may comprise solely carbon atoms, or may comprise carbon atoms and one or more heteroatoms, including but not limited to, nitrogen, oxygen, and sulfur atoms. The aromatic ring(s) preferably have five or six ring atoms.

The aromatic ring(s) may optionally be substituted. If a substituent itself comprises an aryl group, this aryl group is not considered to be a part of the aryl group to which it is attached. For example, the group biphenyl is considered herein to be a phenyl group (an aryl group comprising a single aromatic ring) substituted with a phenyl group. Similarly, the group benzylphenyl is considered to be a phenyl group (an aryl group comprising a single aromatic ring) substituted with a benzyl group.

In one group of preferred embodiments, the aromatic group comprises a single aromatic ring, which has five or six ring atoms, which ring atoms are selected from carbon, nitrogen, oxygen, and sulfur, and which ring is optionally substituted. Examples of these groups include, but are not limited to, benzene, pyrazine, pyrrole, thiazole, isoxazole, and oxazole. 2-Pyrone can also be considered to be an aromatic ring, but is less preferred.

If the aromatic ring has six atoms, then preferably at least four, or even five or all, of the ring atoms are carbon. The other ring atoms are selected from nitrogen, oxygen and sulphur, with nitrogen and oxygen being preferred. Suitable groups include a ring with: no hetero atoms (benzene); one nitrogen ring atom (pyridine); two nitrogen ring atoms (pyrazine, pyrimidine and pyridazine); one oxygen ring atom (pyrone); and one oxygen and one nitrogen ring atom (oxazine).

If the aromatic ring has five ring atoms, then preferably at least three of the ring atoms are carbon. The remaining ring atoms are selected from nitrogen, oxygen and sulphur. Suitable rings include a ring with: one nitrogen ring atom (pyrrole); two nitrogen ring atoms (imidazole, pyrazole); one oxygen ring atom (furan); one sulphur ring atom (thiophene); one nitrogen and one sulphur ring atom (isothiazole, thiazole); and one nitrogen and one oxygen ring atom (isoxazole or oxazole).

The aromatic ring may bear one or more substituent groups at any available ring position. These substituents are selected from halo, nitro, hydroxy, ether, thiol, thioether, amino, $C_{1-7}$ alkyl, $C_{3-20}$ heterocyclyl and $C_{5-20}$ aryl. The aromatic ring may also bear one or more substituent groups which together form a ring. In particular these may be of formula —$(CH_2)_m$— or —O—$(CH_2)_p$—O—, where m is 2, 3, 4 or 5 and p is 1, 2 or 3.

Alkyl: The term "alkyl" as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g. partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g. $C_{1-4}$, $C_{1-7}$, $C_{1-20}$, $C_{2-7}$, $C_{2-7}$, etc.) denote the number of carbon atoms, or range of number of carbon atoms. For example, the term "$C_{1-4}$ alkyl", as used herein, pertains to an alkyl group having from 1 to 4 carbon atoms. Examples of groups of alkyl groups include $C_{1-4}$ alkyl ("lower alkyl"), $C_{1-7}$ alkyl, and $C_{1-20}$ alkyl. Note that the first prefix may vary according to other limitations; for example, for unsaturated alkyl groups, the first prefix must be at least 2; for cyclic alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include, but are not limited to, iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl", as used herein, pertains to an alkyl group having one or more carbon-carbon double bonds. Examples of alkenyl groups include $C_{2-4}$ alkenyl, $C_{2-7}$ alkenyl, $C_{2-20}$ alkenyl.

Examples of (unsubstituted) unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

Alkynyl: The term "alkynyl", as used herein, pertains to an alkyl group having one or more carbon-carbon triple bonds. Examples of alkynyl groups include $C_{2-4}$ alkynyl, $C_{2-7}$ alkynyl, $C_{2-20}$ alkynyl.

Examples of (unsubstituted) unsaturated alkynyl groups include, but are not limited to, ethynyl (ethinyl, —CCH) and 2-propynyl (propargyl, —$CH_2$—CCH).

Cycloalkyl: The term "cycloalkyl", as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g. partially unsaturated, fully unsaturated), which moiety has from 3 to 20 carbon atoms (unless otherwise specified), including from 3 to 20 ring atoms. Thus, the term "cycloalkyl" includes the sub-classes cycloalkenyl and cycloalkynyl. Preferably, each ring has from 3 to 7 ring atoms. Examples of groups of cycloalkyl groups include $C_35_{20}$ cycloalkyl, $C_{3-15}$ cycloalkyl, $C_{3-10}$ cycloalkyl, $C_{3-7}$ cycloalkyl.

Examples of cycloalkyl groups include, but are not limited to, those derived from:
saturated monocyclic hydrocarbon compounds: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);
unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);
saturated polycyclic hydrocarbon compounds: thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);
unsaturated polycyclic hydrocarbon compounds: camphene ($C_{10}$), limonene ($C_{10}$), pinene ($C_{10}$);
polycyclic hydrocarbon compounds having an aromatic ring: indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Heterocyclyl: The term "heterocyclyl", as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms. Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of monocyclic heterocyclyl groups include, but are not limited to, those derived from:
$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$).

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Spiro-$C_{3-7}$ cycloalkyl or heterocyclyl: The term "spiro $C_{3-7}$ cycloalkyl or heterocyclyl" as used herein, refers to a $C_{3-7}$ cycloalkyl or $C_{3-7}$ heterocyclyl ring joined to another ring by a single atom common to both rings.

$C_{5-20}$ aryl: The term "$C_{5-20}$ aryl" as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups" in which case the group may conveniently be referred to as a "$C_{5-20}$ carboaryl" group.

Examples of $C_{6-20}$ aryl groups which do not have ring heteroatoms (i.e. $C_{6-20}$ carboaryl groups) include, but are not limited to, those derived from benzene (i.e. phenyl) ($C_6$), naphthalene ($C_{10}$), anthracene ($C_{14}$), phenanthrene ($C_{14}$), and pyrene ($C_{16}$).

Alternatively, the ring atoms may include one or more heteroatoms, including but not limited to oxygen, nitrogen, and sulfur, as in "heteroaryl groups". In this case, the group may conveniently be referred to as a "$C_{6-20}$ heteroaryl" group, wherein "$C_{6-20}$" denotes ring atoms, whether carbon atoms or heteroatoms. Preferably, each ring has from 5 to 7 ring atoms, of which from 0 to 4 are ring heteroatoms.

Examples of $C_{6-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, triazole, isothiazole, oxadiazole, tetrazole and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine) and triazine.

The heteroaryl group may be bonded via a carbon or hetero ring atom.

Examples of $C_{6-20}$ heteroaryl groups which comprise fused rings, include, but are not limited to, $C_9$ heteroaryl groups derived from benzofuran, isobenzofuran, benzothiophene, indole, isoindole; $C_{10}$ heteroaryl groups derived from quinoline, isoquinoline, benzodiazine, pyridopyridine; $C_{14}$ heteroaryl groups derived from acridine and xanthene.

The above alkyl, heterocyclyl, and aryl groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —$NO_2$.

Cyano (nitrile, carbonitrile): —CN.

Acyl (keto): —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)$CH_3$ (acetyl), —C(=O)$CH_2CH_3$ (propionyl), —C(=O)C($CH_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)O$CH_3$, —C(=O)O$CH_2CH_3$, —C(=O)OC($CH_3$)$_3$, and —C(=O)OPh.

Amido (carbamoyl, carbamyl, aminocarbonyl, carboxamide): —C(=O)$NR^1R^2$, wherein $R^1$ and $R^2$ are independently amino substituents, as defined for amino groups. Examples of amido groups include, but are not limited to, —C(=O)$NH_2$, —C(=O)NH$CH_3$, —C(=O)N($CH_3$)$_2$, —C(=O)NH$CH_2CH_3$, and —C(=O)N($CH_2CH_3$)$_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinylcarbonyl.

Amino: —$NR^1R^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, —$NH_2$, —NH$CH_3$, —NH(CH_3)$_2$, —N(CH_3)$_2$, —N($CH_2CH_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. In particular, the cyclic amino groups may be substituted on their ring by any of the substituents defined here, for example carboxy, carboxylate and amido.

Acylamido (acylamino): —$NR^1$C(=O)$R^2$, wherein $R^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and $R^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —NHC(=O)CH₃, —NHC(=O)CH₂CH₃, and —NHC(=O)Ph. R¹ and R² may together form a cyclic structure, as in, for example, succinimidyl, maleimidyl, and phthalimidyl:

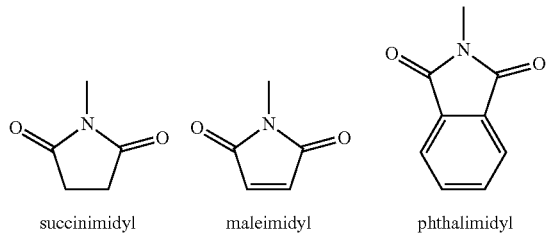

succinimidyl    maleimidyl    phthalimidyl

Ureido: —N(R¹)CONR²R³ wherein R² and R³ are independently amino substituents, as defined for amino groups, and R1 is a ureido substituent, for example, hydrogen, a $C_{1-7}$alkyl group, a $C_{3-20}$ heterocyclyl group, or a $C_{5-20}$aryl group, preferably hydrogen or a $C_{1-7}$alkyl group. Examples of ureido groups include, but are not limited to, —NHCONH₂, —NHCONHMe, —NHCONHEt, —NHCONMe₂, —NHCONEt₂, —NMeCONH₂, —NMeCONHMe, —NMeCONHEt, —NMeCONMe₂, —NMeCONEt₂ and —NHCONHPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH₃ (acetoxy), —OC(=O)CH₂CH₃, —OC(=O)C(CH₃)₃, —OC(=O)Ph, —OC(=O)C₆H₄F, and —OC(=O)CH₂Ph.

Thiol: —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH₃ and —SCH₂CH₃.

Sulfoxide (sulfinyl): —S(=O)R, wherein R is a sulfoxide substituent, for example, a $C_{1-7}$ alkyl group, a $C_{3-20}$ heterocyclyl group, or a $C_{5-20}$ aryl group, preferably a $C_{1-7}$ alkyl group. Examples of sulfoxide groups include, but are not limited to, —S(=O)CH₃ and —S(=O)CH₂CH₃.

Sulfonyl (sulfone): —S(=O)₂R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)₂CH₃ (methanesulfonyl, mesyl), —S(=O)₂CF₃, —S(=O)₂CH₂CH₃, and 4-methylphenylsulfonyl (tosyl).

Thioamido (thiocarbamyl): —C(=S)NR¹R², wherein R¹ and R² are independently amino substituents, as defined for amino groups. Examples of amido groups include, but are not limited to, —C(=S)NH₂, —C(=S)NHCH₃, —C(=S)N(CH₃)₂, and —C(=S)NHCH₂CH₃.

Sulfonamino: —NR¹S(=O)₂R, wherein R¹ is an amino substituent, as defined for amino groups, and R is a sulfonamino substituent, for example, a $C_{1-7}$alkyl group, a $C_{3-20}$ heterocyclyl group, or a $C_{5-20}$aryl group, preferably a $C_{1-7}$alkyl group. Examples of sulfonamino groups include, but are not limited to, —NHS(=O)₂CH₃, —NHS(=O)₂Ph and —N(CH₃)S(=O)₂C₆H₅.

As mentioned above, the groups that form the above listed substituent groups, e.g. $C_{1-7}$ alkyl, $C_{3-20}$ heterocyclyl and $C_{5-20}$ aryl, may themselves be substituted. Thus, the above definitions cover substituent groups which are substituted.

BRIEF DESCRIPTION OF FIGURES

FIG. 1A shows Brca1 wild type (11CO:■), heterozygous (Cre6:▲) and deficient (Cre10:●) embryonic fibroblastic stem (ES) cells under continuous exposure to compound 4. Error bars represent standard errors of the mean.

FIG. 1B shows Brca2 wild type (D3:■), heterozygous (Cre6:▲) and deficient (Cre24:●) ES cells under continuous exposure to compound 4. Error bars represent standard errors of the mean.

FURTHER PREFERENCES

Figure 1A:
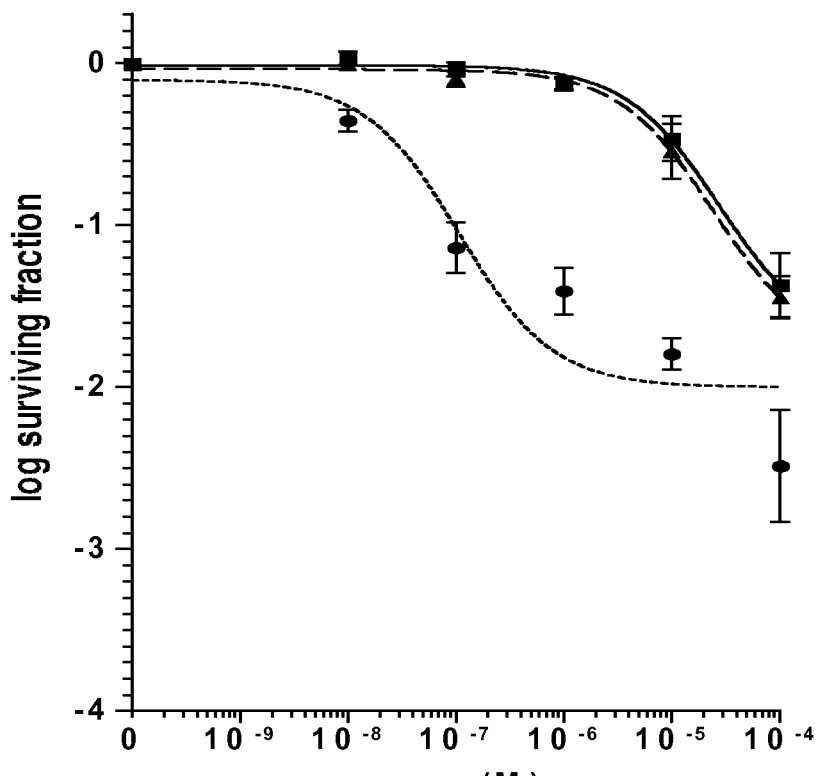
FIGS. 1A-B show clonogenic survival curves of cells proficient and deficient in Brca1 exposed to compound (4) of the present invention.

The following preferences can apply to each aspect of the present invention, where applicable.

In the present invention, the fused aromatic ring(s) represented by -A-B— preferably consist of solely carbon ring atoms, and thus may be benzene, naphthalene, and is more preferably benzene. As described above, these rings may be substituted, but in some embodiments are preferably unsubstituted.

If the fused aromatic ring represented by -A-B— bears a substituent group, it is preferably attached to the atom which itself is attached to the central ring meta- to the carbonyl group. Thus, if the fused aromatic ring is a benzene ring, the preferred place of substitution is shown in the formula below by *:

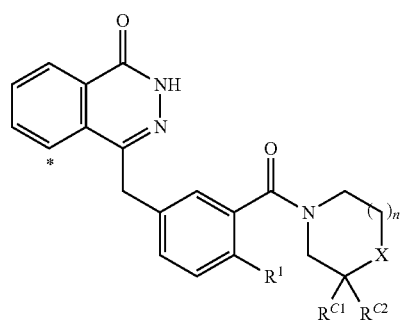

which is usually termed the 5-position of the phthalazinone moiety.

R¹ is preferably selected from H, Cl and F, and is more preferably F.

It is preferred that $R^{C1}$ and $R^{C2}$ are independently selected from hydrogen and $C_{1-4}$ alkyl, and more preferably H and methyl. It is more preferred that at least one of $R^{C1}$ and $R^{C2}$ are hydrogen, with the most preferred option being that both are hydrogen.

When n is 2, X is $NR^X$. In these embodiments, $R^X$ is preferably selected from the group consisting of: H; optionally substituted $C_{1-20}$ alkyl (for example, optionally substituted $C_{5-20}$ arylmethyl); optionally substituted $C_{5-20}$ aryl;

optionally substituted ester groups, wherein the ester substituent is preferably $C_{1-20}$ alkyl; optionally substituted acyl groups; optionally substituted amido groups; optionally substituted thioamido groups; and optionally substituted sulfonyl groups. $R^X$ is more preferably selected from the group consisting of: H; optionally substituted $C_{1-20}$ alkyl; optionally substituted $C_{5-20}$ aryl; and optionally substituted ester groups, wherein the ester substituent is preferably $C_{1-20}$ alkyl.

When n is 1, X may be $NR^X$ or $CR^X CR^Y$.

In embodiments where X is $NR^X$, $R^X$ is preferably selected from the group consisting of: H; optionally substituted $C_{1-20}$ alkyl (for example, optionally substituted $C_{5-20}$ arylmethyl); optionally substituted $C_{5-20}$ aryl; optionally substituted acyl; optionally substituted sulfonyl; optionally substituted amido; and optionally substituted thioamido groups.

In embodiments where X is $CR^X R^Y$, $R^Y$ is preferably H. $R^X$ is preferably selected from the group consisting of: H; optionally substituted $C_{1-20}$ alkyl (for example, optionally substituted $C_{5-20}$ arylmethyl); optionally substituted $C_{5-20}$ aryl; optionally substituted $C_{3-20}$ heterocyclyl; optionally substituted acyl, wherein the acyl substituent is preferably selected from $C_{5-20}$ aryl and $C_{3-20}$ heterocylyl (e.g. piperazinyl); optionally substituted amido, wherein the amino groups are preferably selected from H and $C_{1-20}$ alkyl or together with the nitrogen atom, form a $C_{5-20}$ heterocyclic group; and optionally substituted ester groups, wherein the ester substituent is preferably selected from $C_{1-20}$ alkyl groups.

Particularly preferred compounds include: 1, 2, 3, 4, 10, 20, 59, 80, 135, 146, 192, 194, 195, 211 and 212.

Where appropriate, the above preferences may be taken in combination with each other.

forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

If the compound is in crystalline form, it may exist in a number of different polymorphic forms.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Particularly relevant to the present invention is the tautomeric pair illustrated below:

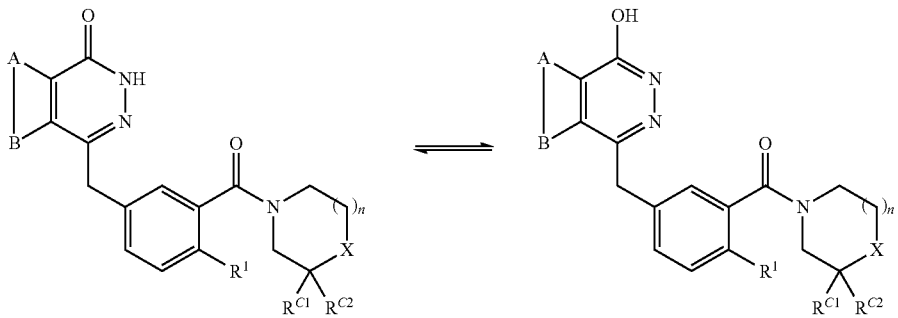

Includes Other Forms Included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (—$N^+HR^1R^2$), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasterioisomeric, epimeric, stereoisomeric, tautomeric, conformational, or anomeric forms, including but not limited to, cis- and trans- Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below, as well as its different polymorphic forms.

It may be convenient or desirable to prepare, purify, and/or handle a corresponding salt of the active compound, for example, a pharmaceutically-acceptable salt. Examples of pharmaceutically acceptable salts are discussed in Berge, et al., "Pharmaceutically Acceptable Salts", *J. Pharm. Sci.*, 66, 1-19 (1977).

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, "Protective Groups in Organic Synthesis" (T. Green and P. Wuts; 3rd Edition; John Wiley and Sons, 1999).

For example, a hydroxy group may be protected as an ether (—OR) or an ester (—CO(═O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(═O)CH₃, —OAc).

For example, an aldehyde or ketone group may be protected as an acetal or ketal, respectively, in which the carbonyl group (>C═O) is converted to a diether (>C(OR)₂), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH₃); a benzyloxy amide (—NHCO—OCH₂C₆H₅, —NH—Cbz); as a t-butoxy amide (—NHCO—OC(CH₃)₃, —NH-Boc); a 2-biphenyl-2-propoxy amide (—NHCO—OC (CH₃)₂C₆H₄C₆H₅, —NH-Bpoc), as a 9-fluorenylmethoxy amide (—NH—Fmoc), as a 6-nitroveratryloxy amide (—NH—Nvoc), as a 2-trimethylsilylethyloxy amide (—NH—Teoc), as a 2,2,2-trichloroethyloxy amide (—NH-Troc), as an allyloxy amide (—NH—Alloc), as a 2(-phenylsulphonyl)ethyloxy amide (—NH—Psec); or, in suitable cases, as an N-oxide (>NO.).

For example, a carboxylic acid group may be protected as an ester for example, as: a $C_{1-7}$ alkyl ester (e.g. a methyl ester; a t-butyl ester); a $C_{1-7}$ haloalkyl ester (e.g. a $C_{1-7}$ trihaloalkyl ester); a tri$C_{1-7}$ alkylsilyl-$C_{1-7}$ alkyl ester; or a $C_{5-20}$ aryl-$C_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH₂NHC(═O)CH₃).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required. Examples of such metabolically labile esters include, but are not limited to, those wherein R is $C_{1-20}$ alkyl (e.g. -Me, -Et); $C_{1-7}$ aminoalkyl (e.g. aminoethyl; 2-(N,N-diethylamino)ethyl; 2-(4-morpholino)ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxyl)carbonyloxyethyl; (4-tetrahydropyranyl) carbonyloxymethyl; and 1-(4-tetrahydropyranyl) carbonyloxyethyl).

Further suitable prodrug forms include phosphonate and glycolate salts. In particular, hydroxy groups (—OH), can be made into phosphonate prodrugs by reaction with chlorodibenzylphosphite, followed by hydrogenation, to form a phosphonate group —O—P(═O) (OH)₂. Such a group can be cleaved by phosphatase enzymes during metabolism to yield the active drug with the hydroxy group.

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane(methylene chloride, DCM), trifluoroacetic acid (TFA), dimethylformamide (DMF), tetrahydrofuran (THF), and dimethylsulfoxide (DMSO).

Synthesis

In the synthesis routes given below, the A-B fused ring is shown as a fused benzene ring for convenience. Compounds in which the A-B ring is other than benzene may be synthesised using methodologies analogous to those described below by the use of appropriate alternative starting materials.

Compounds of the present invention may be synthesised by reaction of a compound of Formula 1:

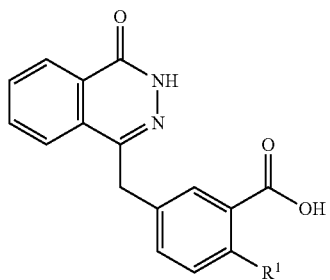

Formula 1 in which R$^1$ is as previously defined, with a compound of Formula 2:

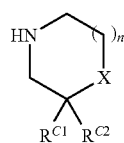

Formula 2 in which n, R$^{C1}$, R$^{C2}$ and X are as previously defined, in the presence of a coupling reagent system, for example 2-(1H-benzotriazol-1-yl)-1,1,3,3-tetramethyluronium tetrafluoroborate, 2-(1H-benzotriazol-1-yl)-1,1,3,3-tetramethyluronium hexafluorophosphate or (dimethylaminopropyl) ethylcarbodiimide hydrochloride/hydroxybenzotriazole, in the presence of a base, for example diisopropylethylamine, in a solvent, for example dimethylacetamide or dichloromethane, at a temperature in the range of 0° C. to the boiling point of the solvent used.

Alternatively, compounds of the present invention may be synthesised by conversion of a compound of Formula 1 into an activated species, for example an acid chloride or an activated ester such as an N-hydroxysuccinimide ester, using well-known methodologies, and reaction of the activated species with a compound of Formula 2.

Compounds of Formula 1 may be synthesised by reaction of a compound of Formula 3:

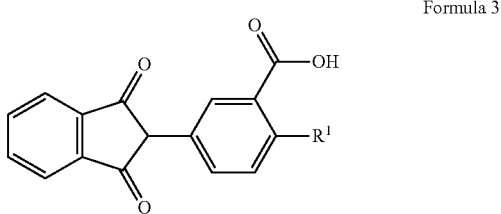

Formula 3 in which R$^1$ is as previously defined, or a compound of Formula 4:

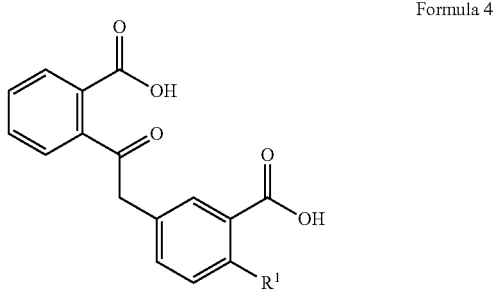

Formula 4 in which R$^1$ is as previously defined, or a mixture of a compound of Formula 3 and a compound of Formula 4, with a source of hydrazine, for example hydrazine hydrate, optionally in the presence of a base, for example triethylamine, optionally in the presence of a solvent, for example industrial methylated spirit, at a temperature in the range of 0° C. to the boiling point of the solvent used.

Compounds of Formula 3 or Formula 4, or mixtures thereof, may be synthesised by reaction of a compound of Formula 5:

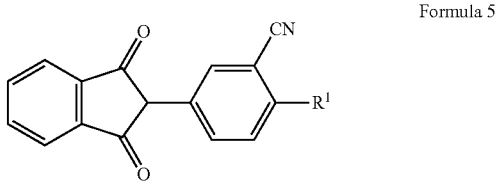

Formula 5 in which R$^1$ is as previously defined, with a reagent capable of hydrolysing a nitrile moiety, for example sodium hydroxide, in the presence of a solvent, for example water, at a temperature in the range of 0° C. to the boiling point of the solvent used.

Compounds of Formula 5 may be synthesised by reaction of a compound of Formula 6:

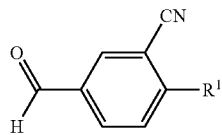

Formula 6 in which R¹ is as previously defined, with a compound of Formula 7:

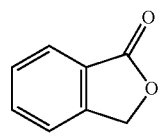

Formula 7 in the presence of a base, for example sodium methoxide, in a solvent, for example methanol, optionally in the presence of a water scavenger, for example ethyl propionate, at a temperature in the range of 0° C. to the boiling point of the solvent used.

Compounds of Formula 1 may also be synthesised by reaction of a compound of Formula 8:

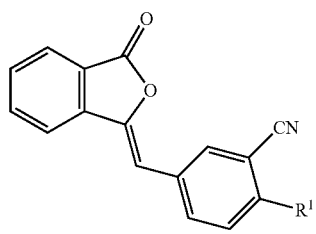

Formula 8 in which R¹ is as previously defined, with a reagent capable of hydrolysing a nitrile moiety, for example sodium hydroxide, in the presence of a solvent, for example water, at a temperature in the range of 0° C. to the boiling point of the solvent used, followed by reaction of the resulting intermediate with a source of hydrazine, for example hydrazine hydrate, at a temperature in the range of 0° C. to the boiling point of the solvent used.

Compounds of Formula 8 may be synthesised by reaction of a compound of Formula 9:

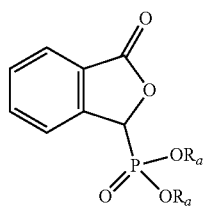

Formula 9 in which $R_a$ is a $C_{1-4}$ alkyl group, with a compound of Formula 6, in the presence of a base, for example triethylamine or lithium hexamethyldisilazide, in the presence of a solvent, for example tetrahydrofuran, at a temperature in the range of −80° C. to the boiling point of the solvent used.

Compounds of Formula 9 may be synthesised by methods analogous to those described in WO 02/26576.

Compounds of Formula 1 may also be synthesised by methods analogous to those described above in which the nitrile moiety in all Formulae is replaced by other moieties capable of generating a carboxylic acid, for example ester or carboxamide moieties.

Compounds of Formula 2 are commercially available or may be synthesised by methods reported in the chemical literature.

Compounds of the present invention in which X is $CR^XR^Y$, in which one of $R^X$ or $R^Y$ is an amido moiety, and which may therefore be represented by Formula 10:

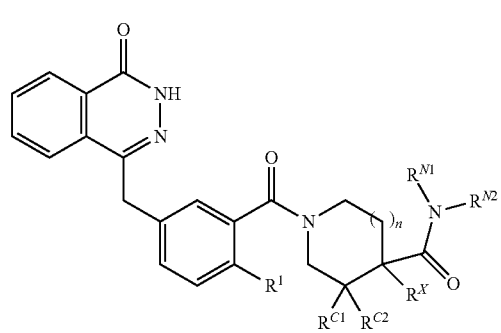

Formula 10 in which n, $R^{C1}$, $R^{C2}$, $R^1$ and $R^X$ are as previously defined and $R^{N1}$ and $R^{N2}$ are each individually selected from the group consisting of H, optionally substituted $C_{1-20}$ alkyl, $C_{5-20}$ aryl, $C_{3-20}$ heterocyclyl, or may together form an optionally substituted $C_{3-7}$ cycloalkyl or heterocyclyl group, may be synthesised by reaction of a compound of Formula 11:

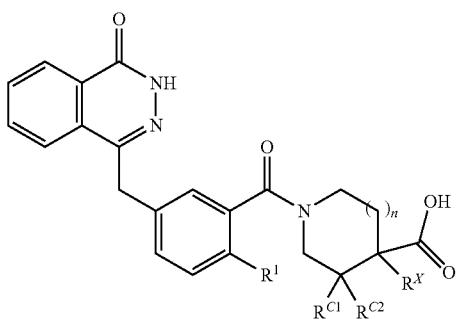

Formula 11 in which n, $R^{C1}$, $R^{C2}$, $R^1$ and $R^X$ are as previously defined, with a compound of Formula $HNR^{N1}R^{N2}$, in which $R^{N1}$ and $R^{N2}$ are as previously defined, in the presence of a coupling reagent system, for example 2-(1H-benzotriazol-1-yl)-1,1,3,3-tetramethyluronium tetrafluoroborate, 2-(1H-benzotriazol-1-yl)-1,1,3,3-tetramethyluronium hexafluorophosphate or (dimethylaminopropyl)ethylcarbodiimide hydrochloride/hydroxybenzotriazole, in the presence of a base, for example diisopropylethylamine, in a solvent, for example dimethylacetamide or dichloromethane, at a temperature in the range of 0° C. to the boiling point of the solvent used.

Alternatively, compounds of Formula 10 may be synthesised by conversion of a compound of Formula 11 into an activated species, for example an acid chloride or an activated ester such as an N-hydroxysuccinimide ester, using well-known methodologies, and reaction of the activated species with a compound of Formula $HNR^{N1}R^{N2}$.

Compounds of Formula 11 may be synthesised by deprotection of a protected form of a compound of Formula 11, for example a compound of Formula 12:

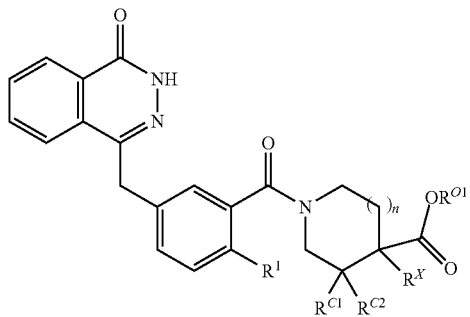

Formula 12 in which n, $R^{C1}$, $R^{C2}$, $R^1$ and $R^X$ are as previously defined and $R^{O1}$ is a $C_{1-4}$ alkyl group, using well known methodologies, for example base-catalysed hydrolysis in the presence of a source of hydroxide, for example sodium or lithium hydroxide, in the presence of a solvent, for example water and/or tetrahydrofuran, at a temperature in the range of 0° C. to the boiling point of the solvent used.

Compounds of Formula 12 may be synthesised from compounds of Formula 1 by the previously described methods.

Compounds of Formula $HNR^{N1}R^{N2}$ are commercially available or may be synthesised by methods reported in the chemical literature.

Compounds of the present invention in which X is NH and which may therefore be represented by Formula 13:

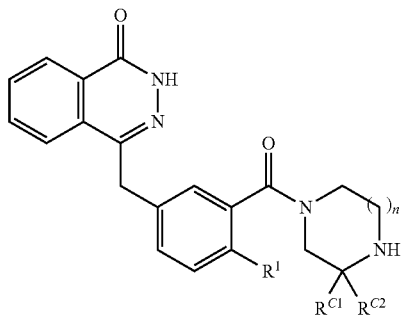

Formula 13 in which n, $R^{C1}$, $R^{C2}$ and $R^1$ are as previously defined, may be synthesised by deprotection of a protected form of a compound of Formula 13, for example a compound of Formula 14:

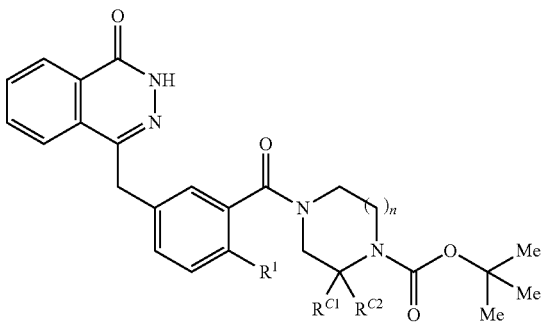

Formula 14 in which n, $R^{C1}$, $R^{C2}$ and $R^1$ are as previously defined, using well known methodologies, for example acid-catalysed cleavage, in the presence of an acid, for example trifluoroacetic acid or hydrochloric acid, in the presence of a solvent, for example dichloromethane or ethanol and/or water, at a temperature in the range of 0° C. to the boiling point of the solvent used.

Compounds of Formula 14 may be synthesised from compounds of Formula 1 by the previously described methods.

Compounds of the present invention in which X is $NR^X$, in which $R^X$ is an acyl moiety, and which may therefore be represented by Formula 15:

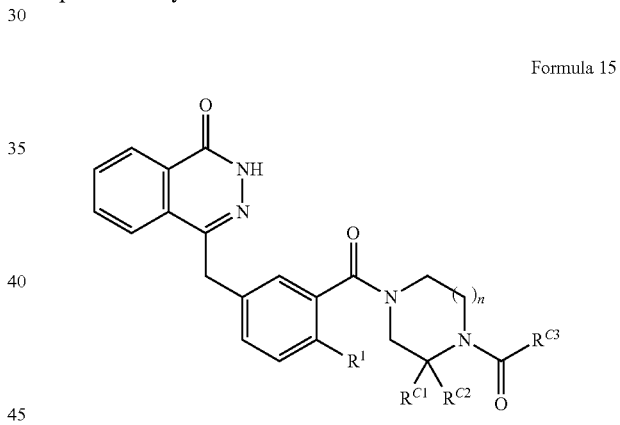

Formula 15 in which n, $R^{C1}$, $R^{C2}$ and $R^1$ are as previously defined and $R^{C3}$ is selected from the group consisting of optionally substituted $C_{1-20}$ alkyl, $C_{5-20}$ aryl and $C_{3-20}$ heterocyclyl, may be synthesised by reaction of a compound of Formula 13 with a compound of Formula $R^{C3}COX$, in which $R^{C3}$ is as previously defined and X is a suitable leaving group, for example a halogen such as chloro, optionally in the presence of a base, for example pyridine, triethylamine or diisopropylethylamine, optionally in the presence of a solvent, for example dichloromethane, at a temperature in the range of 0° C. to the boiling point of the solvent used.

Compounds of Formula $R^{C3}COX$ are commercially available or may be synthesised by methods reported in the chemical literature.

Compounds of Formula 15 may also be synthesised by reaction of a compound of Formula 13 with a compound of Formula $R^{C3}CO_2H$, in which $R^{C3}$ is as previously defined, in the presence of a coupling reagent system, for example 2-(1H-benzotriazol-1-yl)-1,1,3,3-tetramethyluronium tetrafluoroborate, 2-(1H-benzotriazol-1-yl)-1,1,3,3-tetramethyluronium hexafluorophosphate or (dimethylaminopropyl)

ethylcarbodiimide hydrochloride/hydroxybenzotriazole, in the presence of a base, for example diisopropylethylamine, in a solvent, for example dimethylacetamide or dichloromethane, at a temperature in the range of 0° C. to the boiling point of the solvent used.

Compounds of Formula $R^{C3}CO_2H$ are commercially available or may be synthesised by methods reported in the chemical literature.

Compounds of the present invention in which X is $NR^X$, in which $R^X$ is an amido or thioamido moiety, and which may therefore be represented by Formula 16:

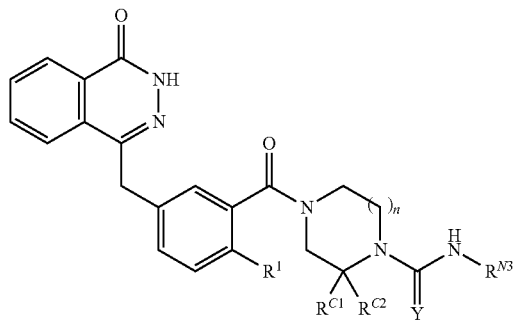

Formula 16 in which n, $R^{C1}$, $R^{C2}$ and $R^1$ are as previously defined, Y is O or S and $R^{N3}$ is selected from the group consisting of optionally substituted $C_{1-20}$ alkyl, $C_{5-20}$ aryl and $C_{2-20}$ heterocyclyl, may be synthesised by reaction of a compound of Formula 13 with a compound of Formula $R^{N3}NCY$, in which Y and $R^{N3}$ are as previously defined, in the presence of a solvent, for example dichloromethane, at a temperature in the range of 0° C. to the boiling point of the solvent used.

Compounds of Formula $R^{N3}NCY$ are commercially available or may be synthesised by methods reported in the chemical literature.

Compounds of the present invention in which X is $NR^X$, in which $R^X$ is a sulfonyl moiety, and which may therefore be represented by Formula 17:

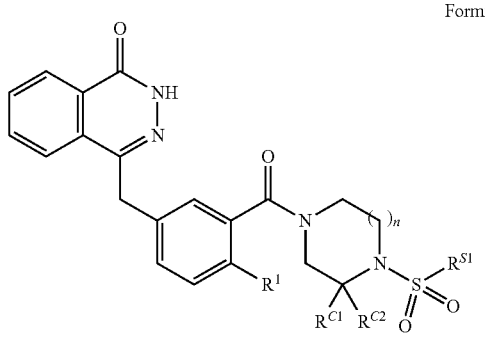

Formula 17 in which n, $R^{C1}$, $R^{C2}$ and $R^1$ are as previously defined and $R^{S1}$ is selected from the group consisting of optionally substituted $C_{1-20}$ alkyl, $C_{5-20}$ aryl and $C_{3-20}$ heterocyclyl, may be synthesised by reaction of a compound of Formula 13 with a compound of Formula $R^{S1}SO_2Cl$, in which $R^{S1}$ is as previously defined, optionally in the presence of a base, for example pyridine, triethylamine or diisopropylethylamine, in the presence of a solvent, for example dichloromethane, at a temperature in the range of 0° C. to the boiling point of the solvent used.

Compounds of Formula $R^{S1}SO_2Cl$ are commercially available or may be synthesised by methods reported in the chemical literature.

Compounds of the present invention in which X is $NR^X$, in which $R^X$ is selected from the group consisting of optionally substituted $C_{1-20}$ alkyl or $C_{3-20}$ heterocyclyl, and which may therefore be represented by Formula 18:

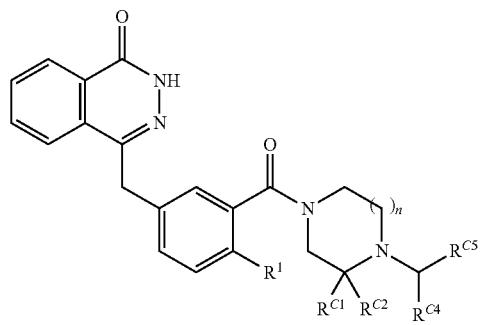

Formula 18 in which n, $R^{C1}$, $R^{C2}$ and $R^1$ are as previously defined and $R^{C4}$ and $R^{C5}$ are each individually selected from the group consisting of H, optionally substituted $C_{1-20}$ alkyl, $C_{5-20}$ aryl, $C_{3-20}$ heterocyclyl, or may together form an optionally substituted $C_{3-7}$ cycloalkyl or heterocyclyl group, may be synthesised by reaction of a compound of Formula 13 with a compound of Formula $R^{C4}COR^{C5}$, in which $R^{C4}$ and $R^{C5}$ are as previously defined, in the presence of a reducing agent, for example sodium cyanoborohydride or sodium triacetoxyborohydride, in the presence of a solvent, for example methanol, optionally in the presence of an acid catalyst, for example acetic acid, at a temperature in the range of 0° C. to the boiling point of the solvent used.

Compounds of Formula $R^{C4}COR^{C5}$ are commercially available or may be synthesised by methods reported in the chemical literature.

Use

The present invention provides active compounds, specifically, active in inhibiting the activity of PARP.

The term "active" as used herein, pertains to compounds which are capable of inhibiting PARP activity, and specifically includes both compounds with intrinsic activity (drugs) as well as prodrugs of such compounds, which prodrugs may themselves exhibit little or no intrinsic activity.

One assay which may conveniently be used in order to assess the PARP inhibition offered by a particular compound is described in the examples below.

The present invention further provides a method of inhibiting the activity of PARP in a cell, comprising contacting said cell with an effective amount of an active compound, preferably in the form of a pharmaceutically acceptable composition. Such a method may be practised in vitro or in vivo.

For example, a sample of cells may be grown in vitro and an active compound brought into contact with said cells, and the effect of the compound on those cells observed. As examples of "effect", the amount of DNA repair effected in a certain time may be determined. Where the active compound is found to exert an influence on the cells, this may be used as a prognostic or diagnostic marker of the efficacy of the compound in methods of treating a patient carrying cells of the same cellular type.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "adjunct" as used herein relates to the use of active compounds in conjunction with known therapeutic means. Such means include cytotoxic regimens of drugs and/or ionising radiation as used in the treatment of different cancer types. In particular, the active compounds are known to potentiate the actions of a number of cancer chemotherapy treatments, which include the topoisomerase class of poisons and most of the known alkylating agents used in treating cancer.

Active compounds may also be used as cell culture additives to inhibit PARP, for example, in order to sensitize cells to known chemotherapeutic agents or ionising radiation treatments in vitro.

Active compounds may also be used as part of an in vitro assay, for example, in order to determine whether a candidate host is likely to benefit from treatment with the compound in question.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

Formulations

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, diluents, excipients, etc. can be found in standard pharmaceutical texts. See, for example, "Handbook of Pharmaceutical Additives", 2nd Edition (eds. M. Ash and I. Ash), 2001 (Synapse Information Resources, Inc., Endicott, N.Y., USA), "Remington's Pharmaceutical Sciences", 20th edition, pub. Lippincott, Williams & Wilkins, 2000; and "Handbook of Pharmaceutical Excipients", 2nd edition, 1994.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g. compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, *acacia*, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavored basis, usually sucrose and *acacia* or tragacanth; pastilles comprising the active compound in an inert basis such as gelatin and glycerin, or sucrose and *acacia*; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 μg to about 250 mg per kilogram body weight of the subject per day. Where the active compound is a salt, an ester, prodrug, or the like, the amount administered is calculated on the basis of the parent compound and so the actual weight to be used is increased proportionately.

SYNTHESIS DATA

General Experimental Methods
Preparative HPLC

Samples were purified with a Waters mass-directed purification system utilising a Waters 600 LC pump, Waters Xterra C18 column (5 μm 19 mm×50 mm) and Micromass ZQ mass spectrometer, operating in positive ion electrospray ionisation mode. Mobile phases A (0.1% formic acid in water) and B (0.1% formic acid in acetonitrile) were used in a gradient; 5% B to 100% over 7 min, held for 3 min, at a flow rate of 20 ml/min.
Analytical HPLC-MS Analytical HPLC was typically carried out with a Spectra System P4000 pump and Jones Genesis C18 column (4 μm, 50 mm×4.6 mm). Mobile phases A (0.1% formic acid in water) and B (acetonitrile) were used in a gradient of 5% B for 1 min rising to 98% B after 5 min, held for 3 min at a flow rate of 2 ml/min. Detection was by a TSP UV 6000LP detector at 254 nm UV and range 210-600 nm PDA. The Mass spectrometer was a Finnigan LCQ operating in positive ion electrospray mode.
NMR $^1$H NMR and $^{13}$C NMR were typically recorded using Bruker DPX 300 spectrometer at 300 MHz and 75 MHz respectively. Chemical shifts were reported in parts per million (ppm) on the δ scale relative to tetramethylsilane internal standard. Unless stated otherwise all samples were dissolved in DMSO-$d_6$.
Synthesis of Key Intermediates a.
3-(4-Oxo-3,4-dihydrophthalazin-1-ylmethyl)benzoic acid (A)

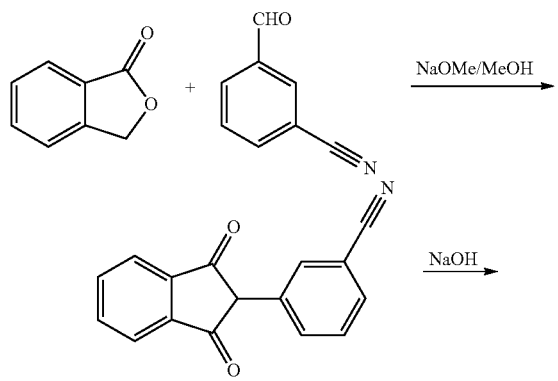

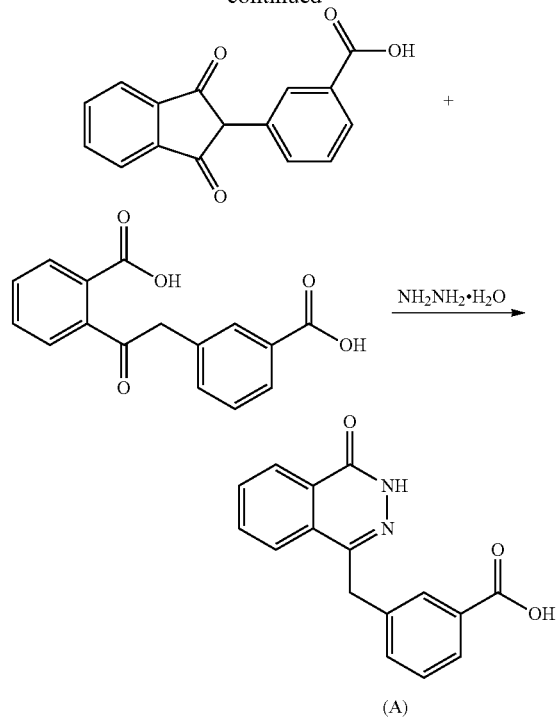

A mixture of 27% sodium methoxide solution in methanol (400 g, 2 mol) and methanol (150 ml) was added dropwise between ambient temperature and 30° C. over 15 minutes to a stirred mixture of phthalide (67 g, 0.5 mol), 3-formylbenzonitrile (65.5 g, 0.5 mol) and ethyl propionate (250 ml), the mixture was stirred at ambient temperature for 40 minutes and at reflux temperature for 1 hour, then it was allowed to cool to ambient temperature. The resulting red solid was collected by filtration, washed with ethyl acetate (2×50 ml) and dissolved in water (1800 ml). The solution was acidified by the addition of acetic acid (60 ml) and the resulting red solid was collected by filtration, washed with water (2×200 ml) and dried in vacuo to give 3-(1,3-dioxoindan-2-yl) benzonitrile (83.2 g) as a dark red solid, m.pt. 179-182° C., m/z (M+H)$^{+\cdot}$ 248, which was used without further purification.

3-(1,3-Dioxoindan-2-yl)benzonitrile (74.18 g, 0.3 mol) was added in portions to a solution of sodium hydroxide (36 g, 0.9 mol) in water (580 ml), the resulting dark red suspension was stirred at reflux temperature for 5 hours, then it was cooled to ambient temperature and washed with ethyl acetate (3×300 ml). The aqueous solution was acidified by the dropwise addition of concentrated hydrochloric acid (110 ml), the mixture was stirred at ambient temperature for 1 hour, then the resulting solid was collected by filtration, washed with water (2×200 ml) and dried in vacuo to give a 1:1 mixture of 3-(1,3-dioxoindan-2-yl)benzoic acid, (M+H)$^{+\cdot}$ 267, and 2-[2-(3-carboxyphenyl)acetyl]benzoic acid, (M+H)$^{+\cdot}$ 285, (69.32 g), which was used without further purification.

The mixture obtained in the previous step (52.8 g) was added to a solution of triethylamine (37.55 g, 0.372 mol) in industrial methylated spirit (500 ml) and the resulting cloudy solution was filtered through a pad of filter-aid to give a clear solution. Hydrazine monohydrate (9.3 g, 0.186 mol) was added in one portion at ambient temperature, the stirred mixture was heated under reflux for 1 hour, then it was concentrated in vacuo to approximately 250 ml and added to a solution of sodium acetate (41 g, 0.5 mol) in water (500 ml). The mixture was brought to pH 7 by the dropwise addition of concentrated hydrochloric acid, then it was stirred at ambient temperature for 3 hours. The resulting solid was collected by filtration, washed with water (50 ml) and dried in vacuo to give a white solid (15.62 g). The combined filtrate and washings were acidified to pH 6 by the addition of hydrochloric acid, then the mixture was stirred at ambient temperature for 3 hours. The resulting solid was collected by filtration, washed with water (50 ml) and dried in vacuo to give a second crop of off-white solid (17.57 g). The combined filtrate and washings from the second crop were readjusted to pH 6 and treated as before to give a third crop of pale orange solid (6.66 g). The three crops were combined to give essentially pure 3-(4-oxo-3,4-dihydrophthalazin-1-ylmethyl)benzoic acid (A), (M+H)$^{+}$ 281, $\delta_H$ 4.4 (2H, s), 7.2-7.4 (1H, m), 7.5-7.6 (1H, m), 7.7-8.0 (5H, m), 8.1-8.2 (1H, m), 12.6 (1H, s)

b. 2-Fluoro-5-(4-oxo-3,4-dihydro-phthalazin-1-ylmethyl)benzoic acid (B)

Dimethyl phosphite (22.0 g, 0.2 mol) was added drop-wise to a solution of sodium methoxide (43.0 g) in methanol (100 ml) at 0° C. 2-Carboxybenzaldehyde (21.0 g, 0.1 mol) was then added portion-wise to the reaction mixture as a slurry in methanol (40 ml), with the temperature kept below 5° C. The resulting pale yellow solution was warmed to 20° C. over 1 hour. Methanesulphonic acid (21.2 g, 0.22 mol) was added to the reaction drop-wise and the resulting white suspension was evaporated in vacuo. The white residue was quenched with water and extracted into chloroform (3×100 ml). The combined organic extracts were washed with water (2×100 ml), dried over MgSO$_4$, and evaporated in vacuo to yield (3-oxo-1,3-dihydro-isobenzofuran-1-yl)phosphonic acid dimethyl ester as a white solid (32.0 g, 95%, 95% purity). This was then used without further purification in the next stage.

To a mixture of (3-oxo-1,3-dihydro-isobenzofuran-1-yl) phosphonic acid dimethyl ester (35.0 g, 0.14 mol) in tetrahydrofuran (200 ml) and 2-fluoro-5-formylbenzonitrile (20.9 g, 0.14 mol) in tetrahydrofuran (130 ml) was added triethylamine (14 ml, 0.14 mol) drop-wise over 25 min, with the temperature kept below 15° C. The reaction mixture was warmed slowly to 20° C. over 1 hour and concentrated in vacuo. The white residue was slurried in water (250 ml) for 30 minutes, filtered, washed with water, hexane and ether, and dried to yield 2-fluoro-5-(3-oxo-3H-isobenzofuran-1-ylidenemethyl)benzonitrile as a 50:50 mixture of E and Z isomers (37.2 g, 96%);

m/z [M+1]$^+$ 266 (98% purity)

To a suspension of 2-fluoro-5-(3-oxo-3H-isobenzofuran-1-ylidenemethyl)benzonitrile in water (200 ml) was added aqueous sodium hydroxide (26.1 g in 50 ml water) solution and the reaction mixture was heated under nitrogen to 90° C. for 30 minutes. The reaction mixture was partially cooled to 70° C., and hydrazine hydrate (100 ml) was added and stirred for 18 hours at 70° C. The reaction was cooled to room temperature and acidified with 2M HCl to pH 4. The mixture was stirred for 10 min and filtered. The resulting solid was washed with water, hexane, ether, ethyl acetate and dried to yield 2-fluoro-5-(4-oxo-3,4-dihydrophthalazin-1-ylmethyl)benzoic acid as a pale pink powder (30.0 g, 77%). m/z [M+1]$^+$ 299 (96% purity), $\delta_H$ 4.4 (2H, s), 7.2-7.3 (1H, m), 7.5-7.6 (1H, m), 7.8-8.0 (4H, m), 8.2-8.3 (1H, m), 12.6 (1H, s).

c. 1-[3-(4-Oxo-3,4-dihydrophthalazin-1-ylmethyl)benzoyl]piperidine-4-carboxylic acid (C)

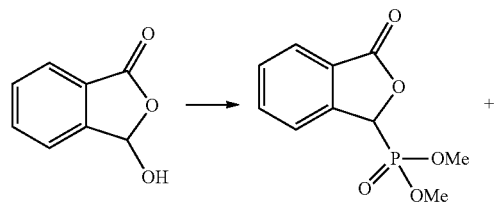

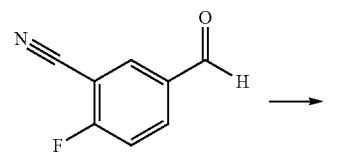

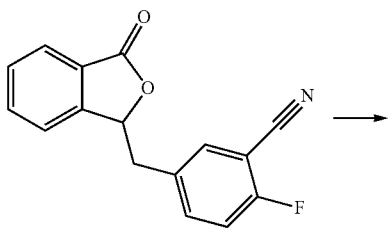

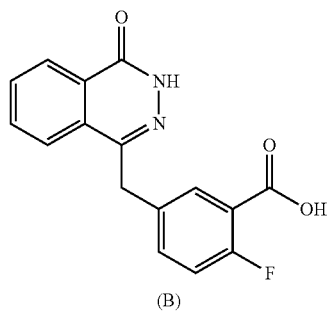

(B)

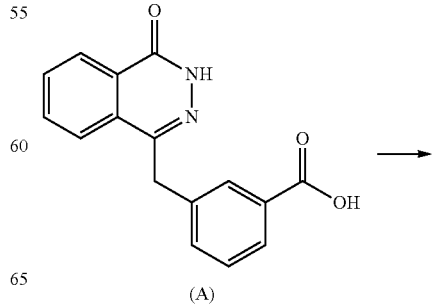

(A)

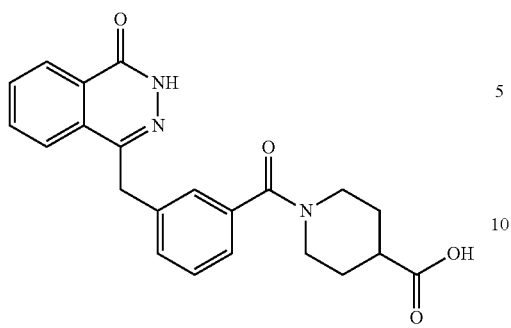

(C)

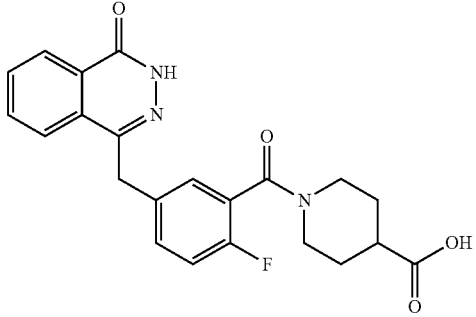

(D)

3-(4-Oxo-3,4-dihydrophthalazin-1-ylmethyl)benzoic acid (A)(7.0 g, 0.25 mol), ethyl isonipecotate (5 ml, 0.32 mol), 2-(1H-benzotriazol-1-yl)-1,1,3,3-tetramethyluronium hexafluorophosphate (HBTU) (12.3 g, 0.32 mol) and N,N-diisopropylethylamine (10.0 ml, 0.55 mol) were added to dimethylacetamide (40 ml) and stirred for 18 h. Water (100 ml) was added to the reaction mixture and the product was extracted into dichloromethane (4×50 ml). The combined organic layers were washed with water (3×100 ml), dried over MgSO₄, filtered and evaporated in vacuo to yield an oil. To a solution of the oil in tetrahydrofuran (100 ml) was added 10% aqueous sodium hydroxide solution (20 ml) and the reaction was stirred for 18 hours. The reaction was concentrated, washed with ethyl acetate (2×30 ml) and acidified with 2M HCl to pH 2. The aqueous layer was extracted with dichloromethane (2×100 ml), then the extracts were dried over MgSO₄, filtered and evaporated to yield 1-[3-(4-oxo-3,4-dihydrophthalazin-1-ylmethyl)benzoyl]piperidine-4-carboxylic acid (C) as a yellow solid (7.0 g, 65%), m/z [M+1]$^+$ 392 (96% purity), $\delta_H$ 1.3-1.8 (5H, m), 2.8-3.1 (4H, m), 4.4 (2H, s), 7.2-7.3 (1H, m), 7.3-7.4 (1H, m), 7.7-8.0 (5H, m), 8.2-8.3 (1H, m), 12.6 (1H, s).

d. 1-[2-Fluoro-5-(4-oxo-3,4-dihydrophthalazin-1-ylmethyl)benzoyl]piperidine-4-carboxylic acid (D)

2-Fluoro-5-(4-oxo-3,4-dihydrophthalazin-1-ylmethyl)benzoic acid (B) (3.1 g, 0.14 mol), ethyl isonipecotate (1.7 ml, 0.11 mol), 2-(1H-benzotriazol-1-yl)-1,1,3,3-tetramethyluronium hexafluorophosphate (HBTU) (5.1 g, 0.13 mol) and N,N-diisopropylethylamine (10.0 ml, 0.55 mol) were added to dimethylacetamide (15 ml) and stirred for 18 hours. Water (100 ml) was added to the reaction mixture and the product was extracted into dichloromethane (4×50 ml). The combined organic layers were, filtered, washed with water (3×100 ml), dried over MgSO₄, filtered and evaporated in vacuo to yield an orange oil. The oil was purified by flash chromatography (ethyl acetate) to yield 1-[2-fluoro-5-(4-oxo-3,4-dihydrophthalazin-1-ylmethyl)benzoyl]piperidine-4-carboxylic acid as the methyl ester (1.5 g, 33%, 96% purity). To a solution of the methyl ester in tetrahydrofuran:water (2:1, 40 ml) was added sodium hydroxide (0.3 g, 0.075 mol) and the reaction was stirred for 18 h. The reaction was concentrated, washed with ethyl acetate (2×20 ml) and acidified with 2M HCl to pH 2. The aqueous layer was extracted with dichloromethane (2×20 ml), and the combined extracts were dried over MgSO₄ and evaporated to yield 1-[3-(4-oxo-3,4-dihydrophthalazin-1-ylmethyl)benzoyl]piperidine-4-carboxylic acid (D) as a yellow solid (0.6 g, 65%), m/z [M+1]$^+$ 392 (96% purity)

Example 1 a. Synthesis of 4-[3-(piperazine-1-carbonyl)benzyl]-2H-phthalazin-1-one (1)

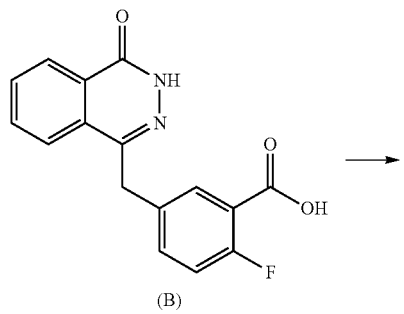

(B)

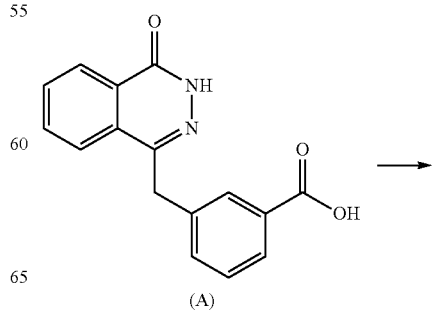

(A)

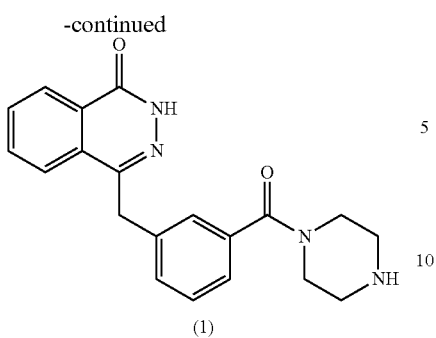

(1)

3-(4-Oxo-3,4-dihydrophthalazin-1-ylmethyl)benzoic acid (A) (5.0 g, 0.17 mol), tert-butyl 1-piperazinecarboxylate (3.9 g, 0.21 mol), 2-(1H-benzotriazol-1-yl)-1,1,3,3-tetramethyluronium hexafluorophosphate (HBTU) (8.6 g, 0.22 mol) and N,N-diisopropylethylamine (6.7 ml, 0.38 mol) were added to dimethylacetamide (40 ml) and stirred for 18 hours. Water (100 ml) was added and the reaction mixture was heated to 100° C. for 1 hour. The suspension was cooled to room temperature, filtered and dried to yield a white solid. The solid was dissolved in a solution of 6M HCl and ethanol (2:1, 50 ml) and stirred for 1 hour. The reaction was concentrated, basified with ammonia to pH 9, and the product was extracted into dichloromethane (2×50 ml). The combined organic layers were washed with water (2×50 ml), dried over MgSO$_4$, and evaporated in vacuo to yield 4-[3-(piperazine-1-carbonyl)benzyl]-2H-phthalazin-1-one (1) as a yellow crystalline solid (4.0 g, 77%); m/z [M+1]$^+$ 349 (97% purity), $\delta_H$ 2.6-3.8 (8H, m), 4.4 (2H, s), 7.2-7.5 (4H, m), 7.7-8.0 (3H, m), 8.2-8.3 (1H, m), 12.6 (1H, s)

b. Synthesis of 4-[4-Fluoro-3-(piperazine-1-carbonyl)benzyl]-2H-phthalazin-1-one (2)

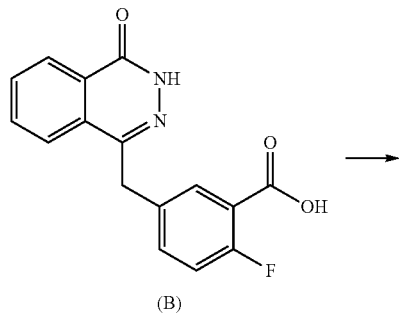

(B)

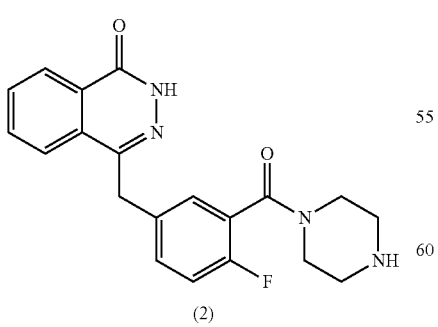

(2)

The synthesis was carried out according to the method described in (a) above using 2-fluoro-5-(4-oxo-3,4-dihydrophthalazin-1-ylmethyl)benzoic acid (B) to yield 4-[4-fluoro-3-(piperazine-1-carbonyl)benzyl]-2H-phthalazin-1-one (2) as a white crystalline solid (4.8 g, 76%); m/z [M+1]$^+$ 367 (97% purity), $\delta_H$ 2.6-3.8 (8H, m), 4.4 (2H, s), 7.2-7.5 (3H, m), 7.7-8.0 (3H, m), 8.2-8.3 (1H, m), 12.6 (1H, s).

c. Synthesis of 4-[3-([1,4]diazepane-1-carbonyl)benzyl]-2H-phthalazin-1-one (3)

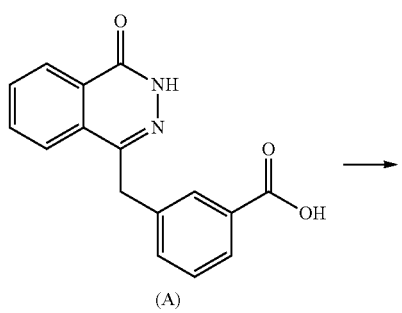

(A)

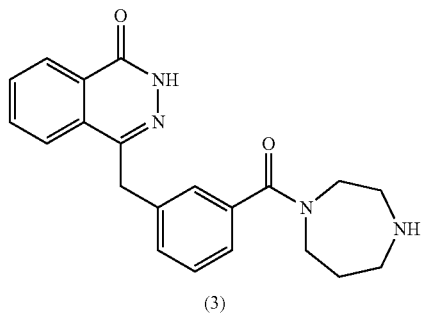

(3)

The synthesis was carried out according to the method described in (a) above using 3-(4-oxo-3,4-dihydrophthalazin-1-ylmethyl)benzoic acid (A) and tert-butyl 1-homopiperazine carboxylate to yield 4-[3-([1,4]diazepane-1-carbonyl)benzyl]-2H-phthalazin-1-one (3) as a grey crystalline solid (5.3 g, 97%); m/z [M+1]$^+$ 363 (97% purity); $\delta_H$ 2.6-3.8 (10H, m), 4.4 (2H, s), 7.2-7.5 (4H, m), 7.7-8.0 (3H, m), 8.2-8.3 (1H, m), 12.6 (1H, s).

d. Synthesis of 4-[3-([1,4]diazepane-1-carbonyl)-4-fluorobenzyl]-2H-phthalazin-1-one (4)

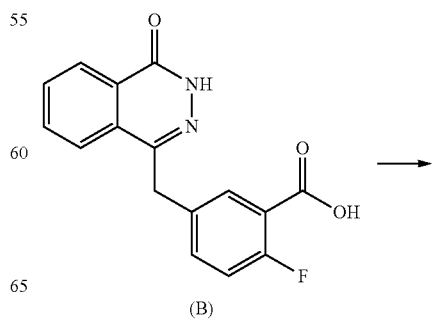

(B)

-continued

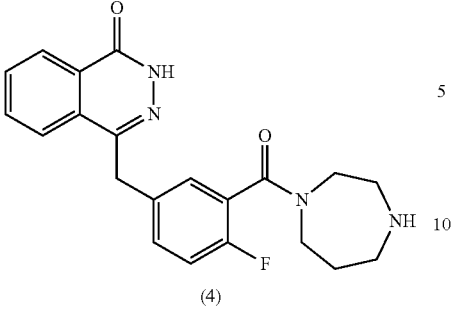

(4)

The synthesis was carried out according to the method described in (a) above using 2-fluoro-5-(4-oxo-3,4-dihydrophthalazin-1-ylmethyl)benzoic acid (B) and tert-butyl 1-homopiperazinecarboxylate to yield 4-[3-([1,4]diazepane-1-carbonyl)benzyl]-2H-phthalazin-1-one (4) as a yellow crystalline solid (5.3 g, 68%); m/z [M+1]$^+$ 381 (97% purity); $\delta_H$ 2.6-3.8 (10H, m), 4.4 (2H, s), 7.2-7.5 (3H, m), 7.7-8.0 (3H, m), 8.2-8.3 (1H, m), 12.6 (1H, s).

Example 2 a. 4-{3-[4-(6-Chlorobenzothiazol-2-yl)-1,4-diazepan-1-ylcarbonyl]benzyl}-1(2H)-phthalazinone

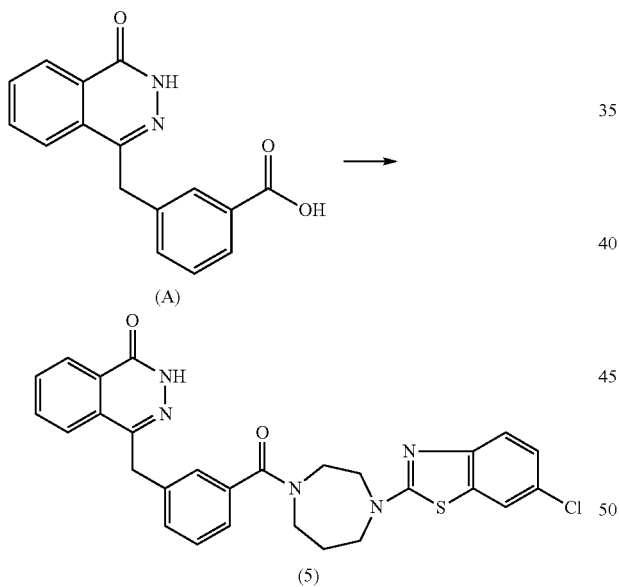

2-(1H-Benzotriazol-1-yl)-1,1,3,3-tetramethyluronium tetrafluoroborate (150 mg, 0.47 mmol), diisopropylethylamine (102 mg, 0.8 mmol) and 6-chloro-2-(1,4-diazepan-1-yl)-1,3-benzothiazole (115 mg, 0.43 mmol) were added sequentially at ambient temperature to a stirred solution of 3-(4-oxo-3,4-dihydrophthalazin-1-ylmethyl)benzoic acid (A) (100 mg, 0.36 mmol) in dry dimethylacetamide (1 ml), the mixture was stirred at ambient temperature for 1 hour and allowed to stand at ambient temperature for 16 hours, then it was added dropwise to stirred cold water (10 ml). After 30 minutes, the resulting solid was collected by filtration, washed with water (2×1 ml) and hexane (1 ml), dried in vacuo and purified using preparative HPLC to give the desired compound (5)(166 mg) as a grey solid; HPLC purity 90%; HPLC Retention time 4.21 minutes; m/z (M+H)$^{+\cdot}$ 530.

b. The following compounds were synthesised in a manner analogous to that described in (a) above, but using appropriate alternative amine starting materials.

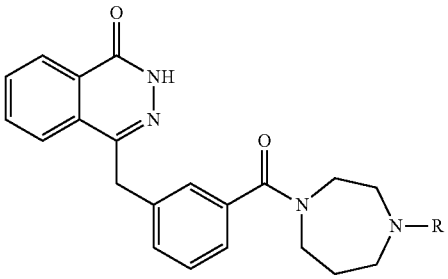

| Compound | R | LC RT (minutes) | M + 1 | LC Purity (%) |
|---|---|---|---|---|
| 6 | ![F, CF3 pyridine] | 4.18 | 508 | 90 |
| 7 | ![CH2-C6H3(F)(Br)] | 3.22 | 551 | 90 |
| 8 | ![CF3 pyridine] | 4.13 | 508 | 90 |
| 9 | ![pyrimidine-CH2CH2-CH3] | 3.95 | 483 | 90 |
| 10 | ![CN pyridine] | 3.79 | 465 | 90 |

-continued

| Compound | R | LC RT (minutes) | M + 1 | LC Purity (%) |
|---|---|---|---|---|
| 11 | *—O—C(CH₃)₃ (tert-butyl carbonate) | 3.76 | 406 | 90 |
| 219 | *—CH₂CH₂OH | 2.80 | 407 | 90 |

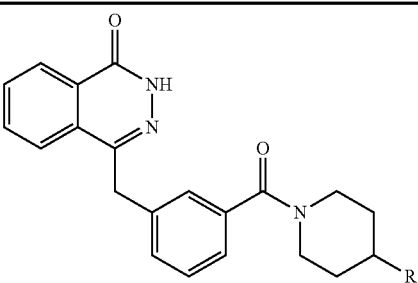

| Compound | R | LC RT (minutes) | M + 1 | LC Purity (%) |
|---|---|---|---|---|
| 12 (Note 1) | 5-(trifluoromethyl)pyridin-2-yl | 3.56 | 494 | 100 |
| 13 | 5-cyanopyridin-2-yl | 3.71 | 451 | 90 |
| 14 | 2-nitro-4-(trifluoromethyl)phenyl | 4.39 | 538 | 90 |
| 15 | 4-nitrobenzoyl | 3.66 | 498 | 90 |
| 16 | 5-(benzyloxy)pyrimidin-2-yl | 4.33 | 533 | 90 |

-continued (structure: 4-{3-[piperidin-1-ylcarbonyl]benzyl}-1(2H)-phthalazinone with R on piperidine 4-position)

| Compound | R | LC RT (minutes) | M + 1 | LC Purity (%) |
|---|---|---|---|---|
| 17 | 3-(4-chlorophenyl)-1,2,4-oxadiazol-5-yl | 4.64 | 526 | 90 |
| 18 | 4-methoxybenzoyl | 3.99 | 482 | 90 |
| 19 | benzoyl | 4.00 | 452 | 90 |
| 20 | 4-methylbenzoyl | 4.15 | 466 | 90 |

Note 1:
12 did not require purification via preparative scale HPLC - the product from the reaction was essentially pure.

Example 3 a. 4-{3-[4-(4-fluorophenyl)piperazin-1-ylcarbonyl]benzyl}-1(2H)-phthalazinone (21)

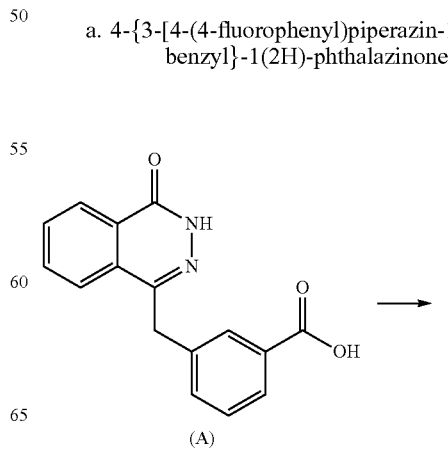

(A)

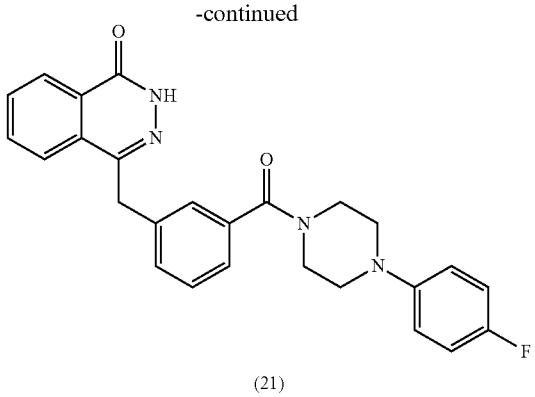

(21)

2-(1H-Benzotriazol-1-yl)-1,1,3,3-tetramethyluronium tetrafluoroborate (150 mg, 0.47 mmol), diisopropylethylamine (102 mg, 0.8 mmol) and 1-(4-fluorophenyl)piperazine (65 mg, 0.47 mmol) were added sequentially at ambient temperature to a stirred solution of 3-(4-oxo-3,4-dihydrophthalazin-1-ylmethyl)benzoic acid (A) (100 mg, 0.36 mmol) in dry dimethylacetamide (1 ml), the mixture was stirred at ambient temperature for 4 hours and allowed to stand at ambient temperature for 16 hours, then it was added dropwise to stirred cold water (10 ml). After 30 minutes, the resulting solid was collected by filtration, washed with water (2×1 ml) and hexane (1 ml), dried in vacuo and purified using preparative HPLC to give 4-{3-[4-(4-fluorophenyl)piperazin-1-ylcarbonyl]benzyl}-1(2H)-phthalazinone (21) (76 mg) as a cream solid; m/z (M+H)$^{+\cdot}$ 443; HPLC Purity 90%; HPLC Retention time 4.00 minutes.

b. The following compounds were synthesised in a manner analogous to that described in (a) above, but using appropriate alternative amine starting materials.

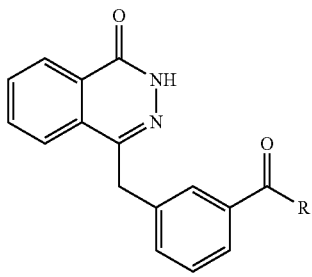

| Compound | R | LC RT (minutes) | M + 1 | LC Purity (%) |
|---|---|---|---|---|
| 22 | 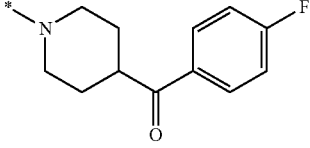 [SMILES: *N1CCC(C(=O)c2ccc(F)cc2)CC1] | 4.00 | 470 | 90 |
| 23 | 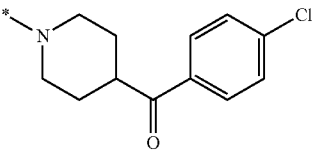 [SMILES: *N1CCC(C(=O)c2ccc(Cl)cc2)CC1] | 4.26 | 486 | 90 |
| 24 | 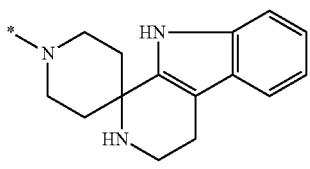 [SMILES: *N1CCC2(CC1)NCCc1c2[nH]c2ccccc12] | 3.18 | 504 | 85 |
| 25 | 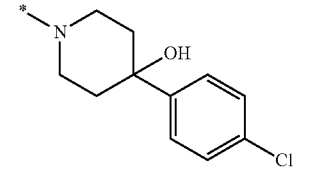 [SMILES: *N1CCC(O)(c2ccc(Cl)cc2)CC1] | 3.78 | 473 | 90 |

-continued
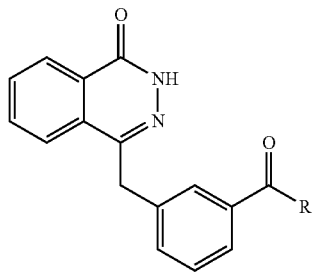
| Compound | R | LC RT (minutes) | M + 1 | LC Purity (%) |
|---|---|---|---|---|
| 26 | | 4.46 | 583 | 90 |
| 27 | | 4.96 | 509 | 90 |
| 28 | | 3.73 | 511 | 90 |
| 29 | | 3.78 | 553 | 90 |
| 30 | | 3.71 | 459 | 90 |
| 31 | | 3.94 | 546 | 90 |

-continued

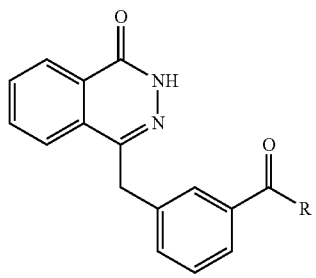

| Compound | R | LC RT (minutes) | M + 1 | LC Purity (%) |
|---|---|---|---|---|
| 32 | | 3.84 | 485 | 90 |
| 33 | | 4.37 | 552 | 90 |
| 34 | | 3.77 | 485 | 90 |
| 220 (Note 2) | | 2.89 | 440 | 100 |

Note 2:
220 did not require purification via preparative scale HPLC-the product from the reaction was essentially pure.

Example 4

1-[3-(4-Oxo-3,4-dihydro-phthalazin-1-ylmethyl)-benzoyl]-piperidine-4-carboxylic acid (C) (0.24 mmol) was added to a solution of the appropriate amine (0.2 mmol) in dimethylacetamide (2 ml). 2-(1H-Benzotriazole-1-yl)-1,1,3,3-tetramethyluronium hexafluorophosphate (0.3 mmol) and Hunigs base (0.4 mmol) were then added and the reaction was stirred at room temperature for 16 hours. The reaction mixtures were then purified by preparative HPLC.

The compounds synthesised are set out below.

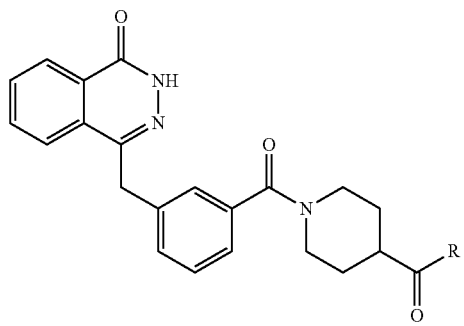
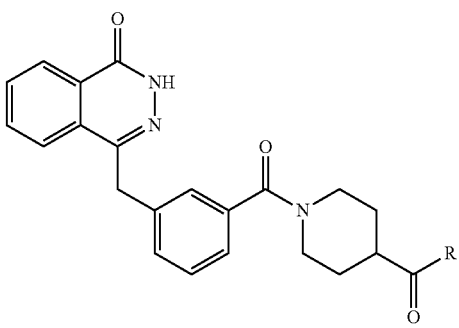
| Compound | R | LC RT (minutes) | M + 1 | LC Purity (%) |
|---|---|---|---|---|
| 35 | *—N(CH₂Ph)₂ | 4.39 | 572 | 90 |
| 36 | *—N(CH₃)(CH₂Ph) | 3.71 | 496 | 90 |
| 37 | 2-methylpiperidin-1-yl | 3.63 | 474 | 80 |
| 38 | 4-methylpiperidin-1-yl | 3.76 | 474 | 90 |
| 39 | *—NH-CH₂CH₂-(2-thienyl) | 3.56 | 502 | 90 |
| 40 | 6,7-dimethoxy-1,2,3,4-tetrahydroisoquinolin-2-yl | 3.58 | 568 | 90 |
| Compound | R | LC RT (minutes) | M + 1 | LC Purity (%) |
|---|---|---|---|---|
| 41 | 1,2,3,4-tetrahydroisoquinolin-2-yl | 3.81 | 508 | 90 |
| 42 | *—NH-(4-t-Bu-cyclohexyl) | 4.39 | 531 | 90 |
| 43 | piperidin-1-yl | 3.52 | 460 | 85 |
| 44 | *—NH-(indan-1-yl) | 3.77 | 508 | 90 |
| 45 | *—NH-CH₂-(2-thienyl) | 3.59 | 488 | 90 |
| 46 | *—NH-(4-methylcyclohexyl) | 3.83 | 488 | 90 |
| 47 | *—NH-CH₂-cyclohexyl | 3.85 | 488 | 90 |
| 48 | *—NH-CH₂-CH(CH₃)₂ | 3.47 | 448 | 90 |

49
-continued

50
-continued

| Compound | R | LC RT (minutes) | LC M+1 | Purity (%) |
|---|---|---|---|---|
| 49 | *—NH—CH₂-cyclopropyl | 3.36 | 446 | 90 |
| 50 | *—NH-(2-methylcyclohexyl) | 3.77 | 488 | 90 |
| 51 | *—N(CH₂CH=CH₂)₂ | 3.74 | 472 | 90 |
| 52 | *—NH-(1-ethynylcyclohexyl) | 3.82 | 498 | 90 |
| 53 | *—NH-cyclopentyl | 3.52 | 460 | 90 |
| 54 | *—NH—CH₂—CH(CH₃)—phenyl | 3.86 | 510 | 90 |
| 55 | *—NH-(2-(ethoxycarbonyl)cyclohexyl) | 3.75 | 546 | 90 |

| Compound | R | LC RT (minutes) | LC M+1 | Purity (%) |
|---|---|---|---|---|
| 56 | *—NH-(1-benzylpiperidin-4-yl) | 3.01 | 565 | 90 |
| 57 | *—NH—CH₂-(4-CF₃-phenyl) | 3.93 | 549 | 90 |
| 373 | *—N(piperazinyl)—CH(4-F-phenyl)₂ | 4.17 | 663 | 90 |
| 374 | *—N(piperazinyl)—CH₂-(benzo[d][1,3]dioxol-5-yl) | 3.08 | 595 | 90 |
| 375 | *—N(piperazinyl)-(2-methylphenyl) | 4.16 | 551 | 90 |
| 376 | *—N(piperazinyl)-(2,4-dimethylphenyl) | 4.3 | 565 | 90 |

51

-continued

[Structure: 4-[3-(piperidine-1-carbonyl)benzyl]-2H-phthalazin-1-one with R-C(=O) on piperidine 4-position]

| Compound | R | LC RT (minutes) | M + 1 | LC Purity (%) |
|---|---|---|---|---|
| 377 | *—N(piperazine)N-C6H4-Cl (para) | 4.1 | 571 | 90 |
| 378 | *—N(piperazine)N-C6H4-OMe (para) | 3.64 | 567 | 90 |
| 379 | *—N(piperazine)N-C6H4-C(=O)CH3 (para) | 3.62 | 579 | 90 |
| 380 | *—N(piperazine)N-C6H4-CF3 (meta) | 4.27 | 605 | 90 |
| 381 | *—N(piperazine)N-C6H4-F (ortho) | 3.89 | 555 | 90 |
| 382 | *—N(2-methylpiperazine)N-C6H4-CH3 (meta) | 3.84 | 565 | 90 |
| 383 | *—N(piperazine)N-(2-pyridyl) | 2.92 | 565 | 90 |
| 384 | *—N(piperazine)N-cyclohexyl | 3.02 | 543 | 90 |

Example 5

The appropriate sulphonyl chloride (0.24 mmol) was added to a solution of 4-[3-(piperazine-1-carbonyl)benzyl]-2H-phthalazin-1-one (1) (0.2 mmol) in dichloromethane (2 ml). Hunigs base (0.4 mmol) was then added and the reaction was stirred at room temperature for 16 hours. The reaction mixtures were then purified by preparative HPLC.

The compounds synthesised are set out below.

52

[Structure: 4-[3-(piperazine-1-carbonyl)benzyl]-2H-phthalazin-1-one with R-SO2- on distal piperazine nitrogen]

| Compound | R | LC RT (minutes) | M + 1 | LC Purity (%) |
|---|---|---|---|---|
| 58 | benzyl (*-CH2-C6H5) | 3.85 | 504 | 90 |
| 59 | *-CH(CH3)- (ethyl, shown as CH3 branched) | 3.44 | 442 | 90 |
| 60 | 2-CF3-C6H4- | 4.09 | 558 | 90 |
| 61 | 2-Cl-C6H4- | 3.93 | 525 | 90 |
| 62 | 5-Cl-1,3-dimethylpyrazol-4-yl | 3.73 | 543 | 90 |
| 63 | 2,4,6-trimethylphenyl | 4.38 | 532 | 90 |
| 64 | 3,5-dimethylisoxazol-4-yl | 3.76 | 509 | 90 |
| 65 | *-CH2CH2CH2CH3 (n-butyl) | 3.82 | 470 | 90 |

Example 6

The appropriate acid chloride (0.24 mmol) was added to a solution of 4-[3-(piperazine-1-carbonyl)benzyl]-2H- phthalazin-1-one (1) (0.2 mmol) in dichloromethane (2 ml). Hunigs base (0.4 mmol) was then added and the reaction was stirred at room temperature for 16 hours. The reaction mixtures were then purified by preparative HPLC.

The compounds synthesised are set out below.

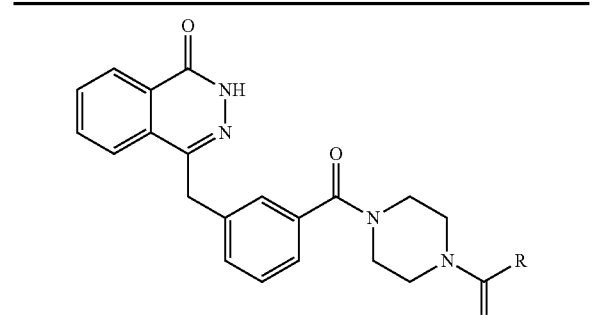

| Compound | R | LC RT (minutes) | M + 1 | LC Purity (%) |
|---|---|---|---|---|
| 66 | *-C6H4-C6H5 (biphenyl) | 4.04 | 530 | 85 |
| 67 | *-cyclohexyl | 3.71 | 460 | 90 |
| 68 | *-(2-Cl,4-F-phenyl) | 3.69 | 506 | 90 |
| 69 | *-CH2-O-C(O)-CH3 | 3.19 | 450 | 85 |
| 70 | *-C(CH3)2-O-C(O)-CH3 | 3.44 | 478 | 90 |
| 71 | *-(4-OCF3-phenyl) | 3.94 | 538 | 90 |
| 72 | *-CH(phenyl)-O-C(O)-CH3 | 3.68 | 526 | 90 |
| 73 | *-CH2-O-CH2-CH3 | 3.6 | 464 | 90 |

-continued

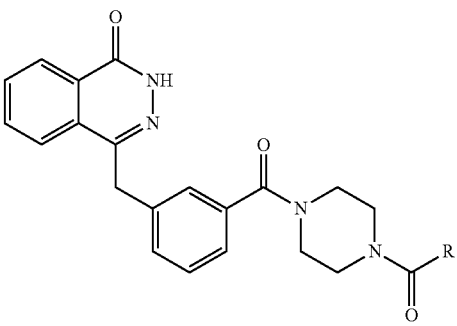

| Compound | R | LC RT (minutes) | M + 1 | LC Purity (%) |
|---|---|---|---|---|
| 74 | 2,5-dimethylfuran-3-yl | 3.63 | 472 | 90 |
| 75 | 5-methyl-3-phenylisoxazol-4-yl | 3.73 | 535 | 80 |
| 76 | 6-fluoro-4H-benzo[d][1,3]dioxin-8-yl | 3.49 | 530 | 90 |
| 77 | benzo[c][1,2,5]thiadiazol-5-yl | 3.5 | 512 | 85 |
| 78 | 5-methylisoxazol-3-yl | 3.52 | 459 | 90 |
| 79 | *-(2-OC(O)phenyl-phenyl) | 4.01 | 588 | 90 |
| 80 | *-CH2-CH3 | 4.05 | 406 | 90 |

55
-continued

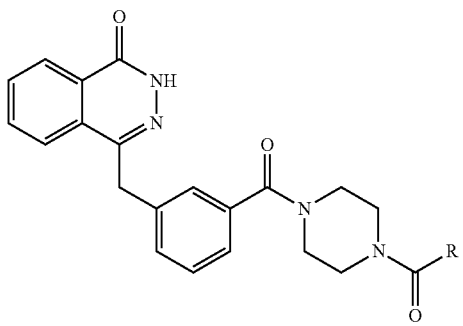

| Compound | R | LC RT (minutes) | M + 1 | LC Purity (%) |
|---|---|---|---|---|
| 81 | *-CH2-C6H4-NO2 (3-nitrobenzyl) | 3.84 | 513 | 90 |
| 82 | *-bicyclopentyl-phenyl | 4.07 | 520 | 90 |
| 83 | *-(4-methyl-1-(3,5-bis(trifluoromethyl)phenyl)-1H-1,2,3-triazol-5-yl) | 4.41 | 671 | 90 |
| 84 | *-(5-methyl-1-(4-chlorophenyl)-1H-imidazol-4-yl) | 3.62 | 582 | 90 |
| 85 | *-(1-(4-methylphenyl)cyclopropyl) | 3.82 | 508 | 90 |
| 86 | *-CH2-(1H-indol-1-yl) | 3.81 | 507 | 90 |
| 87 | *-(isoxazol-5-yl) | 3.33 | 445 | 90 |

56
-continued

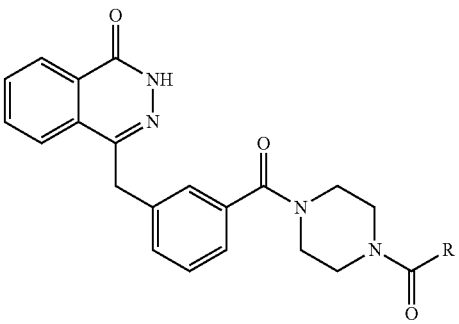

| Compound | R | LC RT (minutes) | M + 1 | LC Purity (%) |
|---|---|---|---|---|
| 88 | *-CH2CH2-S-(benzothiazol-2-yl) | 4.08 | 571 | 90 |
| 89 | *-(bicyclo[4.2.0]octa-1,3,5-trien-7-yl) | 3.67 | 480 | 90 |
| 90 | *-CH2CH2CH2-(2-methyl-1-oxo-1,2-dihydroisoquinolin-3-yl) | 3.54 | 577 | 90 |
| 91 | *-(benzo[d][1,3]dioxol-5-yl) | 3.49 | 498 | 90 |
| 92 | *-CH2-(2,4,6-trimethylphenyl) | 4.04 | 510 | 90 |
| 93 | *-CH2CH2-(3-methoxyphenyl) | 3.75 | 512 | 90 |
| 94 | *-CH2CH2-phenyl | 3.67 | 482 | 90 |

-continued
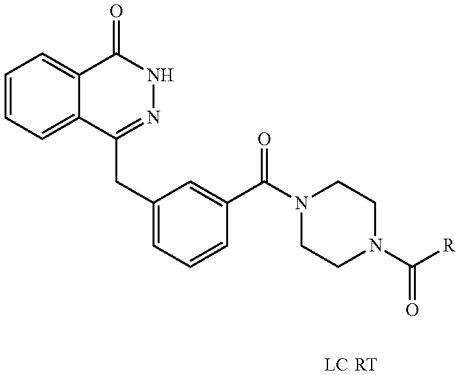
| Compound | R | LC RT (minutes) | M + 1 | LC Purity (%) |
|---|---|---|---|---|
| 95 | 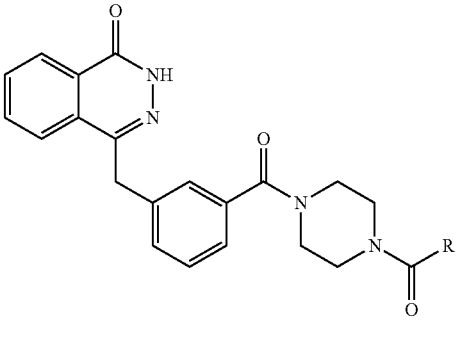 | 3.54 | 474 | 90 |
| 96 | 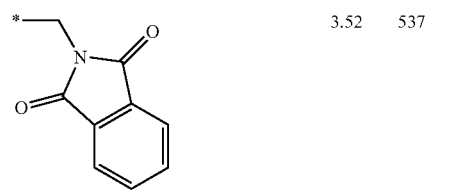 | 3.52 | 537 | 90 |
| 97 | 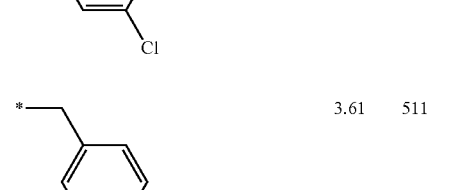 | 4.13 | 475 | 90 |
| 98 | 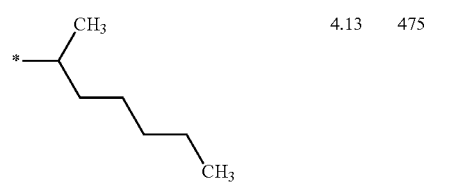 | 3.8 | 512 | 85 |
| 99 |  | 4.09 | 544 | 90 |
| 100 | 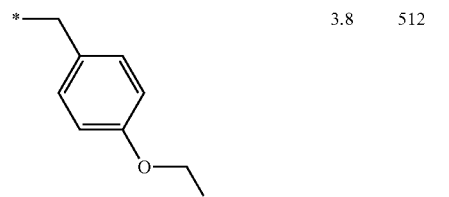 | 3.63 | 486 | 90 |
-continued
| Compound | R | LC RT (minutes) | M + 1 | LC Purity (%) |
|---|---|---|---|---|
| 101 | 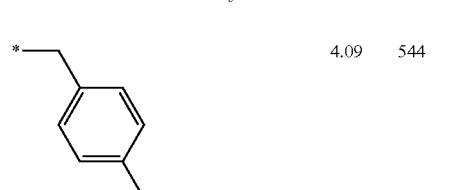 | 3.91 | 502 | 90 |
| 102 |  | 3.61 | 511 | 90 |
| 103 | 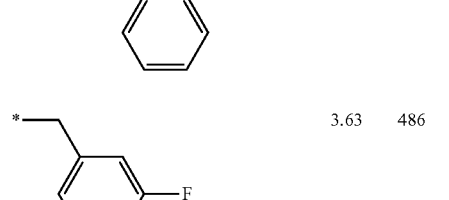 | 3.57 | 474 | 90 |
| 104 | 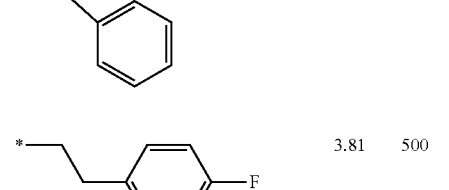 | 3.67 | 504 | 90 |
| 105 | | 4.02 | 508 | 90 |
| 106 | | 3.81 | 500 | 90 |

-continued
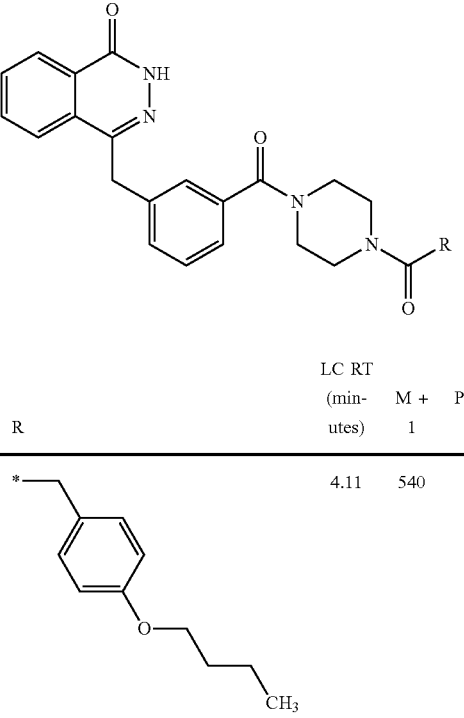
| Compound | R | LC RT (minutes) | M + 1 | LC Purity (%) |
|---|---|---|---|---|
| 107 | 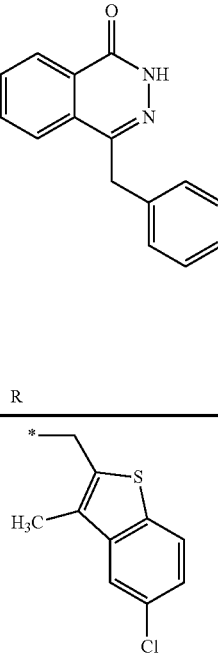 | 4.11 | 540 | 90 |
| 108 | 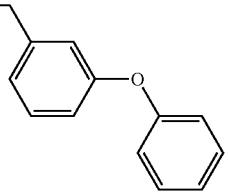 | 4.19 | 560 | 90 |
| 109 | 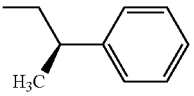 | 3.61 | 468 | 90 |
| 110 | 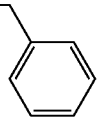 | 3.69 | 582 | 90 |
| 111 | 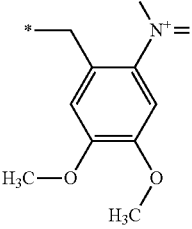 | 3.85 | 549 | 85 |
-continued
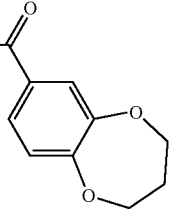
| Compound | R | LC RT (minutes) | M + 1 | LC Purity (%) |
|---|---|---|---|---|
| 112 | 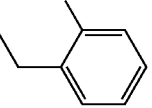 | 4.37 | 573 | 90 |
| 113 | 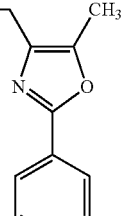 | 3.84 | 496 | 90 |
| 114 | 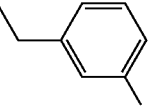 | 3.62 | 573 | 90 |
| 115 | 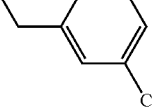 | 3.72 | 500 | 90 |
| 116 | 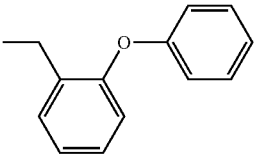 | 3.8 | 500 | 85 |
| 117 | | 3.9 | 496 | 90 |
| 118 | | 4.03 | 560 | 90 |

61
-continued

| Compound | R | LC RT (minutes) | M + 1 | LC Purity (%) |
|---|---|---|---|---|
| 119 | *-CH2-C6H4-O-C6H5 (4-phenoxybenzyl) | 4.16 | 560 | 90 |
| 120 | *-3-fluorophenyl | 4.71 | 472 | 80 |
| 121 | *-(1-methyl-3-trifluoromethyl-pyrazol-4-yl) | 3.47 | 526 | 90 |
| 122 | *-(5-(3-trifluoromethylphenoxy)-1,3-dimethyl-pyrazol-4-yl) | 3.78 | 632 | 90 |
| 123 | *-(5-chloro-1,3-dimethyl-pyrazol-4-yl) | 3.27 | 506 | 90 |

62
-continued

| Compound | R | LC RT (minutes) | M + 1 | LC Purity (%) |
|---|---|---|---|---|
| 124 | *-(1-methyl-3-phenyl-thieno[2,3-c]pyrazol-5-yl) | 3.92 | 590 | 90 |
| 125 | *-(4-(4-chlorophenyl)-1-(4-trifluoromethyl-thiazol-2-yl)-pyrazol-5-yl) | 4.76 | 706 | 90 |
| 126 | *-(2-phenyl-thiazol-5-yl) | 4.27 | 605 | 90 |
| 127 | *-(4-methyl-2-(thien-2-yl)-thiazol-5-yl) | 3.71 | 557 | 90 |
| 128 | *-(4-methyl-2-phenyl-thiazol-5-yl) | 3.98 | 551 | 90 |

-continued
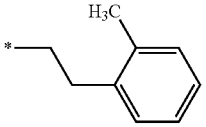 [SMILES: *CCc1ccccc1F]
| Compound | R | LC RT (minutes) | M + 1 | LC Purity (%) |
|---|---|---|---|---|
| 129 | 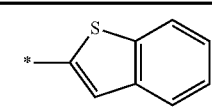 | 3.9 | 496 | 90 |
| 130 | 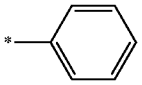 [SMILES: *c1ccccc1] | 3.57 | 454 | 90 |
| 131 | 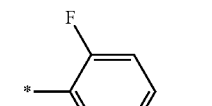 | 3.21 | 450 | 90 |
| 132 | 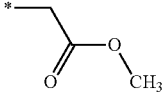 | 3.61 | 446 | 90 |
| 133 | 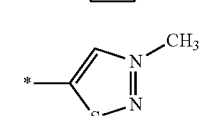 | 3.39 | 418 | 85 |
| 134 |  | 3.81 | 494 | 90 |
| 135 | 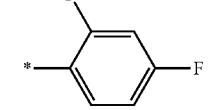 | 3.31 | 418 | 90 |
| 136 | 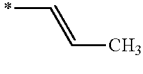 | 3.38 | 444 | 90 |
| 137 | 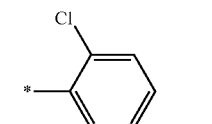 | 3.56 | 506 | 85 |
| 138 | 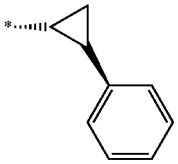 | 3.48 | 484 | 90 |
-continued
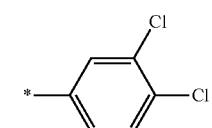
| Compound | R | LC RT (minutes) | M + 1 | LC Purity (%) |
|---|---|---|---|---|
| 139 |  | 3.84 | 510 | 90 |
| 140 | 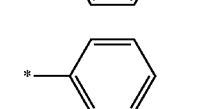 | 3.56 | 472 | 90 |
| 141 | 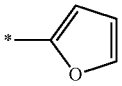 | 3.34 | 476 | 90 |
| 142 | 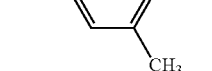 | 3.56 | 490 | 90 |
| 143 | 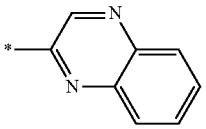 [SMILES: *c1cnc2ccccc2n1] | 3.53 | 488 | 90 |
| 144 |  | 3.99 | 523 | 90 |
| 145 | 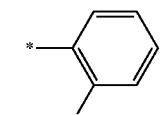 | 3.7 | 468 | 90 |
| 192 | *—CH$_3$ | 3.11 | 392 | 90 |
| 350 |  | 3.16 | 462 | 90 |
| 351 |  | 2.77 | 474 | 90 |

Example 7

The appropriate isocyanate (0.24 mmol) was added to a solution of 4-[3-(piperazine-1-carbonyl)benzyl]-2H-phthalazin-1-one (1) (0.2 mmol) in dichloromethane (2 ml). The reaction was stirred at room temperature for 16 hours. The reaction mixtures were then purified by preparative HPLC.

The compounds synthesised are set out below.

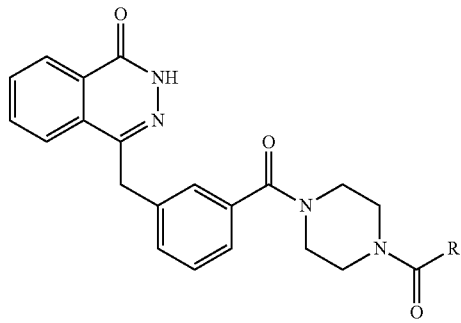

| Compound | R | LC RT (minutes) | M + 1 | LC Purity (%) |
|---|---|---|---|---|
| 146 | *—NH—CH(CH₃)₂ | 3.34 | 435 | 85 |
| 147 | *—NH—(3-methylphenyl) | 3.76 | 483 | 90 |
| 148 | *—NH—C(CH₃)₃ | 3.49 | 449 | 90 |
| 149 | *—NH—(2-fluorophenyl) | 3.57 | 487 | 90 |
| 150 | *—NH—(3-trifluoromethylphenyl) | 4.03 | 537 | 90 |
| 151 | *—NH—(1-naphthyl) | 3.77 | 519 | 85 |
| 152 | *—NH—(3-fluorophenyl) | 3.72 | 487 | 90 |

-continued
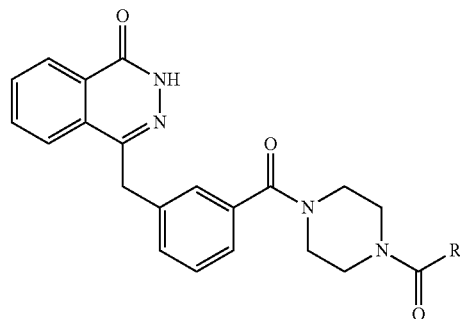
| Compound | R | LC RT (minutes) | M + 1 | LC Purity (%) |
|---|---|---|---|---|
| 153 | *—NH—(2,4-difluorophenyl) | 3.57 | 505 | 90 |
| 154 | *—NH—(4-CF₃-phenyl) | 4.08 | 537 | 80 |
| 155 | *—NH—(2-CH₃-phenyl) | 3.68 | 497 | 85 |
| 156 | *—NH—(4-OCF₃-phenyl) | 4.03 | 553 | 90 |
| 157 | *—NH—(3,5-dimethylphenyl) | 3.93 | 497 | 90 |
| 158 | *—NH—(3-CN-phenyl) | 3.62 | 494 | 90 |

-continued
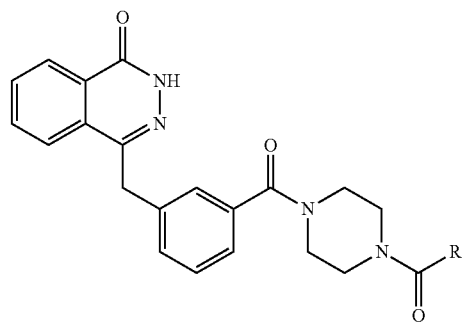
| Compound | R | LC RT (minutes) | M + 1 | LC Purity (%) |
|---|---|---|---|---|
| 159 | *—NH—CH2CH2—phenyl | 3.68 | 497 | 90 |
| 160 | *—NH—cyclohexyl | 3.73 | 475 | 90 |
| 161 | *—NH—(2-ethoxyphenyl) | 3.9 | 513 | 90 |
| 162 | *—NH—(4-isopropylphenyl) | 4.11 | 511 | 90 |
| 163 | *—NH—CH2—phenyl | 3.58 | 483 | 90 |
| 164 | *—NH—CH2—(2-chlorophenyl) | 3.71 | 517 | 90 |
| 165 | *—NH—CH2CH2CH3 | 3.34 | 435 | 85 |

-continued
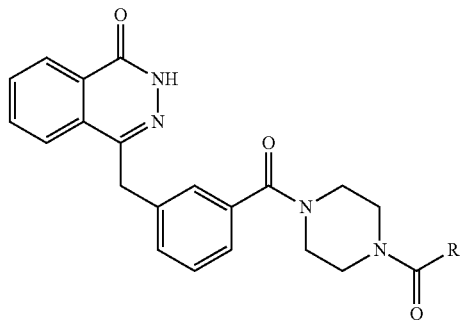
| Compound | R | LC RT (minutes) | M + 1 | LC Purity (%) |
|---|---|---|---|---|
| 166 | *—NH—CH₂—C₆H₄—CH₃ (4-methylbenzyl) | 3.71 | 497 | 90 |
| 167 | *—NH—CH₂—C₆H₄—OCH₃ (4-methoxybenzyl) | 3.56 | 513 | 90 |
| 168 | *—NH—CH₂—C₆H₃(2-Cl)(4-Cl) | 4.04 | 552 | 90 |
| 169 | *—NH—CH(CH₃)—(1-naphthyl) | 4 | 547 | 90 |
| 170 | *—NH—CH(iPr)—C(O)OCH₃ (methyl valinate) | 3.54 | 507 | 90 |
| 171 | *—NH—C(O)—C₆H₅ (benzamide) | 3.42 | 497 | 90 |
| 172 | *—NH—CH₂—C₆H₃(3-Cl)(4-Cl) | 3.95 | 552 | 90 |
| 173 | *—NH—C₆H₄(3-C(O)OCH₂CH₃) | 3.79 | 541 | 85 |

-continued
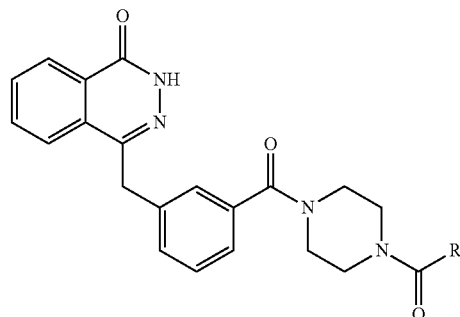
| Compound | R | LC RT (minutes) | M + 1 | LC Purity (%) |
|---|---|---|---|---|
| 174 | *—NH—(2,5-dimethoxyphenyl) | 3.66 | 529 | 90 |
| 175 | *—NH—(2-(methoxycarbonyl)phenyl) | 3.92 | 527 | 85 |
| 176 | *—NH—(3-(methoxycarbonyl)phenyl) | 3.62 | 527 | 90 |
| 177 | *—NH—(4-(butoxycarbonyl)phenyl) | 4.28 | 569 | 90 |

-continued

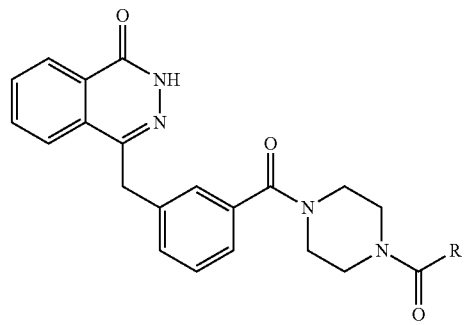

| Compound | R | LC RT (minutes) | M + 1 | LC Purity (%) |
|---|---|---|---|---|
| 178 | *—NH—(4-piperidinyl)-N-C(O)O-CH2-phenyl | 3.81 | 610 | 90 |
| 352 | *—NH—CH(CH2Ph)—C(O)—O—CH3 | 3.73 | 555 | 90 |
| 353 | *—NH—(4-phenyl)—C(O)—O—CH2CH3 | 3.79 | 541 | 90 |

Example 8

The appropriate isothiocyanate (0.24 mmol) was added to a solution of 4-[3-(piperazine-1-carbonyl)benzyl]-2H-phthalazin-1-one (1) (0.2 mmol) in dichloromethane (2 ml). The reaction was stirred at room temperature for 16 hours. The reaction mixtures were then purified by preparative HPLC.

The compounds synthesised are set out below.

| Compound | R | LC RT (minutes) | M + 1 | LC Purity (%) |
|---|---|---|---|---|
| 179 | *—NH—(2-methoxyphenyl) | 3.68 | 515 | 90 |
| 180 | *—NH—CH2CH2—phenyl | 4.05 | 513 | 90 |
| 181 | *—NH—(CH2)3CH3 | 3.94 | 465 | 90 |
| 182 | *—NH—CH2—CH=CH2 | 3.55 | 449 | 90 |
| 183 | *—NH—(pentafluorophenyl) | 4.21 | 575 | 90 |
| 184 | *—NH—(4-methoxycarbonylphenyl) | 3.79 | 543 | 90 |
| 185 | *—NH—(2-ethoxycarbonylphenyl) | 4.28 | 557 | 85 |
| 186 | *—NH—(3-acetylphenyl) | 3.63 | 527 | 90 |
| 187 | *—NH—(4-dimethylaminophenyl) | 3.18 | 528 | 90 |
| 188 | *—NH—CH3 | 3.32 | 423 | 90 |
| 189 | *—NH—phenyl | 3.69 | 485 | 80 |
| 190 | *—NH—(4-methoxyphenyl) | 3.68 | 515 | 90 |

79
-continued

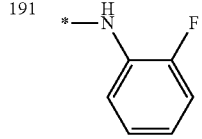

| Compound | R | LC RT (minutes) | M + 1 | LC Purity (%) |
|---|---|---|---|---|
| 191 | *—NH—(2-F-phenyl) | 3.72 | 503 | 90 |
| 354 | *—NH—C6H4—C(O)O—CH2CH3 | 4.67 | 542 | 90 |

80
-continued

| Compound | R | LC RT (minutes) | M + 1 | LC Purity (%) |
|---|---|---|---|---|
| 355 | *—NH—C6H4—C(O)O—CH3 | 3.96 | 543 | 90 |

Example 9

3-(4-Oxo-3,4-dihydrophthalazin-1-ylmethyl)benzoic acid (A) (0.24 mmol) was added to a solution of the appropriate amine (0.2 mmol) in dimethylacetamide (2 ml). 2-(1H-Benzotriazol-1-yl)-1,1,3,3-tetramethyluronium hexafluorophosphate (0.3 mmol) and Hunigs base (0.4 mmol) were then added and the reaction was stirred at room temperature for 16 hours. The reaction mixtures were then purified by preparative HPLC.

The compounds synthesised are set out below.

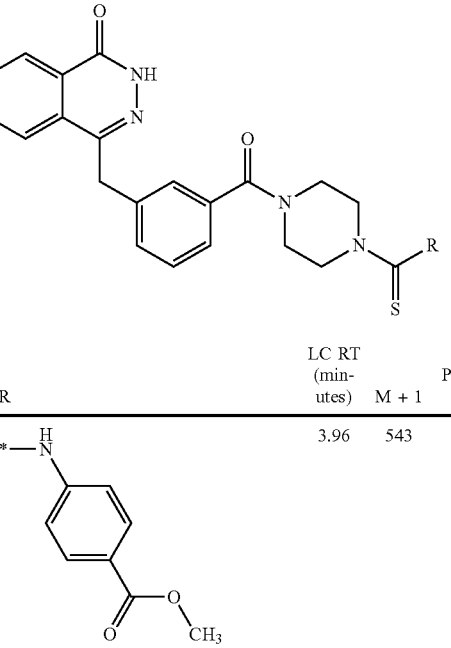

| Compound | R | LC RT (minutes) | M + 1 | LC Purity (%) |
|---|---|---|---|---|
| 193 | *—CH3 | 2.72 | 378 | 90 |
| 221 | *—CH2CH2—OH | 2.77 | 407 | 90 |

-continued
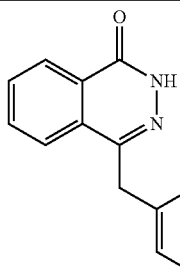
| Compound | R | LC RT (minutes) | M + 1 | LC Purity % |
|---|---|---|---|---|
| 194 | 2-pyridyl | 2.96 | 427 | 90 |
| 195 | 2-fluorophenyl | 4.08 | 444 | 90 |
| 196 | 3-methoxyphenyl | 3.9 | 456 | 95 |
| 197 | -C(O)O-C(CH$_3$)$_3$ | 3.83 | 450 | 95 |
| 198 | cyclohexyl | 2.98 | 432 | 90 |
| 199 | 3-methylphenyl | 4.17 | 440 | 90 |
| 200 | -CH$_2$C(O)NH-CH(CH$_3$)$_2$ | 2.9 | 449 | 90 |
| 201 | 4-chlorophenyl | 4.31 | 460 | 90 |
| 202 | 4-acetylphenyl | 3.63 | 468 | 90 |
| 203 | 4-methoxyphenyl | 3.78 | 456 | 90 |

-continued

| | | LC RT (minutes) | M + 1 | LC Purity % |
|---|---|---|---|---|
| 204 | *—C(=O)H | 3.08 | 378 | 90 |

| Compound | R | LC RT (minutes) | M + 1 | LC Purity % |
|---|---|---|---|---|
| 205 | *—N(piperidine)-piperidine | 2.88 | 432 | 90 |
| 206 | *—N(piperidine)-C(=O)O-CH₂CH₃ | 3.61 | 421 | 95 |
| 207 | *—N-tetrahydroisoquinoline | 3.96 | 397 | 90 |
| 356 | *—N(piperidine)-C(=O)-N(piperazine)-N-(2,3-dimethylphenyl) | 4.34 | 564 | 90 |
| 357 | *—N(piperidine)-C(=O)-N(piperazine)-N-(4-fluorophenyl) | 3.84 | 554 | 90 |

Example 10

2-Fluoro-5-(4-oxo-3,4-dihydrophthalazin-1-ylmethyl) benzoic acid (B) (0.24 mmol) was added to a solution of the appropriate amine (0.2 mmol) in dimethylacetamide (2 ml). 2-(1H-Benzotriazol-1-yl)-1,1,3,3-tetramethyluronium hexafluorophosphate (0.3 mmol) and Hunigs base (0.4 mmol) were then added and the reaction was stirred at room temperature for 16 hours. The reaction mixtures were then purified by preparative HPLC.

The compounds synthesised are set out below.

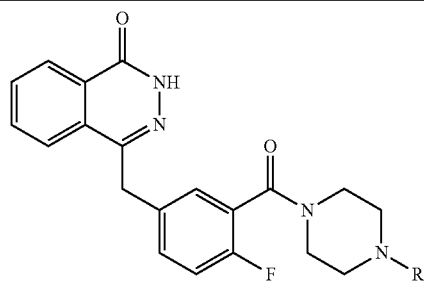
| Compound | R | LC RT (minutes) | M + 1 | LC Purity (%) |
|---|---|---|---|---|
| 208 | *—CH₃ | 2.8 | 396 | 90 |
| 359 | *—CH₂CH₂—OH | 2.78 | 425 | 85 |
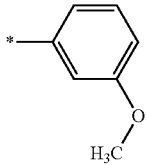
| Compound | R | LC RT (minutes) | M + 1 | LC Purity (%) |
|---|---|---|---|---|
| 209 | *-3-methoxyphenyl | 3.9 | 456 | 95 |
| 210 | *-C(O)O-C(CH₃)₃ | 3.97 | 467 | 90 |
| 211 | *-CH₂CH₂-O-CH₃ | 2.84 | 426 | 90 |
| 212 | *—CH₃ | 3.46 | 368 | 90 |
| 222 | *-2-fluorophenyl | 5.07 | 461 | 90 |
| 223 | *-3-trifluoromethylphenyl | 4.46 | 511 | 90 |
| 224 | *-cyclohexyl | 2.96 | 499 | 90 |
| 225 | *-pyrimidin-2-yl | 3.55 | 445 | 85 |
| 226 | *-3-methylphenyl | 4.19 | 457 | 90 |
| 227 | *-3,4-dimethylphenyl | 4.34 | 471 | 90 |
| 228 | *-CH₂-C(O)NH-CH(CH₃)₂ | 2.88 | 466 | 90 |
| 229 | *-4-hydroxyphenyl | 4.23 | 477 | 90 |
| 230 | *-4-methoxyphenyl | 4.03 | 473 | 90 |
| 231 | *-benzo[1,3]dioxol-5-yl | 3.07 | 500 | 90 |
| 232 | *-2-methoxyphenyl | 3.92 | 473 | 90 |
| 233 | *-C(O)H | 4.55 | 471 | 90 |
| 234 | *-3-chlorophenyl | 4.32 | 477 | 90 |
| 235 | *-phenyl | 3.94 | 443 | 90 |
| 236 | *-4-fluorophenyl | 4.03 | 461 | 90 |

| Compound | R | LC RT (minutes) | M + 1 | LC Purity (%) |
|---|---|---|---|---|
| 237 | *—CH2CH2—OH | 2.69 | 411 | 90 |
| 238 | *—CH2CH2—NMe2 | 2.76 | 438 | 90 |
| 239 | *—CH2—C(O)—N-morpholine | 2.77 | 494 | 90 |
| 240 | *—CH2-(3-pyridyl) | 2.91 | 444 | 90 |
| 358 | *—2,4-dimethylphenyl | 4.59 | 472 | 90 |

[Structure: 4-[(3-(R-carbonyl)-4-fluorophenyl)methyl]-2H-phthalazin-1-one]

| Compound | R | LC RT (minutes) | M + 1 | LC Purity (%) |
|---|---|---|---|---|
| 213 | *—N-piperidine-4-C(O)OCH2CH3 | 3.81 | 439 | 90 |
| 214 | *—N-tetrahydroisoquinoline | 3.95 | 415 | 90 |

[Structure: 4-[(3-((3-methyl-4-R-piperazin-1-yl)carbonyl)-4-fluorophenyl)methyl]-2H-phthalazin-1-one]

| Compound | R | LC RT (minutes) | M + 1 | LC Purity (%) |
|---|---|---|---|---|
| 360 | *—3-methylphenyl | 4.08 | 472 | 90 |

Example 11

An appropriate aldehyde (0.2 mmol) and 4-[3-(piperazine-1-carbonyl)benzyl]-2H-phthalazin-1-one (1)(0.24 mmol) were dissolved in dichloromethane (2 ml). Sodium triacetoxyborohydride (0.28 mmol) and glacial acetic acid (6.0 mmol) were then added and stirred at room temperature for 16 hours. The reaction mixtures were then purified by preparative HPLC.

The compounds synthesised are set out below.

[Structure: 4-[3-((4-R-piperazin-1-yl)carbonyl)benzyl]-2H-phthalazin-1-one]

| Compound | R | LC RT (minutes) | M + 1 | LC Purity (%) |
|---|---|---|---|---|
| 215 | *—CH2CH(CH3)2 | 2.89 | 406 | 90 |
| 216 | *—(CH2)3CH3 | 2.91 | 406 | 90 |
| 217 | *—CH2-(1-methylindol-3-yl) | 3.16 | 493 | 90 |
| 218 | *—CH2-(indol-3-yl) | 3.09 | 479 | 90 |
| 361 | *—CH2CH(CH3)CH2CH3 | 2.98 | 419 | 90 |
| 362 | *—CH2CH3 | 2.74 | 377 | 90 |
| 363 | *—(CH2)4CH3 | 3.04 | 419 | 90 |
| 364 | *—CH2CH2CH3 | 2.82 | 391 | 85 |

89
-continued

| Compound | R | LC RT (minutes) | M + 1 | LC Purity (%) |
|---|---|---|---|---|
| 365 |  | 2.84 | 403 | 90 |
| 366 |  | 2.96 | 419 | 90 |
| 367 |  | 3.15 | 445 | 90 |
| 368 |  | 3.04 | 419 | 90 |
| 369 |  | 2.75 | 391 | 85 |

Example 12

An appropriate aldehyde (0.2 mmol) and 4-[3-([1,4]diazepane-1-carbonyl)benzyl]-2H-phthalazin-1-one (4)(0.24 mmol) were dissolved in dichloromethane (2 ml). Sodium triacetoxyborohydride (0.28 mmol) and glacial acetic acid (6.0 mmol) were then added and stirred at room temperature for 16 hours. The reaction mixtures were then purified by preparative HPLC.

The compounds synthesised are set out below.

90

| Compound | R | LC RT (minutes) | M + 1 | LC Purity (%) |
|---|---|---|---|---|
| 241 |  | 2.9 | 437 | 90 |
| 242 |  | 3.05 | 451 | 90 |
| 243 |  | 2.84 | 409 | 90 |
| 244 |  | 3.12 | 465 | 90 |
| 245 |  | 3.16 | 451 | 90 |
| 246 |  | 2.86 | 423 | 90 |
| 247 |  | 2.89 | 435 | 90 |
| 248 |  | 3.04 | 451 | 90 |
| 249 |  | 3.23 | 477 | 90 |
| 250 |  | 3.09 | 451 | 90 |
| 370 |  | 2.80 | 423 | 90 |

Example 13

An appropriate aldehyde (0.2 mmol) and 4-[4-fluoro-3-(piperazine-1-carbonyl)benzyl]-2H-phthalazin-1-one (2) (0.24 mmol) were dissolved in dichloromethane (2 ml). Sodium triacetoxyborohydride (0.28 mmol) and glacial acetic acid (6.0 mmol) were then added and stirred at room temperature for 16 hours. The reaction mixtures were then purified by preparative HPLC.

The compounds synthesised are set out below.

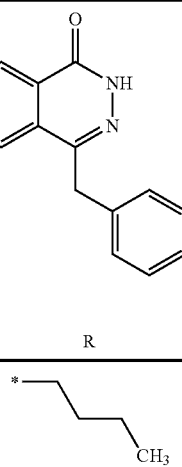

| Compound | R | LC RT (minutes) | M + 1 | LC Purity (%) |
|---|---|---|---|---|
| 251 | *—CH₂CH₂CH₂—CH₃ | 2.97 | 423 | 90 |
| 252 | *—CH₂—CH(CH₃)—CH₃ (with H₃C) | 3.06 | 437 | 90 |
| 253 | *—CH₂—CH₃ | 2.8 | 395 | 90 |
| 254 | *—CH₂—CH(CH₂CH₃)—CH₃ | 3.11 | 451 | 90 |
| 255 | *—CH₂CH₂CH₂CH₂—CH₃ | 3.09 | 437 | 90 |
| 256 | *—CH₂CH₂—CH₃ | 2.87 | 409 | 90 |
| 257 | *—cyclopropyl | 2.89 | 421 | 90 |
| 258 | *—CH₂—C(CH₃)₃ | 3.01 | 437 | 85 |
| 259 | *—CH₂—cyclohexyl | 3.14 | 463 | 90 |

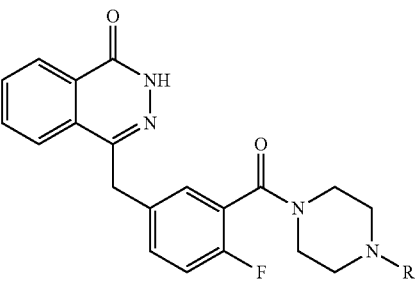

| Compound | R | LC RT (minutes) | M + 1 | LC Purity (%) |
|---|---|---|---|---|
| 260 | *—CH₂CH₂—CH(CH₃)CH₃ | 3.08 | 437 | 90 |
| 261 | *—CH₂-(4-pyridyl) | 2.83 | 458 | 90 |
| 262 | *—CH₂-(thiazol-2-yl) | 3.04 | 464 | 90 |
| 263 | *—CH(CH₃)₂ | 2.79 | 409 | 90 |

Example 14

The appropriate acid chloride (0.24 mmol) was added to a solution of 4-[4-fluoro-3-(piperazine-1-carbonyl)benzyl]-2H-phthalazin-1-one (2) (0.2 mmol) in dichloromethane (2 ml). Hunigs base (0.4 mmol) was then added and the reaction was stirred at room temperature for 16 hours. The reaction mixtures were then purified by preparative HPLC.

The compounds synthesised are set out below.

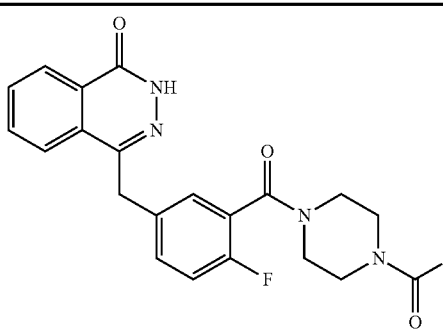

| Compound | R | LC RT (minutes) | M + 1 | LC Purity (%) |
|---|---|---|---|---|
| 264 | *—CH₃ | 3.89 | 409 | 90 |

-continued

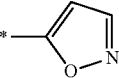

| Compound | R | LC RT (minutes) | M + 1 | LC Purity (%) |
|---|---|---|---|---|
| 265 | 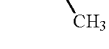 | 4.17 | 462 | 85 |
| 266 |  | 4.04 | 423 | 90 |
| 267 | 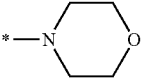 | 4.03 | 417 | 90 |
| 268 | 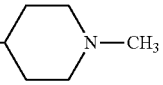 | 3.19 | 480 | 90 |
| 269 | 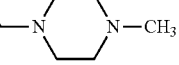 | 2.84 | 492 | 90 |
| 270 | 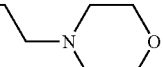 | 2.71 | 521 | 90 |
| 271 |  | 2.83 | 508 | 90 |
| 272 |  | 2.86 | 478 | 90 |
| 273 |  | 2.63 | 521 | 90 |

Example 15

An appropriate aldehyde (0.2 mmol) and 4-[3-([1,4]diazepane-1-carbonyl)benzyl]-2H-phthalazin-1-one (3)(0.24 mmol) were dissolved in dichloromethane (2 ml). Sodium triacetoxyborohydride (0.28 mmol) and glacial acetic acid (6.0 mmol) were then added and stirred at room temperature for 16 hours. The reaction mixtures were then purified by preparative HPLC.

The compounds synthesised are set out below.

| Compound | R | LC RT (minutes) | M + 1 | LC Purity (%) |
|---|---|---|---|---|
| 274 |  | 2.92 | 419 | 90 |
| 275 |  | 3.04 | 433 | 90 |
| 276 |  | 2.78 | 391 | 90 |
| 277 |  | 3.09 | 433 | 90 |
| 278 |  | 2.86 | 405 | 90 |
| 279 |  | 2.88 | 417 | 90 |
| 280 |  | 2.99 | 433 | 90 |
| 281 |  | 3.11 | 459 | 90 |
| 282 |  | 3.06 | 433 | 90 |
| 283 | * — CH2 — (furan) | 2.93 | 443 | 90 |
| 284 | * — (CH2)3 — S — CH3 | 2.92 | 451 | 90 |

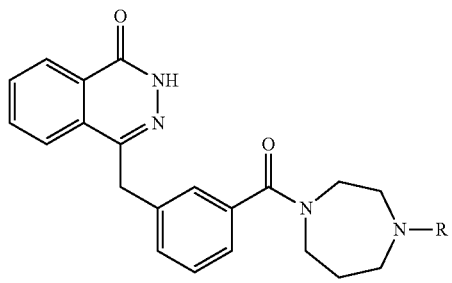
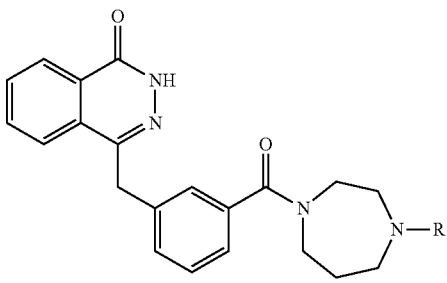
| Compound | R | LC RT (minutes) | M + 1 | LC Purity (%) | Compound | R | LC RT (minutes) | M + 1 | LC Purity (%) |
|---|---|---|---|---|---|---|---|---|---|
| 285 | *—thiophen-3-ylmethyl | 2.99 | 459 | 90 | 292 | *—benzofuran-2-ylmethyl | 3.22 | 493 | 90 |
| 286 | *—1H-pyrrol-2-ylmethyl | 2.94 | 441 | 90 | 293 | *—CH2CH(CH3)2 | 2.91 | 419 | 90 |
| 287 | *—(6,8-dichloro-4-oxo-4H-chromen-3-yl)methyl | 3.36 | 589 | 85 | 294 | *—4-(methoxycarbonyl)benzyl | 3.08 | 511 | 90 |
| 288 | *—(2,4-dioxo-1,2,3,4-tetrahydropyrimidin-5-yl)methyl | 2.72 | 487 | 85 | 295 | *—furan-2-ylmethyl | 2.92 | 443 | 90 |
| 289 | *—4-(methylthio)benzyl | 3.24 | 499 | 90 | 296 | *—4-cyanobenzyl | 3.03 | 478 | 90 |
| 290 | *—CH2CH2OCH2Ph | 3.14 | 497 | 90 | 297 | *—(geranyl-like) | 3.48 | 501 | 90 |
| 291 | *—4-methoxybenzyl | 3.9 | 483 | 85 | 298 | *—4-phenoxybenzyl | 3.39 | 545 | 90 |

-continued

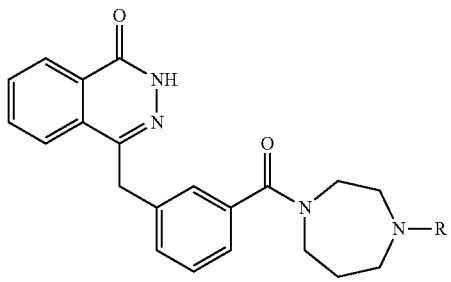

| Compound | R | LC RT (minutes) | M + 1 | LC Purity (%) |
|---|---|---|---|---|
| 299 | *-CH2-(5-methylfuran-2-yl) | 3.06 | 456 | 90 |
| 300 | *-CH2-(2-methoxyphenyl) | 3.8 | 483 | 90 |
| 301 | *-CH2-(5-methylthiophen-2-yl) | 3.08 | 472 | 90 |
| 302 | *-CH2-(1-methyl-1H-indol-3-yl) | 3.22 | 506 | 90 |
| 303 | *-CH2-(5-methoxy-1H-indol-3-yl) | 3.13 | 522 | 90 |
| 304 | *-CH2-(2-methoxynaphthalen-1-yl) | 3.29 | 533 | 90 |
| 305 | *-CH2-(3-benzyloxy-4-methoxyphenyl) | 3.39 | 589 | 90 |
| 306 | *-CH2-(1H-indol-3-yl) | 3.07 | 492 | 90 |

-continued

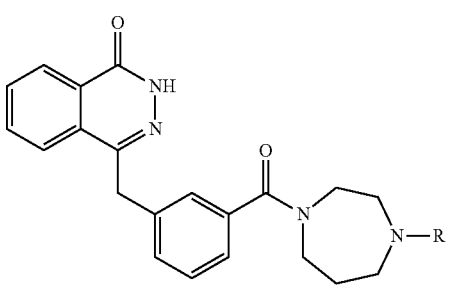

| Compound | R | LC RT (minutes) | M + 1 | LC Purity (%) |
|---|---|---|---|---|
| 307 | *-CH2-(3-methoxy-4-benzyloxyphenyl) | 3.41 | 589 | 90 |
| 308 | *-CH2-(thiazol-2-yl) | 2.87 | 460 | 85 |
| 309 | *-CH2-(4-(dimethylamino)phenyl) | 3.06 | 496 | 90 |
| 310 | *-CH2-(3,5-dimethoxyphenyl) | 3.13 | 513 | 90 |
| 311 | *-CH2-(thiophen-2-yl) | 2.96 | 459 | 90 |
| 312 | *-CH2-phenyl | 2.98 | 453 | 90 |

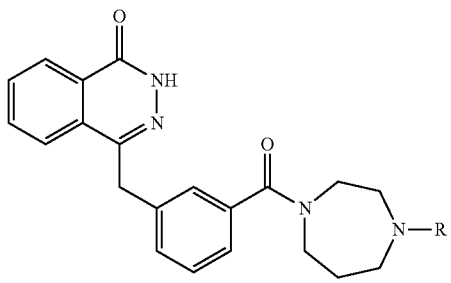

| Compound | R | LC RT (minutes) | M + 1 | LC Purity (%) |
|---|---|---|---|---|
| 313 | (3-fluoro-4-methoxybenzyl) | 3.09 | 501 | 90 |
| 314 | isopropyl | 2.76 | 405 | 90 |

Example 16

The appropriate sulphonyl chloride (0.24 mmol) was added to a solution of 4-[3-([1,4]diazepane-1-carbonyl)benzyl]-2H-phthalazin-1-one (3) (0.2 mmol) in dichloromethane (2 ml). Hunigs base (0.4 mmol) was then added and the reaction was stirred at room temperature for 16 hours. The reaction mixtures were then purified by preparative HPLC.

The compounds synthesised are set out below.

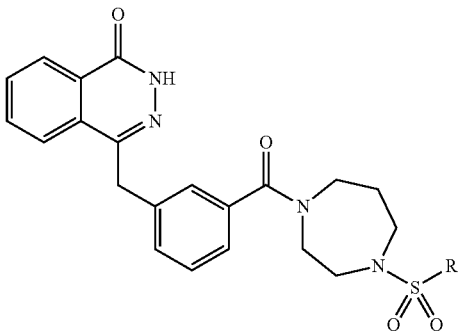

| Compound | R | LC RT (minutes) | M + 1 | LC Purity (%) |
|---|---|---|---|---|
| 315 | 3-CF3-phenyl | 4.15 | 571 | 90 |
| 316 | 4-biphenyl | 4.36 | 579 | 90 |
| 317 | n-butyl | 3.68 | 483 | 90 |
| 371 | 3,5-dimethylisoxazol-4-yl | 3.71 | 523 | 90 |

Example 17

The appropriate acid chloride (0.24 mmol) was added to a solution of 4-[3-([1,4]diazepane-1-carbonyl)benzyl]-2H-phthalazin-1-one (3) in dichloromethane (2 ml). Hunigs base (0.4 mmol) was then added and the reaction was stirred at room temperature for 16 hours. The reaction mixtures were then purified by preparative HPLC.

The compounds synthesised are set out below.

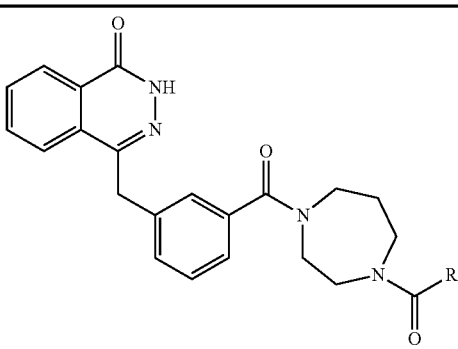

| Compound | R | LC RT (minutes) | M + 1 | LC Purity (%) |
|---|---|---|---|---|
| 318 | (2-phenylcyclopropyl) | 3.84 | 533 | 90 |

-continued

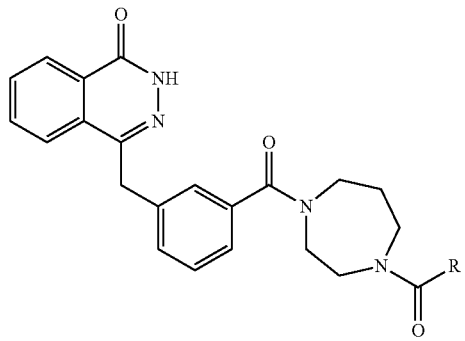

| Compound | R | LC RT (minutes) | M + 1 | LC Purity (%) |
|---|---|---|---|---|
| 319 | 5-isoxazolyl | 3.23 | 458 | 90 |
| 320 | 6-methoxy-2-hydroxypyridin-4-yl | 3.63 | 532 | 90 |
| 321 | -CH2CH2-(4-methoxyphenyl) | 3.61 | 525 | 90 |
| 322 | -CH2CH2-phenyl | 3.63 | 495 | 90 |
| 323 | 4-(methylthio)phenyl | 3.62 | 513 | 90 |
| 324 | -CN | 3.16 | 415 | 90 |
| 325 | C(CH3)=CHCH2CH3 | 3.52 | 459 | 90 |
| 326 | -CH(CH3)CH2CH2CH2CH3 | 3.95 | 489 | 90 |
| 327 | -CH2-(4-trifluoromethylphenyl) | 3.89 | 549 | 90 |

-continued

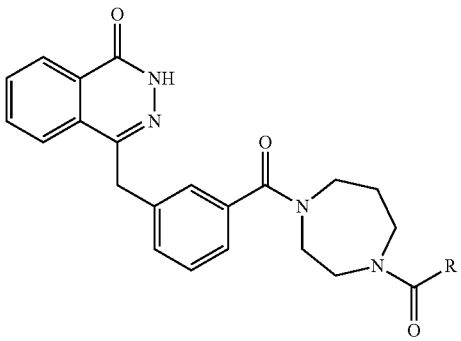

| Compound | R | LC RT (minutes) | M + 1 | LC Purity (%) |
|---|---|---|---|---|
| 328 | -CH2-(biphenyl-4-yl) | 4.00 | 557 | 90 |

Example 18

The appropriate isocyanate (0.24 mmol) was added to a solution of 4-[3-([1,4]diazepane-1-carbonyl)benzyl]-2H-phthalazin-1-one (3) (0.2 mmol) in dichloromethane (2 ml). The reaction was stirred at room temperature for 16 hours. The reaction mixtures were then purified by preparative HPLC.

The compounds synthesised are set out below.

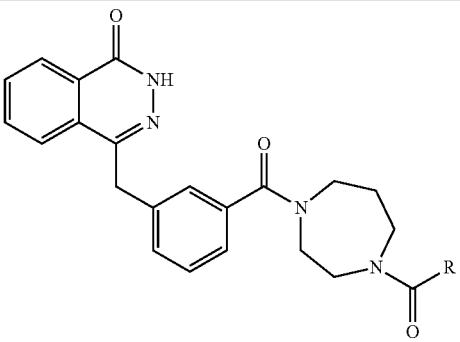

| Compound | R | LC RT (minutes) | M + 1 | LC Purity (%) |
|---|---|---|---|---|
| 329 | -NH-(4-methoxyphenyl) | 3.4 | 512 | 90 |

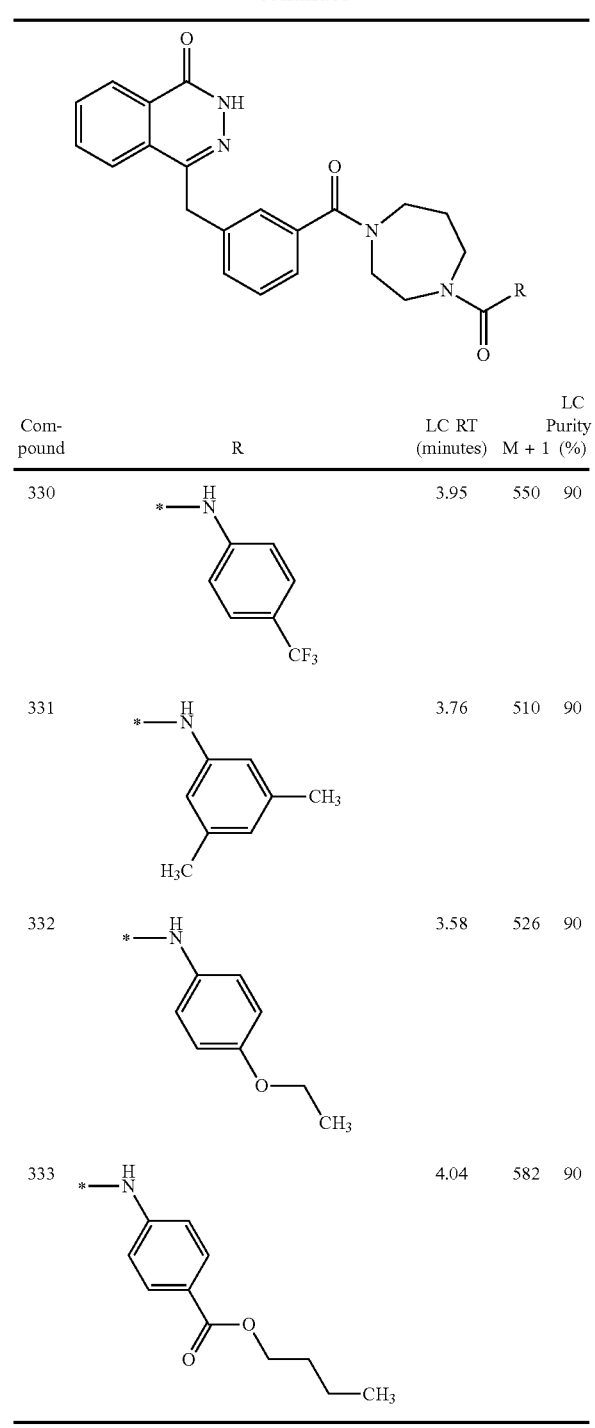

| Compound | R | LC RT (minutes) | M + 1 | LC Purity (%) |
|---|---|---|---|---|
| 330 | *—NH—C6H4—CF3 (4-CF3) | 3.95 | 550 | 90 |
| 331 | *—NH—C6H3(CH3)2 (3,5-diMe) | 3.76 | 510 | 90 |
| 332 | *—NH—C6H4—OCH2CH3 (4-OEt) | 3.58 | 526 | 90 |
| 333 | *—NH—C6H4—C(O)O—CH2CH2CH3 (4-) | 4.04 | 582 | 90 |

Example 19

The appropriate isothiocyanate (0.24 mmol) was added to a solution of 4-[3-([1,4]diazepane-1-carbonyl)benzyl]-2H-phthalazin-1-one (3) (0.2 mmol) in dichloromethane (2 ml). The reaction was stirred at room temperature for 16 hours. The reaction mixtures were then purified by preparative HPLC.

The compounds synthesised are set out below.

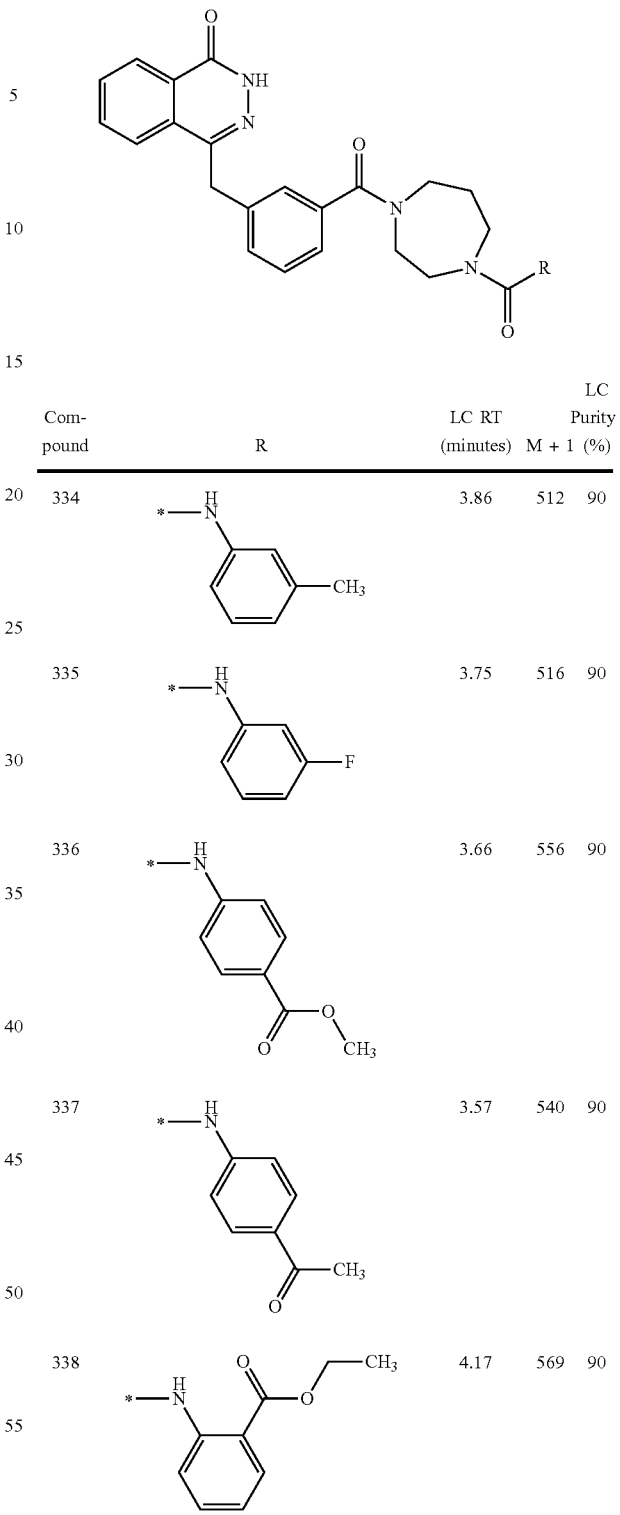

| Compound | R | LC RT (minutes) | M + 1 | LC Purity (%) |
|---|---|---|---|---|
| 334 | *—NH—C6H4—CH3 (3-Me) | 3.86 | 512 | 90 |
| 335 | *—NH—C6H4—F (3-F) | 3.75 | 516 | 90 |
| 336 | *—NH—C6H4—C(O)OCH3 (4-) | 3.66 | 556 | 90 |
| 337 | *—NH—C6H4—C(O)CH3 (4-) | 3.57 | 540 | 90 |
| 338 | *—NH—C6H4—C(O)OCH2CH3 (2-) | 4.17 | 569 | 90 |
| 339 | *—NH—C6H4—C(O)CH3 (3-) | 3.56 | 540 | 90 |

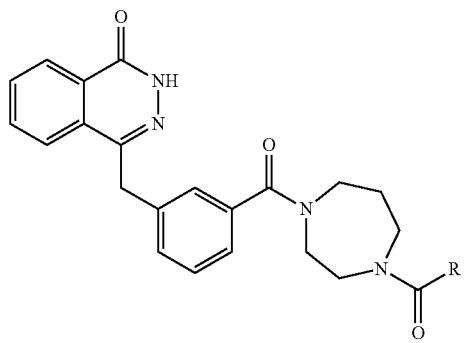
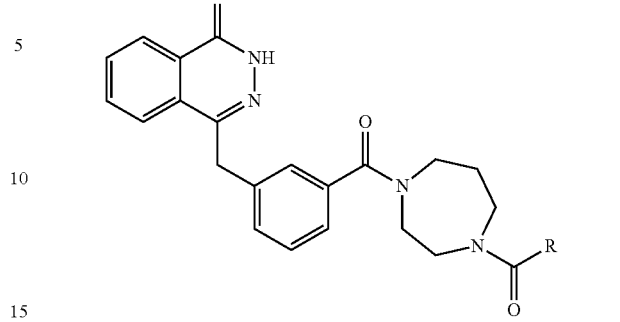

| Compound | R | LC RT (minutes) | M + 1 | LC Purity (%) | Compound | R | LC RT (minutes) | M + 1 | LC Purity (%) |
|---|---|---|---|---|---|---|---|---|---|
| 340 | *—NH—C6H4—N(CH3)2 | 3.1 | 541 | 85 | 346 | *—NH—(2-F-C6H4) | 3.64 | 516 | 90 |
| 341 | *—NH—Ph | 3.84 | 498 | 90 | 347 | *—NH—(2-OCH3-C6H4) | 3.57 | 528 | 90 |
| 342 | *—NH—C6H4—C(O)CH2OCH3 | 3.64 | 556 | 90 | 348 | *—NH—(4-CH3-C6H4) | 3.78 | 512 | 90 |
| 343 | *—NH—(4-OCH3-C6H4) | 3.53 | 528 | 90 | 349 | *—NH—(2-CH3-C6H4) | 3.62 | 512 | 90 |
| 344 | *—NH—C6H4—C(O)OCH3 | 3.92 | 556 | 90 | | | | | |
| 345 | *—NH—(3-CF3-C6H4) | 4.09 | 566 | 90 | | | | | |

Example 20

The appropriate acid chloride (0.24 mmol) was added to a solution of 4-[3-([1,4]diazepane-1-carbonyl)-4-fluorobenzyl]-2H-phthalazin-1-one (4) in dichloromethane (2 ml). Hunigs base (0.4 mmol) was then added and the reaction was stirred at room temperature for 16 hours. The reaction mixtures were then purified by preparative HPLC.

The compounds synthesised are set out below.

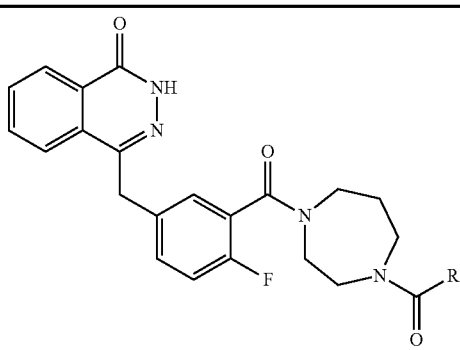

| Compound | R | LC RT (minutes) | M + 1 | LC Purity (%) |
|---|---|---|---|---|
| 372 | *—CH2—N(CH3)(CH3) | 2.81 | 466 | 80 |
| 385 | *—N(morpholine) | 3.19 | 495 | 90 |

Example 21

1-[2-Fluoro-5-(4-Oxo-3,4-dihydrophthalazin-1-ylmethyl) benzoyl]-piperidine-4-carboxylic acid (D) (0.24 mmol) was added to a solution of the appropriate amine (0.2 mmol) in dimethylacetamide (2 ml). 2-(1H-Benzotriazole-1-yl)-1,1,3,3-tetramethyluronium hexafluorophosphate (0.3 mmol) and Hunigs base (0.4 mmol) were then added and the reaction was stirred at room temperature for 16 hours. The reaction mixtures were then purified by preparative HPLC.

The compounds synthesised are set out below.

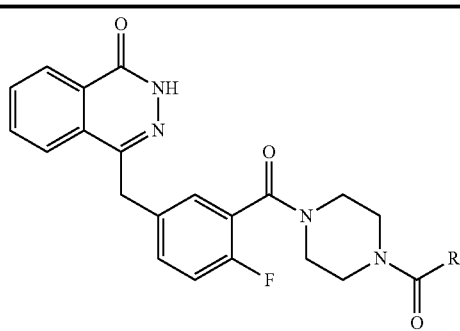

| Compound | R | LC RT (minutes) | M + 1 | LC Purity (%) |
|---|---|---|---|---|
| 386 | *—N(morpholine) | 3.21 | 480 | 90 |

Example 22

In order to assess the inhibitory action of the compounds, the following assay was used to determine $IC_{50}$ values (Dillon, et al., *JBS.,* 8(3), 347-352 (2003)).

Mammalian PARP, isolated from Hela cell nuclear extract, was incubated with Z-buffer (25 mM Hepes (Sigma); 12.5 mM $MgCl_2$ (Sigma); 50 mM KCl (Sigma); 1 mM DTT (Sigma); 10% Glycerol (Sigma) 0.001% NP-40 (Sigma); pH 7.4) in 96 well FlashPlates (TRADE MARK) (NEN, UK) and varying concentrations of said inhibitors added. All compounds were diluted in DMSO and gave final assay concentrations of between 10 and 0.01 μM, with the DMSO being at a final concentration of 1% per well. The total assay volume per well was 40 μl.

After 10 minutes incubation at 30° C. the reactions were initiated by the addition of a 10 μl reaction mixture, containing NAD (5 μM), $^3$H-NAD and 30 mer double stranded DNA-oligos. Designated positive and negative reaction wells were done in combination with compound wells (unknowns) in order to calculate % enzyme activities. The plates were then shaken for 2 minutes and incubated at 30° C. for 45 minutes.

Following the incubation, the reactions were quenched by the addition of 50 μl 30% acetic acid to each well. The plates were then shaken for 1 hour at room temperature.

The plates were transferred to a TopCount NXT (TRADE MARK) (Packard, UK) for scintillation counting. Values recorded are counts per minute (cpm) following a 30 second counting of each well.

The % enzyme activity for each compound is then calculated using the following equation:

$$\% \text{ Inhibition} = 100 - \left(100 \times \frac{(\text{cpm of unknowns} - \text{mean negative cpm})}{(\text{mean positive cpm} - \text{mean negative cpm})}\right)$$

$IC_{50}$ values (the concentration at which 50% of the enzyme activity is inhibited) were calculated, which are determined over a range of different concentrations, normally from 10 μM down to 0.001 μM. Such $IC_{50}$ values are used as comparative values to identify increased compound potencies.

All compounds tested had a $IC_{50}$ of less than 0.1 μM.

The following compounds have an $IC_{50}$ of less than 0.01 μM: 2-5, 9, 10, 12-20, 24, 26-28, 30, 32-35, 38, 39, 42, 44-47, 49, 51, 58-68, 80-82, 84, 86, 88-90, 94-97, 100-105, 113-116, 121-123, 126, 132, 136, 138-140, 142-144, 147, 149, 151, 152, 156, 158, 159, 161-164, 166-175, 177-180, 182-184, 186-190, 194, 199, 202, 205, 207, 208, 213, 221-223, 225, 233-236, 239-274, 277, 279, 287, 288, 292, 293, 301-303, 306, 315, 316, 318-323, 325, 327-336, 338-350, 352-357, 359, 361, 363, 365 and 367-370.

The following compounds, as well as those above, have an $IC_{50}$ of less than 0.02 μM: 1, 6-8, 11, 21-23, 25, 31, 36, 37, 40, 41, 43, 48, 52-54, 56, 57, 69-79, 83, 87, 91-93, 98, 99, 106, 109, 110, 111, 117, 118, 120, 124, 128-130, 133-135, 137, 141, 145, 146, 148, 150, 153-155, 157, 160, 165, 176, 181, 185, 191, 192, 195, 196, 197, 201, 203, 204, 206, 211, 212, 215-217, 219, 220, 224, 226, 227, 229-232, 237, 238, 275, 276, 278, 281-286, 289-291, 294, 295, 297-299, 304, 305, 307-309, 311, 314, 317, 324, 326, 337, 351, 358, 360, 362, 364, 366, 371 and 372.

The Potentiation Factor ($PF_{50}$) for compounds is calculated as a ratio of the $IC_{50}$ of control cell growth divided by the $IC_{H}$ of cell growth+PARP inhibitor. Growth inhibition curves for both control and compound treated cells are in the presence of the alkylating agent methyl methanesulfonate (MMS). The test compounds were used at a fixed concentration of 0.2 micromolar. The concentrations of MMS were over a range from 0 to 10 μg/ml.

Cell growth was assessed using the sulforhodamine B (SRB) assay (Skehan, P., et al., (1990) New colorimetric cytotoxicity assay for anticancer-drug screening. J. Natl. Cancer Inst. 82, 1107-1112). 2,000 HeLa cells were seeded into each well of a flat-bottomed 96-well microtiter plate in a volume of 100 μl and incubated for 6 hours at 37° C. Cells were either replaced with media alone or with media containing PARP inhibitor at a final concentration of 0.5, 1 or 5 μM. Cells were allowed to grow for a further 1 hour before the addition of MMS at a range of concentrations (typically 0, 1, 2, 3, 5, 7 and 10 μg/ml) to either untreated cells or PARP inhibitor treated cells. Cells treated with PARP inhibitor alone were used to assess the growth inhibition by the PARP inhibitor.

Cells were left for a further 16 hours before replacing the media and allowing the cells to grow for a further 72 hours at 37° C. The media was then removed and the cells fixed with 100 μl of ice cold 10% (w/v) trichloroacetic acid. The plates were incubated at 4° C. for 20 minutes and then washed four times with water. Each well of cells was then stained with 104 μl of 0.4% (w/v) SRB in 1% acetic acid for 20 minutes before washing four times with 1% acetic acid. Plates were then dried for 2 hours at room temperature. The dye from the stained cells was solubilized by the addition of 100 μl of 10 mM Tris Base into each well. Plates were gently shaken and left at room temperature for 30 minutes before measuring the optical density at 564 nM on a Microquant microtiter plate reader.

All the compounds tested had a $PF_{50}$ at 200 nM of at least 2.0.

Example 23

Figure 1B:
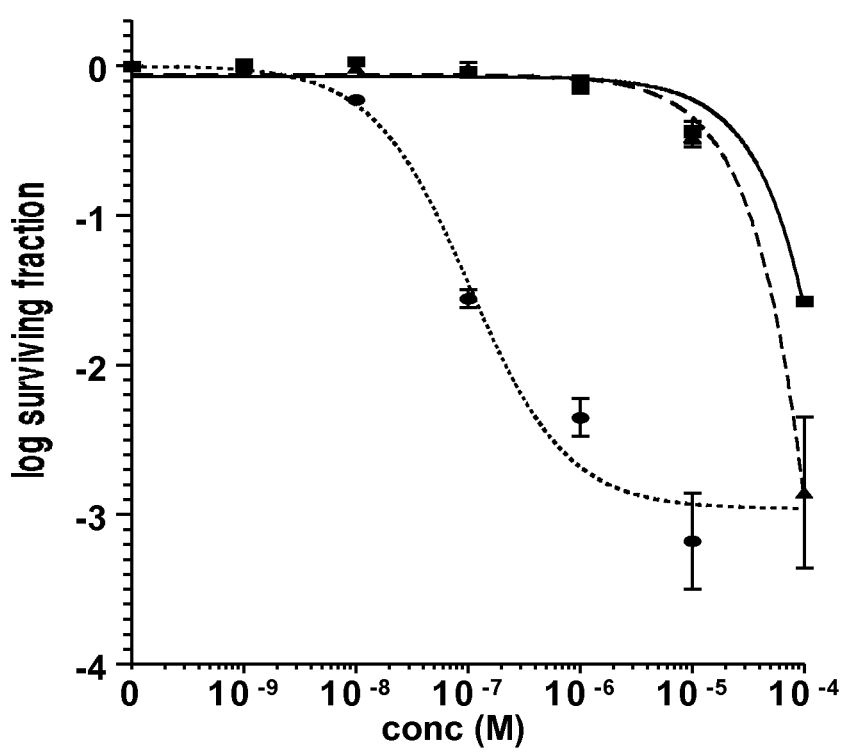

To assess the stand alone activity of a PARP inhibitor on Braca 1 and 2 deficient cells the following protocols were used.
Small Molecule Inhibitors of PARP:
Compound (4) was dissolved in DMSO at 10 mM and stored at −20° C. in the dark.
Cell Lines
VC8 cells and the mouse Brca2 BAC complemented derivatives were as described in M. Kraakman-van der Zwet, et al., *Mol Cell Biol* 22, 669-79 (2002)). ES cells defective in Brca2 function have been described previously (Tutt, et al., *EMBO Rep* 3, 255-60 (2002)). The construction of ES cells defective in Brca1 will be described elsewhere but have previously been validated (Foray, et al., *Embo J,* 22, 2860-71 (2003)).
Clonogenic Assays
For measurement of cellular sensitivity to a PARP inhibitor (compound 4), cell cultures in exponential growth were trypsinised and seeded at various densities in 6-well plates onto Mitomycin C inactivated mouse embryonic fibroblasts and where appropriate treated with the test compound after 18 hours. For continuous exposure, cells were re-fed every 4 days with fresh medium and inhibitor. After 10-14 days, cells were washed with PBS, fixed in methanol and stained with crystal violet. Colonies containing greater than approximately 50 cells were counted. Experiments were performed at least three times in triplicate.
Results
Reduction in the viability of BRCA1 and BRCA2 deficient cells Compound 4 was used to probe the sensitivity of cells deficient in Brca1 or Brca2 to the inhibition of PARP activity. Clonogenic assays showed that both Brca1 and Brca2 deficient cell lines were extremely sensitive to compound 4 compared to otherwise isogenic cells (FIG. 1A, 1B). The $SF_{50}$ (dosage at which 50% of cells survived) for Compound 4 was $1.5 \times 10^{-8}$M for cells deficient in Brca1, whilst the $SF_{50}$ for matched wild type cells was $7 \times 10^{-6}$M (FIG. 1A). This represents a factor of 467 fold enhanced sensitivity of Brca1 mutant cells compared to wild type cells.

Figure 2:
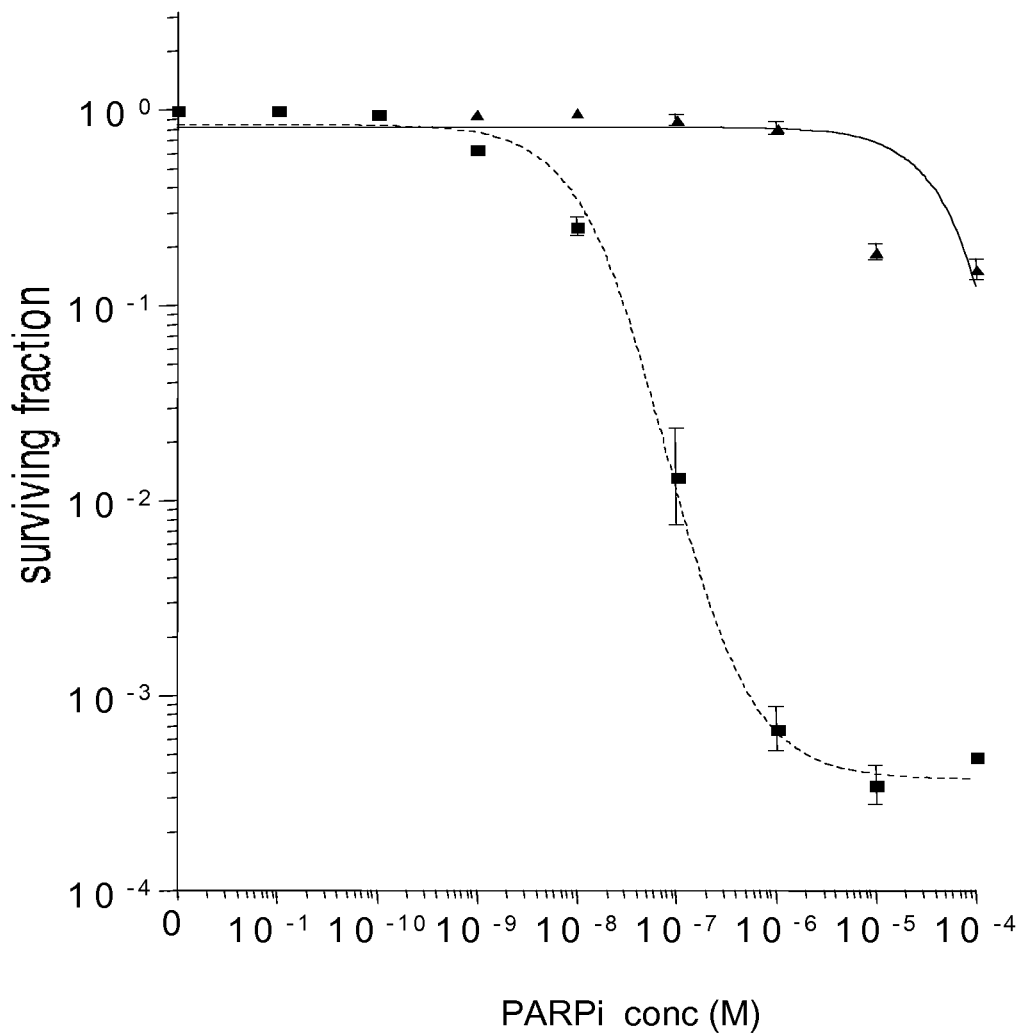
FIG. 2 shows an analysis of the effects of a compound of the invention (4) in another cell line lacking BRCA2 function in comparison to a BRCA2 complemented line. Data shown is clonogenic survival of Brca2 deficient (V-C8:■) and complemented (V-C8 BAC+:▲) cells under continuous exposure to compound 4 at varying concentrations.

The $SF_{50}$ for Compound 4 was $1.2 \times 10$-8M for cells deficient in Brca2 whilst the $SF_{50}$ for matched wild type cells was $1.8 \times 10^{-5}$M (FIG. 1B). This represents a factor of 1,500 fold enhanced sensitivity of Brca2 mutant cells compared to wild type cells. Similar results were obtained with Chinese hamster ovary cells deficient in Brca2 (VC8) compared to a Brca2-complemented derivative (VC8-BAC) (FIG. 2). The $SF_{50}$ for Compound 4 was $5 \times 10^{-8}$M for the Brca2 deficient VC8 line whilst the $SF_{50}$ for matched control, VC8-BAC, was $3 \times 10^{-5}$M (FIG. 2). This represents a factor of 600 fold enhanced sensitivity of Brca2 mutant cells compared to wild type cells.

The invention claimed is:
1. A method of treatment for pancreatic cancer deficient in a HR dependent DNA DSB repair pathway comprising administering to a subject a therapeutically effective amount of a compound of formula (Ib):

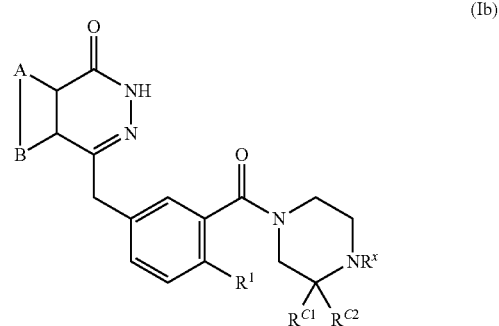

or an isomer or salt thereof, or a mixture of any thereof, wherein:
A and B together represent a fused aromatic ring, optionally substituted with one or more substituent groups selected from halo, nitro, hydroxyl, ether, thiol, thioether, amino, $C_{1-7}$ alkyl, $C_{5-1}$ aryl and a heterocyclyl group having from 3 to 7 ring atoms, of which from 1 to 4 are selected from nitrogen, oxygen and sulfur;
$R^x$ is selected from H, $C_{1-7}$ alkyl, $C_{5-7}$ aryl, amido, thioamido, ester, acyl, and sulfonyl groups and a heterocyclyl group having from 3 to 7 ring atoms, of which from 1 to 4 are selected from nitrogen, oxygen and sulfur, wherein the acyl, $C_{1-7}$ alkyl, $C_{5-7}$ aryl or heterocyclyl group is optionally substituted with one or more substituent groups selected from $C_{1-7}$ alkyl, $C_{5-7}$ aryl, halo, hydroxyl, ether, nitro, cyano, acyl, carboxy, ester, amido, amino, acylamido, ureido, acyloxy, thiol, thioether, sulfoxide, sulfonyl, thioamido, sulfonamido and a heterocyclyl group having from 3 to 7 ring atoms, of which from 1 to 4 are selected from nitrogen, oxygen and sulfur;
$R^{C1}$ and $R^{C2}$ are both hydrogen; and
$R^1$ is selected from H and halo;
wherein the cancer is pancreatic cancer; and
wherein the cancer comprises one or more cancer cells having a reduced or abrogated ability to repair DNA DSB by HR relative to normal cells.
2. The method of claim 1, wherein the fused aromatic ring represented by A and B together is benzene.

3. The method of claim 1, wherein $R^1$ is selected from H, Cl, and F.

4. The method of claim 1, wherein $R^x$ is selected from H, $C_{1-7}$ alkyl, $C_{5-7}$ aryl, acyl, sulfonyl, amido, and thioamido groups, wherein the acyl, $C_{1-7}$ alkyl or $C_{5-7}$ aryl group is optionally substituted with one or more substituent groups selected from $C_{1-7}$ alkyl, $C_{5-7}$ aryl, halo, hydroxyl, ether, nitro, cyano, acyl, carboxy, ester, amido, amino, acylamido, ureido, acyloxy, thiol, thioether, sulfoxide, sulfonyl, thioamido, sulfonamido and a heterocyclyl group having from 3 to 7 ring atoms, of which from 1 to 4 are selected from nitrogen, oxygen and sulfur.

5. The method of claim 1, wherein the compound of formula (Ib) or an isomer or salt thereof, or a mixture of any thereof, is a compound of formula (II):

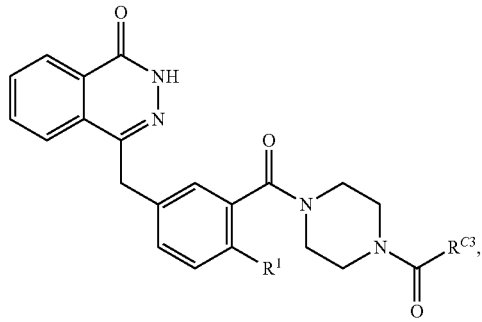

(II)

or an isomer or salt thereof, or a mixture of any thereof, wherein:

$R^{C3}$ is selected from $C_{1-7}$ alkyl, $C_{5-7}$ aryl, and a heterocyclyl group having from 3 to 7 ring atoms, of which from 1 to 4 are selected from nitrogen, oxygen and sulfur, wherein the $C_{1-7}$ alkyl, $C_{5-7}$ aryl or heterocyclyl group is optionally substituted with one or more substituent groups selected from $C_{1-7}$ alkyl, $C_{5-7}$ aryl, halo, hydroxyl, ether, nitro, cyano, acyl, carboxy, ester, amido, amino, acylamido, ureido, acyloxy, thiol, thioether, sulfoxide, sulfonyl, thioamido, sulfonamido and a heterocyclyl group having from 3 to 7 ring atoms, of which from 1 to 4 are selected from nitrogen, oxygen and sulfur.

6. The method of claim 1, wherein the compound of formula (Ib) or an isomer or salt thereof, or a mixture of any thereof, is a compound of formula (III):

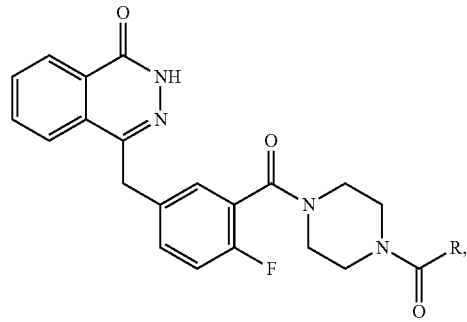

(III)

or an isomer or salt thereof, or a mixture of any thereof, wherein R is selected from:

a) 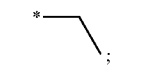

b) 

c) 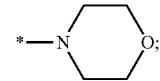

d) 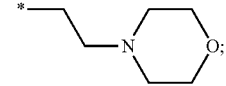

e) 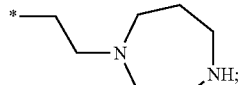

f) 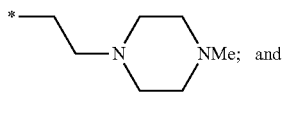

g) 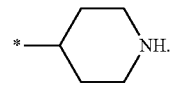

7. The method of claim 1, wherein the compound of formula (Ib) or an isomer or salt thereof, or a mixture of any thereof, is a compound of formula (IV),

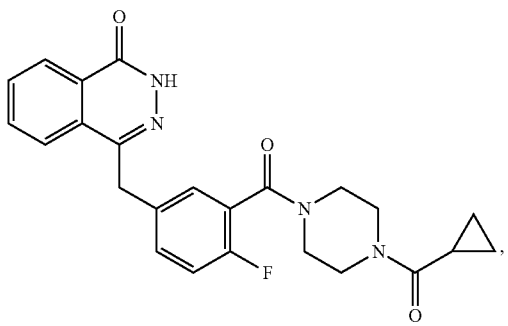

(IV)

or an isomer or salt thereof, or a mixture of any thereof.

8. The method of claim 1, further comprising identifying the subject as having a cancer condition that is deficient in a HR dependent DNA DSB repair pathway.

9. The method of claim 1, further comprising administering ionizing radiation, a chemotherapeutic agent, or a combination thereof to the subject.

10. The method of claim 1, wherein the one or more cancer cells has a BRCA1 or BRCA2 deficient phenotype.

11. The method of claim 10, wherein the one or more cancer cells are deficient in BRCA1 or BRCA2.

12. The method of claim 1, wherein the subject is heterozygous for a mutation in a gene encoding a component of the HR dependent DNA DSB repair pathway.

* * * * *